United States Patent
McAuliffe et al.

(10) Patent No.: US 12,156,661 B2
(45) Date of Patent: *Dec. 3, 2024

(54) METHODS OF DESIGNING A SURGICAL DEVICE

(71) Applicants: SMITH & NEPHEW SURGICAL PTY. LTD, North Ryde (AU); Michael McAuliffe, Silkstone (AU)

(72) Inventors: Michael McAuliffe, Silkstone (AU); Daniel Raymond Lawson, Lane Cove West (AU); Shuo Shi, Dundas Valley (AU); Conan B. Cavanagh, Galway (IE)

(73) Assignees: Michael McAuliffe, Silkstone (AU); Smith & Nephew Surgical PTY. LTD, North Ryde (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/139,516

(22) Filed: Apr. 26, 2023

(65) Prior Publication Data

US 2023/0329727 A1    Oct. 19, 2023

Related U.S. Application Data

(63) Continuation of application No. 17/154,541, filed on Jan. 21, 2021, now abandoned, which is a
(Continued)

(30) Foreign Application Priority Data

May 26, 2015  (AU) .................. 2015901930
Jul. 31, 2015   (AU) .................. 2015903054

(51) Int. Cl.
*A61B 17/17*   (2006.01)
*A61B 17/15*   (2006.01)
(Continued)

(52) U.S. Cl.
CPC ........ *A61B 17/1764* (2013.01); *A61B 17/154* (2013.01); *A61B 17/155* (2013.01);
(Continued)

(58) Field of Classification Search
CPC ... A61B 17/56; A61B 17/1764; A61B 17/154; A61B 17/155; A61B 17/157; A61B 34/10; A61B 2034/108; A61B 2017/568
See application file for complete search history.

(56) References Cited

U.S. PATENT DOCUMENTS 8,070,752 B2    12/2011  Metzger et al.
8,556,983 B2    10/2013  Bojarski et al.
(Continued)

FOREIGN PATENT DOCUMENTS

WO    2009/076296 A2    6/2009
WO    2011/028624 A1    3/2011
(Continued)

OTHER PUBLICATIONS

International Search Report and Written Opinion for International Patent Application No. PCT/AU2016/050409, mailed Sep. 2, 2016.
(Continued)

*Primary Examiner* — Anu Ramana
(74) *Attorney, Agent, or Firm* — KDW Firm PLLC

(57) ABSTRACT

Provided is a method for designing a patient-specific surgical device for performing knee surgery, which includes determining a first alignment axis and/or a second alignment axis from a knee joint in extension and/or flexion respectively and subsequently designing said surgical device based on the first and/or second alignment axes. Also provided is a method of manufacturing a patient-specific surgical device designed by the aforementioned method. A patient-specific surgical device designed and/or manufactured by the above
(Continued)

methods and a method of performing knee surgery with said patient-specific surgical device is further provided.

31 Claims, 24 Drawing Sheets

Related U.S. Application Data continuation of application No. 15/574,950, filed as application No. PCT/AU2016/050409 on May 26, 2016, now Pat. No. 10,952,753.

(51) Int. Cl.
    *A61B 34/10*     (2016.01)
    *A61B 17/00*     (2006.01)
    *A61B 17/56*     (2006.01)

(52) U.S. Cl.
    CPC ............ *A61B 17/157* (2013.01); *A61B 34/10* (2016.02); *A61B 2017/00526* (2013.01); *A61B 2017/568* (2013.01); *A61B 2034/105* (2016.02); *A61B 2034/108* (2016.02)

(56) References Cited

U.S. PATENT DOCUMENTS

| | | |
|---|---|---|
| 8,617,171 B2 | 12/2013 | Park et al. |
| 8,715,289 B2 | 5/2014 | Smith |
| 8,801,720 B2 | 8/2014 | Park et al. |
| 8,903,530 B2 | 12/2014 | Metzger |
| 9,675,471 B2 | 6/2017 | Bojarski et al. |
| 9,743,940 B2 | 8/2017 | Catanzarite et al. |
| 9,757,238 B2 | 9/2017 | Metzger |
| 9,839,486 B2 | 12/2017 | Hughes et al. |
| 10,925,622 B2 | 2/2021 | Kehres et al. |
| 2007/0288030 A1 | 12/2007 | Metzger et al. |
| 2009/0209884 A1 | 8/2009 | Van Vorhis et al. |
| 2011/0029091 A1* | 2/2011 | Bojarski ............... A61F 2/389 606/86 R |
| 2011/0029116 A1 | 2/2011 | Jordan et al. |
| 2012/0209394 A1 | 8/2012 | Bojarski et al. |
| 2013/0211531 A1 | 8/2013 | Steines et al. |
| 2014/0276240 A1 | 9/2014 | Stein et al. |

FOREIGN PATENT DOCUMENTS

| | | |
|---|---|---|
| WO | 2014/063084 A1 | 4/2014 |
| WO | 2015/160852 A1 | 10/2015 |

OTHER PUBLICATIONS

International Preliminary Report on Patentability for International Patent Application No. PCT/AU2016/050409, mailed Nov. 28, 2017.
Extended European Search Report for EP Patent Application No. 16798958.1, mailed Feb. 11, 2019.
Examination Report No. 1 for Australian Patent Application No. 2016267404, mailed Apr. 7, 2020.

\* cited by examiner

Scheme A cont'd

METHODS OF DESIGNING A SURGICAL DEVICE

CROSS-REFERENCE TO RELATED APPLICATIONS

This application is a continuation of U.S. patent application Ser. No. 17/154,541, filed on Jan. 21, 2021, which application is a continuation of U.S. patent application Ser. No. 15/574,950, filed on Nov. 17, 2017, now U.S. Pat. No. 10,952,753, issued on Mar. 23, 2021, which application is a United States National Phase filing of International Application No. PCT/AU2016/050409, filed May 26, 2016, which claims priority to and the full benefit of Australian Provisional Application Serial No. 2015903054, filed Jul. 31, 2015 and Australian Provisional Application Serial No. 2015901930, filed May 26, 2015, and titled "METHOD OF DESIGNING A SURGICAL DEVICE", the entire contents of each prior application are incorporated herein by reference.

FIELD

THIS INVENTION described herein relates generally to a method of designing a device for use in surgery. In particular, the invention is directed to a method of designing a customized device for use in knee surgery and, in particular, total knee replacement that achieves optimal soft tissue balancing and joint line restoration in a subject in both flexion and extension.

BACKGROUND

Total knee arthroplasty (TKA) or total knee replacement (TKR) is a surgical technique in which a surgical implant is inserted to replace the knee joint. Typically, TKA/TKR is a successful and long lasting surgical procedure but 10-20% of patients express some dissatisfaction regarding the outcome of the procedure or suffer from persistent pain. The skilled artisan would recognize that to achieve a good clinical outcome with TKR, correct implant sizing and alignment, optimal soft tissue balancing, equal flexion and extension gaps and joint line restoration are required.

Standard or universal cutting or resection blocks may be used to prepare the distal portion of a femur and/or the proximal portion of a tibia in total knee arthroplasties (TKA's). Such cutting blocks are generally mounted to the femur and tibia by an adjustable instrument referenced by and extending from an intramedullary or extramedullary rod and then subsequently directly to the resected surface of the femur and tibia. The instruments are made adjustable so that they may be applied universally to patients. While there are many benefits to adjustable instruments, there also exist many disadvantages. Some disadvantages include increased overhead, bulky kits and containers, unnecessary or redundant instruments, large numbers of trials and different sizes, increased sterilization time between surgeries, and increased financial risks to orthopaedic manufacturers to maintain largely unused inventory. Furthermore, the universal instruments do not consistently reproduce the joint line and balance throughout the range of motion of the knee that is both within normal limits and specific to that patient.

More recently, the surgical process of TKA/TKR has been streamlined by the introduction of customised resection guides (also referred to as patient-specific or patient-matched instrumentation) so as to avoid one or more of the aforementioned disadvantages of standard resection instruments. They do fail however to consistently reproduce correct ligament balance throughout knee range of motion. Such customized resection guides are typically formed using patient-specific anatomical data derived from, for example, a CT or MRI scan of a patient's knee joint.

Prior art customised resection members have generally been designed to make bony resections that either: (i) match an approximation of a patient's pre-arthritic knee anatomy; or (ii) are aligned with the mechanical axis of the patient's knee. With regard to the pre-arthritic knee anatomy-matched resection members of (i), these devices are designed to place the cuts so that the knee is returned to its former anatomical alignment prior to any loss of articular cartilage. Such devices are based solely on partial scans of the knee joint that are used to approximate mechanical axes by extrapolating a fixed number of degrees from the small anatomical axis portion visible thereon.

Conversely, mechanical axis-aligned customised resection members measure the pre-operative mechanical axes based on scans typically of the entire limb including the ipsilateral hip and ankle joint. Such resection members aim to restore the alignment of a patient's limb to this mechanical axis at the end of the procedure. To this end, the devices are orientated using current surgical principles and are typically placed in relation to the mechanical axis of the limb based on the knee joint in an extended or near extended position.

Notably, neither of the aforementioned types of customised guides are designed so as to take into consideration the relationship of the femoral and tibial resections in TKA/TKR and their orientation with respect to each other in both extension and flexion. Accordingly, current patient-specific or customised resection members may fail to achieve a correctly aligned and/or balanced knee throughout its full range of motion. When a knee prosthesis is installed without being properly aligned and/or balanced multiple problems can arise. These can include stiffness, poor range of movement, pain, instability and, excessive shear forces at the interface between bony surfaces and the prosthesis, leading to subsequent failure of the prosthesis and surgical revision. Accordingly, an improved method of designing customised resection guides of various design that achieve correct surgical alignment of the knee joint together with optimal soft tissue balancing in both extension and flexion is required.

SUMMARY

The present invention is broadly directed to a method of designing a patient-specific or customised device for performing knee surgery and, in particular, TKR. The method may be performed to design patient-specific or customised resection members and/or guides for precise realignment and tensioning of the knee in both flexion and extension by way of coupling measurement of the femoral and tibial cuts in relation to the joint line and/or each other. The invention is further directed to patient-specific surgical devices produced therefrom and their use in knee surgery.

In a first aspect, the invention is directed to a method of designing a patient-specific surgical device for performing knee surgery on the patient including the steps of:
  (i) determining a first alignment axis from one or a plurality of first anatomical indicators on a patient-specific model of the patient's limb in extension
  (ii) determining a second alignment axis from one or a plurality of second anatomical indicators on a patient-specific model of the patient's limb in flexion; and (iii) designing the patient-specific surgical device based at least partly on the determined first and/or second alignment axes so that the patient-specific surgical device is adapted to at least partly align a femur and/or a tibia of said limb with the first and/or second alignment axes.

In an embodiment, the method includes the step of using patient-specific anatomical data of a limb in both flexion and extension to create the patient-specific model of said limb, prior to steps (i) and (ii). Preferably, the patient-specific model is or comprises a three dimensional model.

In particular embodiments, the one or plurality of first anatomical indicators are selected from the group consisting of a central portion of a femoral head, a central portion of a femoral shaft, an intramedullary canal insertion point, a deepest portion of a trochlear groove, a central portion of an intercondylar notch, a central portion of a line extending between medial and lateral tibial spines, a central portion of a talus, a central portion of a tibial shaft and an anterior cruciate ligament tibial attachment point.

In one embodiment, the first alignment axis is or comprises a tibial mechanical axis, a femoral mechanical axis and/or a lower limb mechanical axis or an axis substantially parallel thereto.

In one embodiment, the method of the present aspect further includes the step of rotating the tibia of the extended limb in a coronal plane relative to the femur, such that the tibial mechanical axis, the femoral mechanical axis and/or the lower limb mechanical axis are substantially parallel to the first alignment axis.

In one embodiment, the one or plurality of second anatomical indicators is or comprises a femoral anteroposterior axis, a tibial anteroposterior axis and/or a tibial mechanical axis and the second alignment axis is substantially parallel thereto. In another embodiment, the one or plurality of second anatomical indicators is or comprises a transepicondylar axis (TEA) and/or a posterior condylar axis and the second alignment axis is substantially perpendicular thereto.

Suitably, the method of the present aspect further comprises the step of determining a flexion axis from one or a plurality of third anatomical indicators on the patient-specific model of the limb, wherein the tibia is rotated relative to the femur about the flexion axis so as to substantially match the degree of flexion that exists between the femur and the tibia in the patient-specific anatomical data of the limb in extension.

In one embodiment, the one or plurality of third anatomical indicators are or comprise a lateral condyle arc centre and a medial condyle arc centre of the femur, such that the flexion axis extends therebetween.

In one embodiment, the one or plurality of second anatomical indicators is or comprises the flexion axis and the second alignment axis is substantially perpendicular thereto.

Suitably, the method of the present aspect further comprises the step of determining a joint line from one or a plurality of fourth anatomical indicators. Preferably, the one or plurality of fourth anatomical indicators are selected from the group consisting of a distal portion of a medial condyle, a distal portion of a lateral condyle, a proximal portion of a medial tibial plateau, a proximal portion of a lateral tibial plateau, a central portion of a lateral meniscus and a central portion of a medial meniscus.

Suitably, the method of the present aspect further comprises the step of determining a distal resection plane of the femur when the knee is in extension from at least partly the joint line, the first alignment axis and/or a first dimension of a femoral prosthesis to be fitted on said femur. In one embodiment, the distal resection plane is substantially parallel to the joint line and/or is substantially perpendicular to the first alignment axis. In a further embodiment, the distance between the distal resection plane and the joint line is substantially equal to the first dimension of the femoral prosthesis. In an alternative embodiment, the distance between the distal resection plane and the joint line is about 0.5 mm to about 1.5 mm greater than the first dimension of the femoral prosthesis.

Suitably, the method of the present aspect further comprises the step of determining a proximal resection plane of the tibia when the knee is in extension from at least partly the distal femoral resection plane, the first dimension of the femoral prosthesis to be fitted on said femur, a first dimension of a tibial prosthesis to be fitted on said tibia and/or the joint line. In particular embodiments, the proximal resection plane is: (i) substantially parallel to the joint line of the knee in extension; (ii) substantially perpendicular to the first alignment axis; and/or (iii) substantially parallel to the distal femoral resection plane of the knee in extension, when viewed in a coronal and/or sagittal plane of the limb. In alternative embodiments, the proximal resection plane is at an angle of: (i) about 0.5 degrees to about 15 degrees relative to the joint line and/or the distal femoral resection plane; and/or (ii) about 75 degrees to about 89.5 degrees relative to the first alignment axis, when viewed in a sagittal plane of the limb. In one embodiment, the distance between the proximal tibial resection plane and the distal femoral resection plane are substantially equal to the sum of the first dimension of the femoral prosthesis and the first dimension of the tibial prosthesis. In another embodiment, the distance between the proximal resection plane and the distal resection plane is about 0.5 mm to about 2.5 mm greater than the sum of the first dimension of the femoral prosthesis and the first dimension of the tibial prosthesis.

In one embodiment, the method of the present aspect further includes the step of rotating the tibia of the flexed limb in a coronal plane relative to the femur, such that the proximal resection plane is substantially perpendicular to the second alignment axis.

Suitably, the method of the present aspect further comprises the step of determining a posterior resection plane of the femur when the knee is in flexion from at least partly the second alignment axis, the proximal tibial resection plane, the first dimension of the tibial prosthesis to be fitted on the tibia and/or a second dimension of the femoral prosthesis to be fitted on the femur In one embodiment, the posterior resection plane is substantially perpendicular to the second alignment axis and/or is substantially parallel to the proximal tibial resection plane when viewed in a coronal and/or sagittal plane of the limb. In an alternative embodiment, the proximal resection plane is at an angle of: (i) about 0.5 degrees to about 15 degrees relative to the posterior resection plane; and/or (ii) about 75 degrees to about 89.5 degrees relative to the second alignment axis, when viewed in a sagittal plane of the limb. In a further embodiment, the distance between the posterior resection plane and the proximal resection plane is substantially equal to the sum of the first dimension of the tibial prosthesis and the second dimension of the femoral prosthesis. In an alternative embodiment, the distance between the posterior resection plane and the proximal resection plane is about 0.5 mm to about 2.5 mm greater than the sum of the first dimension of the tibial prosthesis and the second dimension of the femoral prosthesis.

In a particular preferred embodiment, the distal resection plane defines a distal femoral cut thickness and positioning, the proximal resection plane defines a proximal tibial cut thickness and positioning and/or the posterior resection plane defines a posterior femoral cut thickness and positioning such that a post-resection gap from said tibia to said femur is approximately equal in extension and in flexion of the knee.

Suitably, the method of any one of the preceding claims, wherein the patient-specific model of the limb is created using both soft tissue and bony tissue data from the patient-specific anatomical data and optionally further comprises the step of incorporating patient-specific kinematic and/or biomechanical data into the patient-specific model of the limb.

In certain embodiments, the method further comprises the step of determining a position of one or a plurality of guide apertures in the patient-specific surgical device for indicating or facilitating positioning of a resection member on the femur and/or tibia, wherein the resection member comprises one or a plurality of resection apertures for guiding a resection tool along the distal resection plane, the proximal resection plane, the posterior resection plane and/or an anterior resection plane of the femur. Preferably, the guide apertures indicate or facilitate positioning of (i) a distal resection member on the femur; (ii) a proximal resection member on the tibia; and/or (iii) an anteroposterior resection member on the femur.

In other embodiments, the method further comprises the step of determining a position of one or a plurality of resection apertures in the patient-specific surgical device for guiding a resection tool along the distal resection plane, the proximal resection plane, the posterior resection plane and/or an anterior resection plane of the femur.

In one embodiment, the patient-specific surgical device comprises a spacer for insertion between the femur and tibia to facilitate at least partial return of the knee joint to an appropriate alignment with the first alignment axis and/or the second alignment axis.

Suitably, the patient-specific surgical device is adapted to engage the femur and/or the tibia in extension and/or flexion.

In certain embodiments, the patient-specific surgical device is designed so as to facilitate, at least partly, return of the knee to an appropriate and/or balanced soft tissue tension when in extension and/or flexion.

In particular embodiments, with respect to appropriate soft tissue tension, medial and/or lateral soft tissue laxity of the knee in flexion and/or extension is about 10 to about 7.0°.

In certain embodiments, with respect to balanced soft tissue tension, the difference between medial and lateral soft tissue laxity of the knee is or less than about 5°.

In certain embodiments, the method further comprises the step of obtaining the patient-specific anatomical data of the limb in flexion and/or extension.

In a second aspect, the invention provides a method of manufacturing a patient-specific surgical device comprising the steps of:
 (i) designing the patient-specific surgical device at least partly by the method of the first aspect; and
 (ii) manufacturing the patient-specific surgical device based at least partly on the design of step (i).

In a third aspect, the invention provides a patient-specific surgical device for performing knee surgery on said patient, wherein the patient-specific surgical device is adapted to at least partly align a femur and/or a tibia of a limb with: (i) a first alignment axis determined from one or a plurality of first anatomical indicators on a model of said patient's limb in extension; and/or (ii) a second alignment axis determined from one or a plurality of second anatomical indicators on a model of said patient's limb in flexion.

Suitably, the patient-specific surgical device is manufactured by the method of the second aspect.

In a fourth aspect, the invention provides a patient-specific surgical device manufactured by the method of the second aspect.

In a fifth aspect, the invention provides a method of performing knee surgery on a patient comprising the step of engaging the patient-specific surgical device of the second aspect on a knee of said patient.

It will be appreciated that the indefinite articles "a" and "an" are not to be read as singular indefinite articles or as otherwise excluding more than one or more than a single subject to which the indefinite article refers.

As used herein, unless the context requires otherwise, the words "comprise", "comprises" and "comprising" will be understood to mean the inclusion of a stated integer or group of integers but not the exclusion of any other non-stated integer or group of integers.

BRIEF DESCRIPTION OF THE DRAWINGS

In order that the present invention may be readily understood and put into practical effect, reference will now be made to the accompanying illustrations, wherein like reference numerals are used to refer to like elements.

FIG. 9: is a front view (A) and medial side view (B) of the flexed knee joint of 3D model of. FIG. 8 illustrating an example of determining a posterior femoral resection plane from the profiles of a tibial prosthesis and a femoral prosthesis.

DETAILED DESCRIPTION

The present invention relates to a method of designing patient-specific surgical devices for use during surgery and, in particular, TKR/TKA, for determining the thickness and positioning of one or more bony resections so as to achieve an appropriate alignment with one or more joint axes and/or an appropriate soft tissue balance of the knee joint in both flexion and extension. While patient-specific or customised surgical devices are particularly suited for use in TKR/TKA, the present invention has general applicability to all types of joints (e.g., elbows, shoulders, wrists and fingers) and replacement surgery thereof that requires accurate gap balancing, joint alignment and/or soft tissue balancing.

While the principles described herein are based on methods of providing patient-specific surgical devices for humans, this invention may also be extended to other mammals such as livestock (e.g. cattle, sheep), performance animals (e.g. racehorses) and domestic pets (e.g. dogs, cats), although without limitation thereto.

The invention provides, in part, a method for determining resection planes to be used in designing a patient-specific or customised surgical device. This patient-specific surgical device may generally be designed and created using patient-specific anatomical information or data obtained from a knee joint in both flexion and extension. By way of example, the patient-specific surgical device may be a patient-specific or customised resection member for use in a total or partial joint replacement surgical procedure. Non-limiting examples of customised cutting guides include those by Zimmer, Signature guides by Biomet, Visionaire guides by Smith and Nephew, Trumatch guides by Depuy, Prophecy guides by Wright Medical, My Knee guides by Medacta and Shape Match guides by Otis Med. Alternatively, the patient-specific surgical device may be a patient-specific or customised surgical or resection guide, such as that disclosed in WO 2012/024306 and also described herein.

Figure 23:
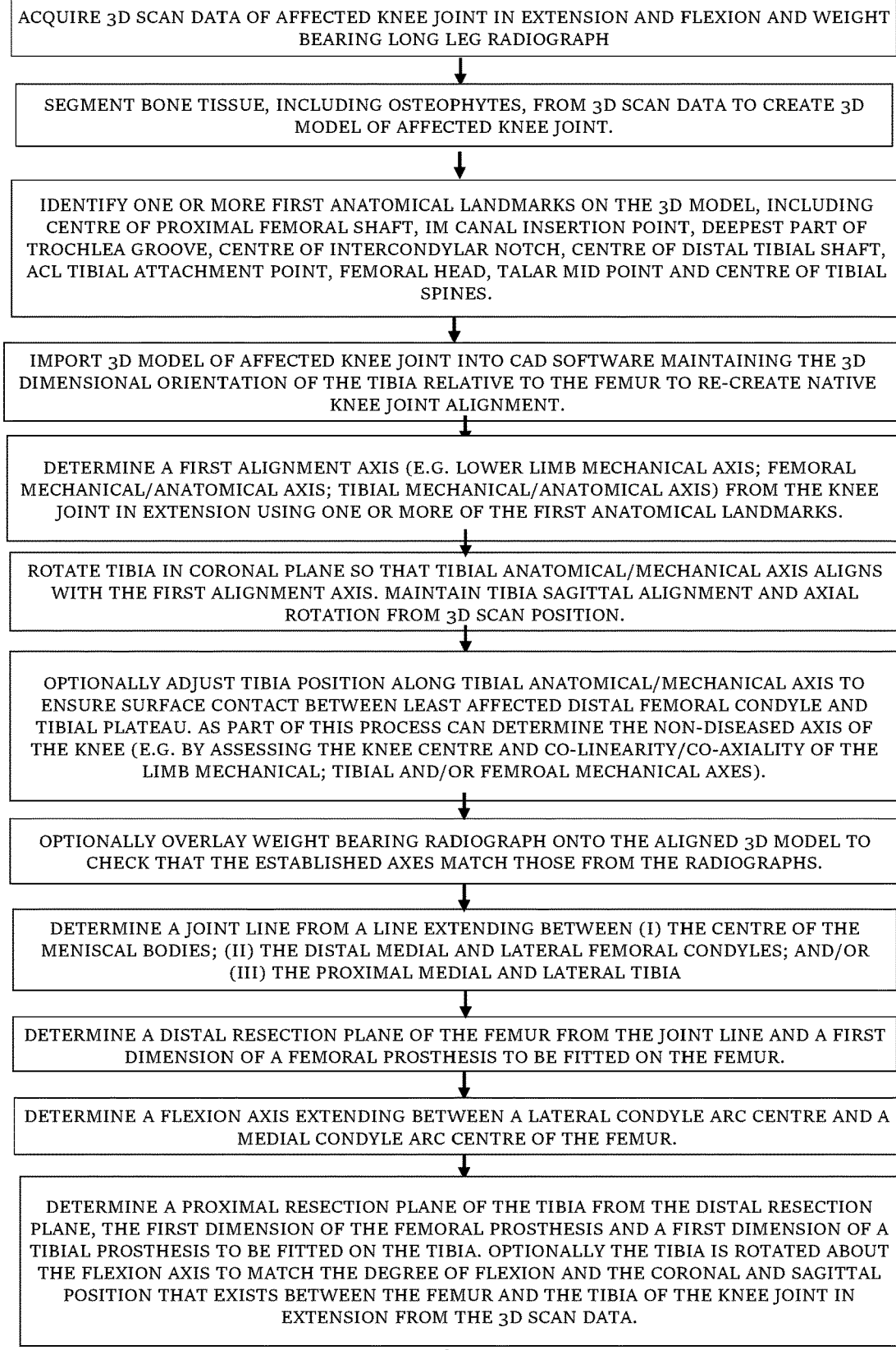
FIGS. 23 and 24. Demonstrate an embodiment (Scheme A) of a method of providing a patient-specific surgical device for a knee joint according to the invention described herein.
Figure 24:
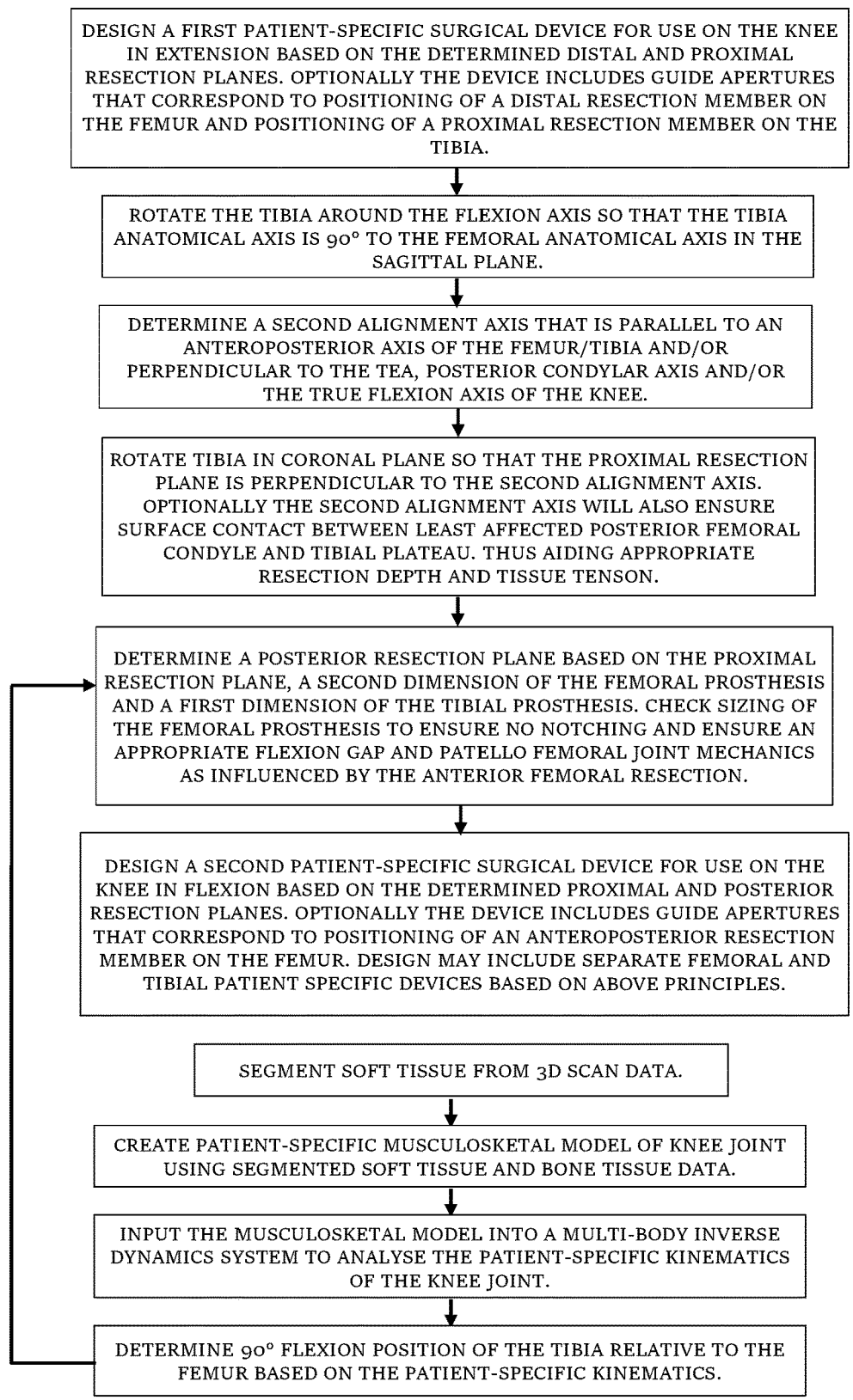

Scheme A (FIGS. 23 and 24) demonstrates an embodiment of the method of providing a patient-specific surgical device for a knee joint according to the invention described herein.

Suitably, patient-specific anatomical data is obtained pre-operatively using one or more non-invasive imaging modalities, such as radiological imaging, computerised tomography (CT)/computerised axial tomography (CAT), magnetic resonance imaging (MRI), inclusive of full limb MRI, ultrasound and/or other conventional means. The patient-specific anatomical data obtained therefrom may then be pre-processed and/or converted to form a patient-specific model of the joint. Such a patient-specific model may include a two dimensional model (e.g., radiographs, 2D slices of MRI) and/or a three dimensional model. Preferably, the patient-specific model is or comprises a three dimensional model, such as a three-dimensional (3D) computer aided design (CAD) model. Alternatively, the anatomical data may be used in its raw form to identify one or more anatomical indicators and/or determine an alignment and/or a flexion axis prior to being converted into a three dimensional model of the patient's limb. Generally, segmentation of the bone tissue, including osteophytes, from the patient-specific anatomical data is performed to thereby create a three dimensional model of the affected knee joint.

In particular embodiments, the method of the present aspect includes obtaining a full scan of a patient's limb. For economical or efficiency purposes, however, one or more partial scans of a patient's limb may be used rather than a full limb scan. In this regard, the exact location of each partial scan relative to a patient's limb may be carefully noted to ensure that the scans are spaced apart in all directions correctly before determining one or more of the indicators and/or axes (e.g., the first alignment axis) provided herein. Furthermore, one or more partial scans may be utilised when a particular landmark, such as the true femoral head centre or the transepicondylar axis, cannot be determined and/or has been compromised due to trauma or gross deformation.

Suitably, the patient-specific anatomical data is used to determine a first alignment axis from one or a plurality of first anatomical indicators of a patient's limb prior to designing the customised surgical device for said patient. In this regard, a proximal portion and a distal portion of a patient's limb are typically identified. The patient's first alignment axis may then be determined by projecting and extending an imaginary line between the identified proximal and distal portions. Further, it would be appreciated that additional anatomical indicators therebetween may be used in determining the first alignment axis of a patient's limb and the relationship between the overall axis and the intercalated segments thereof (e.g., the femoral and tibial mechanical axes).

By way of example, the proximal portion may be a centroid of the femoral head and the distal portion may be the mid point of the superior most apex of a talus bone. At the knee joint, the intercalated segments can be marked by the sulcus of the intercondylar/trochlear groove or the mid point of the line between the tibial spines. Accordingly, in one embodiment, the first alignment axis is or comprises a patient's mechanical axis of the knee joint. To this end, the non-diseased mechanical axis of the lower limb typically represents a line drawn from the centre of the femoral head to the centre of the ankle joint, passing through the knee just medial to the centre of the knee. In both the normal and the osteoarthritic knee, this axis may be assessed as its component femoral and tibial parts.

In an alternative embodiment, the first alignment axis is based at least partly on the pre-arthritic knee anatomy of the patient. A pre-arthritic mechanical or anatomical axis of the limb or knee joint may be calculated by manipulation of the patient-specific anatomical data with regards to the overall mechanical axis of the limb (i.e., lower limb mechanical axis) and the intercalated segments represented by the femoral and tibial mechanical axes. This will typically place the limb in a±3 degree range from neutral. Preferably, however, determining the first alignment axis in this manner will be individualised for the specific patient's anatomy. For example, a patient whose knee joint may realign in 3 degrees of varus will generally not be placed in the "safe" zone at 2 degrees valgus as this represents a 5 degree deviation from their "ideal" alignment.

Suitably, the first alignment axis of the limb is determined from one or a plurality of first anatomical indicators on the patient-specific model of the limb in extension. In one embodiment, the first anatomical indicators are selected from the group consisting of a central portion of a femoral head, a central portion of a femoral shaft, an intramedullary canal insertion point, a deepest portion of a trochlear groove, a central portion of an intercondylar notch, a central portion of a tibial spine, a central portion of a talus, a central portion of a tibial shaft, an anterior cruciate ligament tibial attachment point.

Accordingly, in particular embodiments, the first alignment axis is a mechanical axis of the limb, a femoral mechanical/anatomical axis and/or a tibial mechanical/anatomical axis. Furthermore, it would be appreciated that the first alignment axis may comprise more than one component axis. By way of example, the first alignment axis may comprise a femoral mechanical axis and a tibial mechanical axis of the limb. Accordingly, in one embodiment, the first alignment axis is or comprises a tibial mechanical/anatomical axis, a femoral mechanical/anatomical axis and/or a lower limb mechanical axis or an axis substantially parallel thereto.

In one embodiment, the central portion of the tibial spine or intercondylar eminence is determined, at least in part, by a line extending between a lateral intercondylar tubercle and a medial intercondylar tubercle. Accordingly, the central portion of the tibial spine may be the midpoint of this line extending between the two intercondylar tubercles.

With regards to the femoral and/or tibial shafts, any central portion/s or point/s along the shaft, such as proximal, middle or distal central portions, may be used as the first anatomical indicator by the skilled person in performing the method of the present aspect.

It would be readily understood that the present invention should not be limited to the specific examples of anatomical indicators provided herein. Rather, the term anatomical indicator as used herein refers to a readily identifiable feature, specific area and/or landmark within or on a limb, such as an arm or leg, and/or a bone, such as a femur or tibia. In this regard, the anatomical indicators used for determining, for example, a mechanical axis of the limb, a tibial mechanical/anatomical axis, a femoral mechanical/anatomical axis, a flexion axis, a transepicondylar axis (TEA), a posterior condylar axis, a tibial anteroposterior axis, a femoral anteroposterior axis and a joint line, are not to be limited to those anatomical indicators provided herein, but may also include other anatomical indicators as are known in the art.

In one embodiment, the method of the present aspect further includes the step of rotating the tibia of the extended limb in a coronal plane relative to the femur, such that the tibial mechanical axis, the femoral mechanical axis and/or the lower limb mechanical axis are substantially parallel and/or co-axial to the first alignment axis. It would further be appreciated that the method may further include the step of translating the tibia of the extended limb in a coronal plane relative to the femur to facilitate alignment of the knee joint. Accordingly, following such rotation and/or translation of the tibia, two or more of the tibial mechanical axis, the femoral mechanical axis and the lower limb mechanical axis may be parallel and/or co-axial with each other. An example of such an alignment incorporating the tibial mechanical axis, the femoral mechanical axis and the lower limb mechanical axis is provided in FIG. 16.

Suitably, the patient-specific anatomical data of the limb in extension is obtained when the limb is in full extension (i.e., approximately 180 degrees). The skilled artisan, however, would appreciate that this may not be possible or feasible in all patients, owing, for example, to the presence of pre-existing disease or deformities of the limb. By way of example, a patient with a flexion deformity or contracture of the knee may be physically unable to fully straighten or extend the knee. Accordingly, in certain embodiments, the anatomical data of the limb in extension is obtained when the limb is not fully extended.

Preferably, for the patient-specific anatomical data of the limb in flexion, the knee joint is in approximately 85 to approximately 95 degrees of flexion, including, but not limited to, 85, 85.5, 86, 86.5, 87, 87.5, 88, 88.5, 89, 89.5, 90, 90.5, 91, 91.5, 92, 92.5, 93, 93.5, 94, 94.5, 95 degrees or any range therein. In a particular preferred embodiment, the knee joint is in approximately 90 degrees of flexion.

It would be understood that for certain knee replacement systems, such as the Journey™ range of knee replacement systems, assessment of the patient-specific anatomical data of the limb in flexion may occur in knee joints in up to about 110 degrees of flexion. Accordingly, in certain embodiments, for the patient-specific anatomical data of the limb in flexion, the knee joint is in approximately 95 to approximately 110 degrees of flexion, including, but not limited to, 95, 95.5, 96, 96.5, 97, 97.5, 98, 98.5, 99, 99.5, 100, 100.5, 101, 101.5, 102, 102.5, 103, 103.5, 104, 104.5, 105, 105.5, 106, 106.5, 107, 107.5, 108, 108.5, 109, 109.5, 110 degrees or any range therein. In a particular preferred embodiment, the knee joint is in approximately 105 degrees of flexion.

As used herein, the terms "approximately" and "about" refer to tolerances or variances associated with numerical values recited herein. The extent of such tolerances and variances are well understood by persons skilled in the art. Typically, such tolerances and variances do not compromise the structure, function and/or implementation of the devices and methods described herein.

As demonstrated in Scheme A, the patient-specific anatomical data may also be used to determine a second alignment axis of a patient's limb prior to designing the customised surgical device for said patient. In this regard, the second alignment axis of the limb is suitably determined from one or a plurality of second anatomical indicators on the patient-specific model of the limb in flexion. In one embodiment, the second anatomical indicator is or comprises a femoral anteroposterior axis, a tibial anteroposterior axis and/or a tibial anatomical/mechanical axis and the second alignment axis is substantially parallel to either one or more of these axes. By way of example, the femoral anteroposterior axis may be the perpendicular to the flexion and/or rotational axis of the femur.

It is to be understood that the second alignment axis may also be or comprise any other femoral rotational axis known in the art, such as a posterior condylar axis; a transepicondylar axis (TEA); a rotational axis of the knee within the condyles and Whiteside's line. By way of example, the femoral anteroposterior axis may be determined, at least in part from the TEA, Whitesides line, the posterior condylar axis or a combination of two or more of these axes. Accordingly, in one embodiment, the second anatomical indicator is or comprises a transepicondylar axis (TEA) and/or a posterior condylar axis and the second alignment axis is substantially perpendicular thereto. In an alternative embodiment, the second anatomical indicator is or comprises a transepicondylar axis (TEA) and/or a posterior condylar axis and the second alignment axis is at an angle of about 80 degrees to about 100 degrees, relative thereto. In particular embodiments of the present invention, the second alignment axis is at an angle of about 80, 81, 82, 83, 84, 85, 86, 87, 88, 89, 90, 91, 92, 93, 94, 95, 96, 97, 98, 99, 100 degrees or any range therein, relative to the transepicondylar axis and/or the posterio condylar axis.

With respect to defining or determining the TEA, including the surgical and/or anatomical TEA, this may be performed by any method known in the art. It is well established that the determination of the epicondyles may lead to some confusion. On the lateral side of the femur, the prominence of the lateral condyle typically makes the lateral epicondyle easy to define. However on the medial side, the most prominent part of the medial epicondyle, which is generally recognized on a CT scan as the most proximal ridge that gives insertion to the superficial collateral ligament, may be used to determine the anatomical transepicondylar axis (aTEA). Alternatively, the depression below called the medial epicondylar sulcus may be used to define the surgical transepicondylar axis (sTEA).

It would be appreciated that the patient-specific surgical device provided by the method of the present aspect is suitably adapted to at least partly align a femur and/or a tibia of said limb with the first alignment axis, the second alignment axis and/or the flexion axis. In this regard, once the first and/or second alignment axes have been determined, any coronal realignment (if required) of the extended or flexed tibia relative to these axes can then be performed on the patient-specific model of the patient's limb. Typically, the degree and type of any deformity and/or defect, such as varus and valgus, of the knee joint in question are assessed on the patient-specific model. This then allows for a determination of the amount of varus or valgus rotation (i.e. medial or lateral rotation of the tibia relative to its corresponding femur in a coronal arc) that is required by the patient-specific surgical device for angular correction of the tibia and the knee joint line relative to the first and/or second alignment axes.

By way of example, if a patient were to exhibit a 10 degree varus deformity of the knee (i.e., the distal part of the leg below the knee is deviated inward 10 degrees from the long axis of the femur, resulting in a bowlegged appearance), then they would typically require a correction of 7 to 13 degrees externally or valgus rotation of the tibia to achieve ideal joint alignment within the ±3 degree comfort zone. This translation would proceed through the arc of approximately 7-13 degrees, but ceasing at the point limited by the soft tissues and the judgement of the surgeon or user regarding restoration of alignment. Once coronal alignment has been performed on the patient-specific model, weight bearing anteroposterior and/or lateral radiographs may be checked or overlayed so as to check that the femoro-tibial alignment matches that required by said radiographs.

Preferably, sagittal alignment and/or axial rotation of the tibia and/or femur are unchanged from their native or pre-operative state, as per the patient-specific anatomical data, after aligning the femur and/or tibia of said limb with the first alignment axis and/or the second alignment axis. It would be appreciated by the skilled artisan, however, that in order to achieve optimal coronal alignment additional translational and/or rotational correction or alignment of the knee joint may be required so as to account for, at least in part, any deformity caused by, for example, osteoarthritis and in doing so achieve a "true" neutral coronal alignment of the limb.

As shown in Scheme A, application of the method suitably requires the determination of a joint line on the patient-specific model of the aligned knee in extension. As would be readily understood, engagement of the lateral and medial femoral condyles with the superior surface of the tibia of the extended knee establishes a joint line. Accordingly, such determination may be made at least in part from one or a plurality of fourth anatomical indicators, including, but not limited to, a distal portion of a medial condyle, a distal portion of a lateral condyle, a proximal portion of the medial tibial plateau, a proximal portion of the lateral tibial plateau, a central portion of a lateral meniscus and a central portion of a medial meniscus. Accordingly, the joint line may be determined by drawing a line between the mid points of the bodies of the patient's medial and lateral menisci in the coronal plane. Alternatively, it may be determined by drawing a line in relation to the distal portion of the femoral condyle (i.e., medial and/or lateral) least altered or deformed by any osteoarthritic changes present therein. Suitably, the joint line is at an angle of about 85 degrees to about 95 degrees to the first alignment axis of the femur. In particular embodiments, the joint line is at an angle of about 85, 86, 87, 88, 89, 90, 91, 92, 93, 94, 95 degrees or any range therein, to the first alignment axis of the femur. Preferably, the joint line is substantially perpendicular (i.e., about 90 degrees relative) to the first alignment axis of the femur.

A distal resection plane of the femur may then be established on the patient-specific model from the determined joint line and a profile or dimension of a femoral component or prosthesis to be fitted on the femur. By way of example, a profile or dimension may be selected from one or more standard prosthetic devices, or custom prosthetic devices. The profile or dimension may be obtained from one or more product lines which may be from one or more implant manufacturers as are known in the art. Said profile or dimension typically indicate the size and/or positioning of one or more bony resections needed to fit a particular standard or custom prosthetic device. Preferably, the profile or dimension is of a prosthesis that has been sized and fitted appropriately for best coverage, bone conservation, flexion gap stability, patella tracking and/or placement without anterior femoral notching.

Once selected by a user, the profile of a femoral prosthesis, and/or one or more dimensions thereof, may be superimposed onto the patient-specific model of the affected joint bone. Typically, the distal resection plane of the femur is determined from the profile and/or first dimension of the femoral prosthesis and its positioning on the femur relative to the joint line. Preferably, the femoral prosthesis is positioned on the femur so as to allow for appropriate articulation thereof with an adjacent tibial prosthesis. Generally, the distal resection plane is also appropriately aligned on the patient-specific model relative to the first alignment axis.

Preferably, the distal resection plane is substantially parallel to the joint line of the knee and/or is substantially perpendicular to the first alignment axis. Additionally, it would be understood that the distal resection plane typically reproduces the limb alignment determined for the knee joint in extension, such as in embodiments wherein the tibial mechanical, femoral mechanical and lower limb mechanical axes are substantially parallel and/or coaxial.

In one embodiment, the distance between the joint line and the distal resection plane is substantially equal to the first dimension of the femoral prosthesis to be fitted on the femur. In alternative embodiments, the distance between the joint line and the distal resection plane is about 0.5 mm to about 1.5 mm greater than the first dimension of the femoral prosthesis to be fitted on the femur. Typically, this distance of about 0.5 mm to about 1.5 mm would depend upon surgeon preference, but its application is based on previous work demonstrating this "over resection" may be necessary in some patients to normalise periarticular tissue tension. Accordingly, this additional distance of about 0.5 mm to about 1.5 mm may allow for the maintenance of normal soft tissue tension post surgery in the majority of cases. The determination of this "over resection" may also be in part determined by inputs from patient-specific kinematic and/or biomechanical models accounting for bone and soft tissue inputs.

This additional distance may also be applied unilaterally to the patient's knee joint and in particular to the non-diseased side of the joint. By way of example, in a varus knee, the distance between a lateral portion of the joint line and a lateral portion of the distal resection plane may be about 0.5 mm to about 1.5 mm greater than the first dimension of the femoral prosthesis to be fitted on the femur. Conversely, in a valgus knee, the distance between a medial portion of the joint line and a medial portion of the distal resection plane may be about 0.5 mm to about 1.5 mm greater than the first dimension of the femoral prosthesis to be fitted on the femur.

Suitably, CAD programs, biomechanical modelling software and Finite Element Analysis software or the like may be utilised to virtually test a given prosthesis' performance. For example, once a profile is fixed in space on a model of a patient's limb, a prosthesis having the same profile as a bony interface may be superimposed on the patient-specific model. Software may perform iterative test runs to predict whether or not small adjustments to the positioning of the prosthesis are necessary to optimise performance of both the kinematics of the prosthesis/knee and tension/balance of the periarticular soft tissues.

A proximal resection plane of the tibia may also be established from the patient-specific model of the patient's knee. In particular embodiments, wherein the knee joint is in extension, the proximal resection plane of the tibia is determined from at least partly the distal resection plane of the femur, the first dimension of the femoral prosthesis to be fitted on said femur, the joint line and/or a first dimension of a tibial prosthesis to be fitted on said tibia. To this end, and similar to that described above for the distal resection plane, the profiles, or one or more dimensions thereof, of the femoral and tibial prostheses may be superimposed onto the patient-specific model of the affected knee joint. Typically, the proximal resection plane of the tibia is determined from the distal resection plane and appropriate positioning of the femoral and tibial prostheses on the femur and tibia respectively of the patient-specific model that allows for suitable articulation therebetween. Generally, the proximal resection plane is also appropriately aligned on the patient-specific model relative to the first alignment axis.

Typically, tibial prostheses include a tibial bearing or meniscal replacement component having a concave articular portion configured for articulation with the femoral prosthesis and a tibial tray to which the bearing or meniscal replacement component of the tibial prosthesis may be secured. The tibial tray is generally secured to the bone stock of a resected proximal tibia. As is well known in the art, the bearing or meniscal replacement component is used to provide an appropriate level of friction and contact area at the interface between the femoral component and the tibial bearing component.

In one embodiment, the distance between the distal resection plane and the proximal resection plane is substantially equal to the sum of the first dimension of the femoral prosthesis and the first dimension of the tibial prosthesis. In alternative embodiments, the distance between the distal resection plane and the proximal resection plane is about 0.5 mm to about 2.5 mm greater than the sum of the first dimension of the femoral prosthesis and the first dimension of the tibial prosthesis. As hereinbefore described, this additional distance may be applied unilaterally to the patient's knee joint, such as to the non-diseased side of the joint.

In other embodiments, wherein the knee joint is in extension, the proximal resection plane of the tibia is determined from at least partly the joint line and/or the first dimension of the tibial prosthesis to be fitted on the tibia. To this end, the proximal resection plane of the tibia may be determined from the profile and/or first dimension of the tibial prosthesis and its positioning on the tibia relative to the joint line. Preferably, the tibial prosthesis is positioned on the tibia in the patient-specific model so as to allow for appropriate articulation thereof with an adjacent femoral prosthesis.

In one embodiment, the distance between the proximal resection plane and the joint line is substantially equal to the first dimension of the tibial prosthesis. In alternative embodiments, the distance between the joint line and the proximal resection plane is about 0.5 mm to about 1.5 mm greater than the first dimension of the tibial prosthesis.

In particular embodiments, when the patient-specific model of the knee is in extension, the proximal resection plane is: (i) substantially parallel to the joint line; (ii) substantially parallel to the distal femoral resection plane; and/or (iii) substantially perpendicular to the first alignment axis when viewed in relation to the coronal and/or sagittal plane of the limb of the relevant knee joint.

It would be appreciated by the skilled person, however, that the proximal resection plane may possess an anteroposterior slope when viewed in the sagittal plane. Accordingly, the proximal resection plane may only be substantially parallel to the joint line, substantially parallel to the distal femoral resection plane; and/or substantially perpendicular to the first alignment axis when viewed in a coronal plane, but not the sagittal plane owing to the aforementioned anteroposterior slope. This slope is typically appropriate to the prosthesis to be fitted on the tibia and the individual patient's anatomy. Generally, this slope of the proximal resection plane is between about 0 and about 15 degrees, including, but not limited to, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0 degrees or any range therein.

Accordingly, in particular embodiments the proximal resection plane is at an angle of (i) about 0.5 degrees to about 15 degrees relative to the joint line and/or the distal femoral resection plane; and/or (ii) about 75 degrees to about 89.5 degrees relative to the first alignment axis, when viewed in a sagittal plane of the limb.

Suitably, the method of the present aspect further comprises the step of determining a flexion axis which preferably extends through the condylar arc centres of the femur so as to at least partly facilitate reproduction of the relationship between the patient's femur and tibia in the sagittal and coronal planes. This position may also be partly determined by patient specific kinematic and/or biomechanical data and models, as described herein.

As noted previously, it may not be possible to fully extend or near fully extend a patient's knee, such as in cases of a fixed flexion deformity. Accordingly, when designing a patient-specific surgical device, the tibia may need to be rotated relative to the femur about the flexion axis on the patient-specific model so as to substantially match the degree of flexion that exists between the femur and tibia in the patient's "fully" extended knee preoperatively. Additionally, the tibia may need to be translated relative to the femur on the patient-specific model so as to substantially match the spatial relationship that exists between the femur and tibia preoperatively. This rotation and/or translation of the tibia femur on the patient-specific model may be performed prior to determining the proximal and/or distal resection plane. Alternatively, the proximal and/or distal resection plane may be determined and then similarly rotated relative to the femur about the flexion axis on the patient-specific model so as to match the degree of flexion of the native knee. As such, in particular embodiments, the proximal resection plane and/or the distal resection plane are at least partly determined from the flexion axis.

Once the proximal and distal resection planes have been determined from the patient-specific model of the knee in extension or near extension, the posterior femoral resection plane may be determined from the patient-specific model of the knee in flexion. To this end, the tibia of the patient-specific model may be rotated relative to the femur around the flexion axis, such that a tibial component of the mechanical axis is approximately at 90 degrees to a femoral component of the mechanical axis in the sagittal plane. The position of the 3D model of the tibia relative to the femur in 90 degrees of flexion can be verified from patient-specific anatomical data obtained from the patient's knee imaged pre-operatively at approximately 90 degrees of flexion.

Once the patient-specific model of the knee has been rotated to a flexed position, a second alignment axis of the limb may then be determined from one or a plurality of second anatomical indicators thereon. It is to be understood that the second alignment axis may be or comprise any femoral rotational axis known in the art. In one embodiment, the second anatomical indicator is or comprises a femoral anteroposterior axis and/or a tibial anteroposterior axis and the second alignment axis is substantially parallel thereto. In a further embodiment, the second anatomical indicator is or comprises a TEA and/or a posterior condylar axis and the second alignment axis is substantially perpendicular thereto.

Once the second alignment axis has been determined, coronal alignment of the 90 degree rotated tibia relative to the second alignment axis may be performed. Accordingly, in one embodiment, the method of the present aspect further includes the step of rotating the tibia of the flexed limb in a coronal plane relative to the femur, such that the proximal resection plane is substantially perpendicular to the second alignment axis. Suitably, after performing coronal alignment of the tibia, the proximal resection plane is at an angle of about 85 degrees to about 95 degrees (i.e., about 85, 86, 87, 88, 89, 90, 91, 92, 93, 94, 95 degrees or any range therein) to the second alignment axis when viewed in the coronal and/or sagittal planes of the knee joint. Preferably, after performing coronal alignment of the tibia, the proximal resection plane is substantially perpendicular to the second alignment axis when viewed in the coronal and/or sagittal planes of the knee joint. As noted earlier, however, the proximal resection plane may alternatively possess an anteroposterior slope (e.g., between about 75 and about 90 degrees, or any range therein, relative to the second alignment axis) when viewed in the sagittal plane.

Suitably, the posterior resection plane of the femur when the knee is in flexion can now be determined at least partly from the proximal tibial resection plane, the first dimension of the tibial prosthesis to be fitted on the tibia and/or a second dimension of the femoral prosthesis to be fitted on the femur. In one embodiment, the distance between the posterior femoral resection plane and the proximal tibial resection plane is substantially equal to the sum of the first dimension of the tibial prosthesis and the second dimension of the femoral prosthesis. In an alternative embodiment, the distance between the posterior resection plane and the proximal resection plane is about 0.5 mm to about 2.5 mm greater than the sum of the first dimension of the tibial prosthesis and the second dimension of the femoral prosthesis.

In certain preferred embodiments, wherein the knee joint is in flexion, the proximal tibial and/or posterior femoral resection planes are substantially perpendicular to the second alignment axis and/or an anteroposterior axis of the femur. As hereinbefore described, the proximal resection plane may be at an anteroposterior slope when viewed in the sagittal plane. Accordingly, in the flexed knee, the proximal resection plane may only be substantially perpendicular to the second alignment axis and/or an anteroposterior axis of the femur and/or substantially parallel to the posterior femoral resection plane when viewed in the coronal plane of the limb, but not the sagittal plane owing to the aforementioned anteroposterior slope.

Accordingly, in particular embodiments, the proximal resection plane is (i) at an angle of about 0.5 degrees to about 15 degrees relative to the posterior resection plane; and/or (ii) at an angle of about 75 degrees to about 89.5 degrees relative to the second alignment axis and/or the anteroposterior axis of the femur, when viewed in a sagittal plane of the limb.

Preferably, the second alignment axis ensures surface contact between the least affected posterior femoral condyle and an opposing portion of the tibial plateau after coronal alignment of the flexed knee joint.

With respect to the angle of the knee in flexion, the skilled addressee would recognize that this angle will typically be dependent upon the subsequent TKR system to be used by the surgeon. In this regard, most TKR systems require the flexion angle to be approximately 85 to 95 degrees, and in particular about 90 degrees. There are, however, TKR systems such as the Journey TKR systems by Smith and Nephew that require the flexion angle to be approximately 100 to 110 degrees. Nonetheless, it should be readily apparent to the skilled artisan that the devices of the first and second aspect are not to be limited to any particular customised TKR system or method.

Suitably, the distal resection plane defines a distal femoral cut thickness and positioning, the proximal resection plane defines a proximal tibial cut thickness and positioning and/or the posterior resection plane defines a posterior femoral cut thickness and positioning such that a post-resection gap from the tibia to the femur is approximately equal in extension and flexion of the knee joint and that by using this method a ligament tension more individualised to that specific patient will be achieved. One skilled in the art would appreciate that a patient's flexion gap may be approximately equal to that of their extension gap, however, a flexion gap may be more lax than its corresponding extension gap and there is often some mediolateral asymmetry in both flexion and extension in the native knee. Current TKR methods may not produce balanced flexion and extension gaps or may attempt to "normalise" the gaps which may act to impose incorrect tissue tension on an individual knee. Hence the need to provide an improved method of planning resection planes for patient-specific surgical devices for TKR which will produce balance and individualisation of this balance to specific patients.

In one embodiment, the distal femoral resection plane is substantially parallel to the proximal tibial resection plane when the knee joint is in extension, such that an extension gap from the tibia to the femur is substantially rectangular after performing distal and proximal resections. In a further embodiment, the proximal tibial resection plane is substantially parallel to the posterior femoral resection plane when the knee joint is in flexion, such that a flexion gap from the tibia to the femur is substantially rectangular after performing proximal and posterior resections.

It would be appreciated by the skilled artisan, that one or more of the resection planes described herein may be determined, at least in part, with the aid of inputted soft tissue data, as shown in Scheme A. In this regard, segmented soft tissue and bone data from the patient-specific anatomical data may be utilized, such as in a multi-body inverse dynamics system, to produce a model of the kinematics and/or biomechanics of the patient's knee joint. Such models may allow for adjustment or fine tuning of, for example, the coronal alignment of the relevant tibia and femur, and in particular the position of the tibia relative to the femur in the flexed knee, based on the their specific kinematics. Accordingly, this adjustment or fine tuning may influence the determination of the distal, proximal and/or posterior resection planes in said patient.

Figure 1:
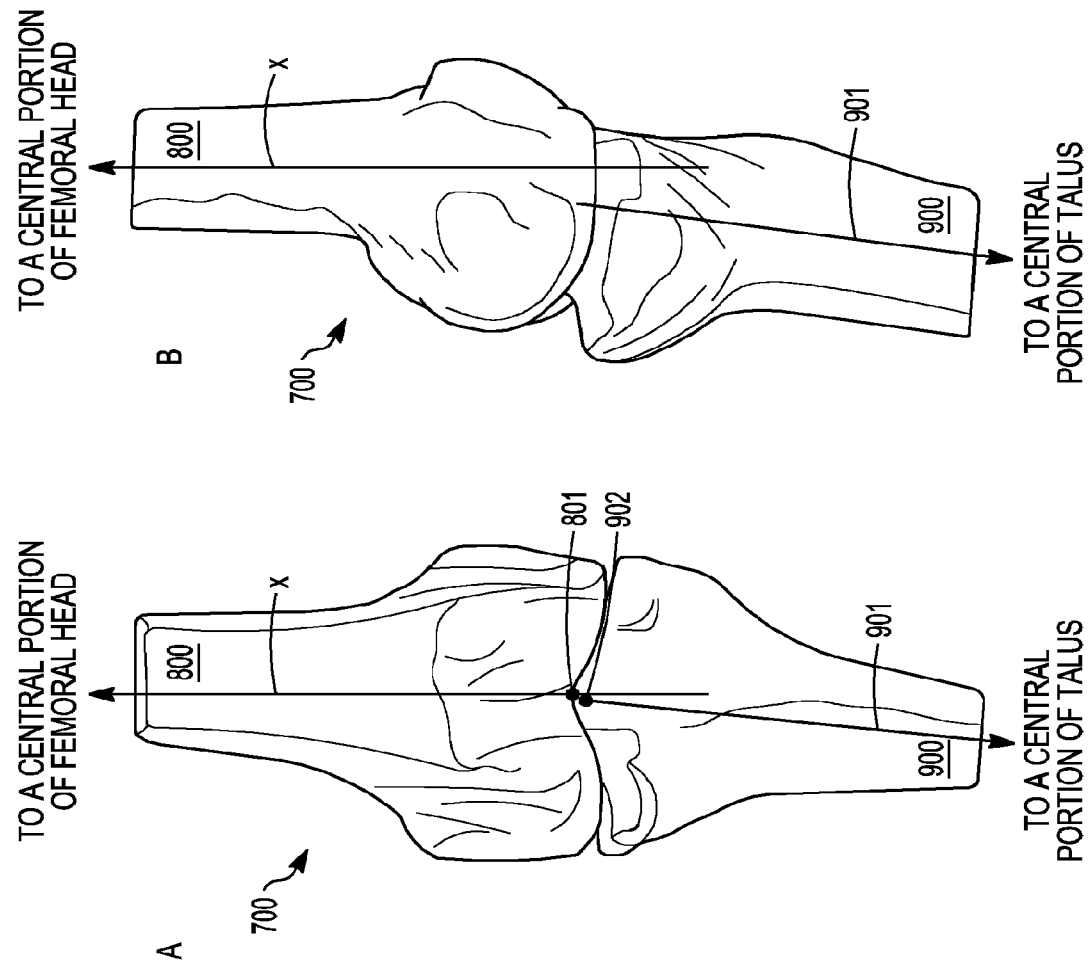
FIG. 1: is a front view (A) and a medial side view (B) of a 3D model of a left knee joint in extension and prior to alignment illustrating some examples of first anatomical indicators and a first alignment axis.

FIGS. 1 to 9 illustrate one embodiment for a method of designing a patient-specific surgical device of the present invention. FIG. 1 demonstrates a front view and a medial side view of an embodiment of a 3D model of a knee joint 700 of a left leg in extension prior to coronal alignment of the tibia 900 and the femur 800 by way of the first alignment axis (x). In the embodiment shown, the first alignment axis (x) is determined by projecting and extending an imaginary vertical line from a central portion of the femoral head (not shown) through a deepest portion of a trochlear groove 801 of the femur 800 (i.e., a femoral mechanical or anatomical axis). A tibial mechanical or anatomical axis 901 is also determined on the 3D model by extending a line from a central portion of the tibial spine 902 to a central portion of the talus (not shown).

Figure 2:
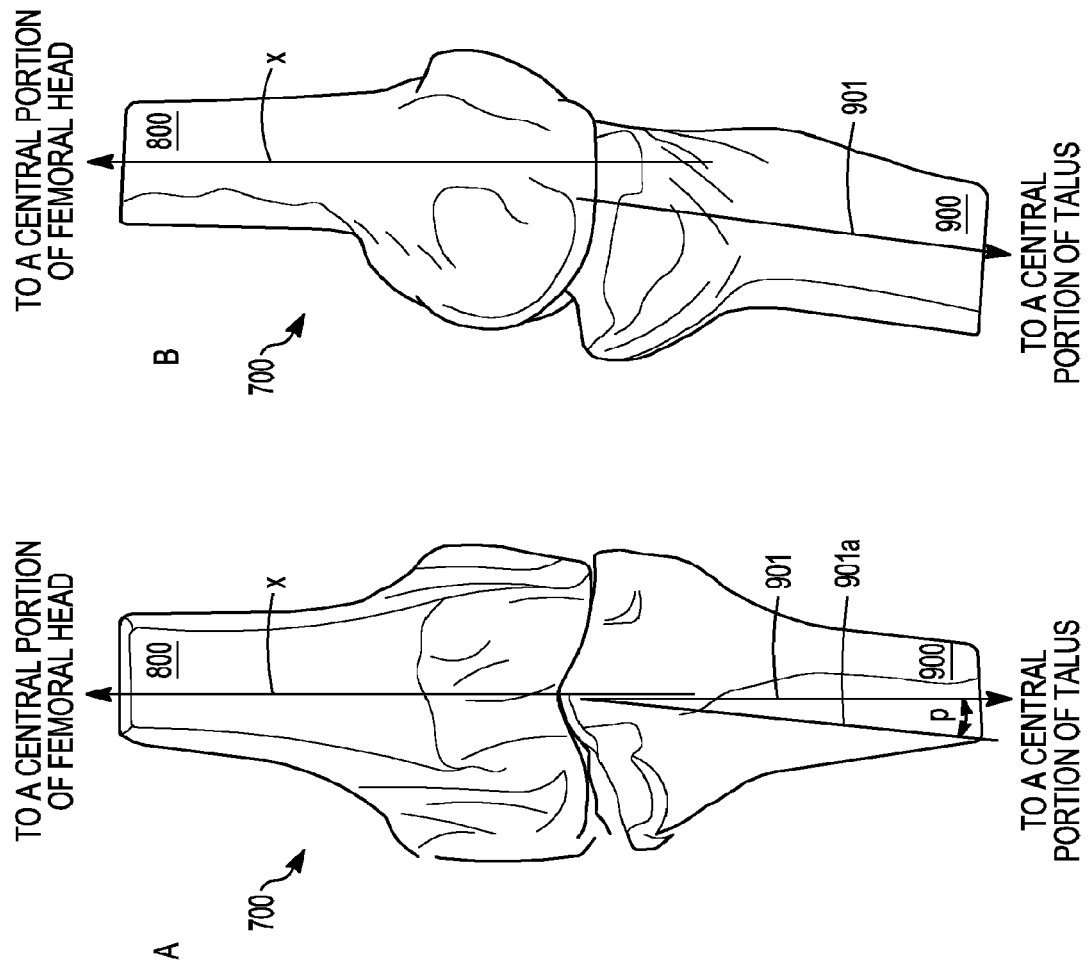
FIG. 2: is a front view (A) and a medial side view (B) of the extended knee joint of the 3D model of FIG. 1 illustrating an example of aligning the tibia with the femur in the coronal plane.

In FIG. 2, the tibia 900 has now been rotated laterally in the coronal plane of the knee joint 700 relative to the femur 800, such that the tibial mechanical axis 901 is substantially parallel or co-axial to the first alignment axis (x) in the coronal plane. The spatial position of the tibial mechanical axis 901 prior to this lateral rotation (denoted as 901a) and the angle of coronal correction (p) are also provided in FIG. 2a. As can be observed from FIGS. 1b and 2b, this coronal alignment of the knee joint 700 in extension is performed with little or no change to the alignment and axial rotation of the tibia 900 relative to the femur 800 when viewed in the sagittal plane.

Although not shown in FIG. 2, alignment of the extended knee joint 700 in the coronal plane may also be performed at least in part by use of the lower limb mechanical axis (not shown) in addition to the tibial and femoral mechanical axes 901 (x). It would be understood, that the lower limb mechanical axis is typically that which extends between the femoral head center and the talus center, as hereinbefore described. To this end, the tibia 900 may be rotated laterally and/or translated in the coronal plane of the knee joint 700 relative to the femur 800, such that the lower limb mechanical axis is substantially parallel or co-axial to the tibial mechanical axis 901 and/or the femoral mechanical axis (x) in the coronal plane. In this regard, any of the lower limb mechanical axis, the tibial mechanical axis and the femoral mechanical axis may serve as the first alignment axis (x). An embodiment of this method of alignment is provided in FIG. 16.

Figure 3:
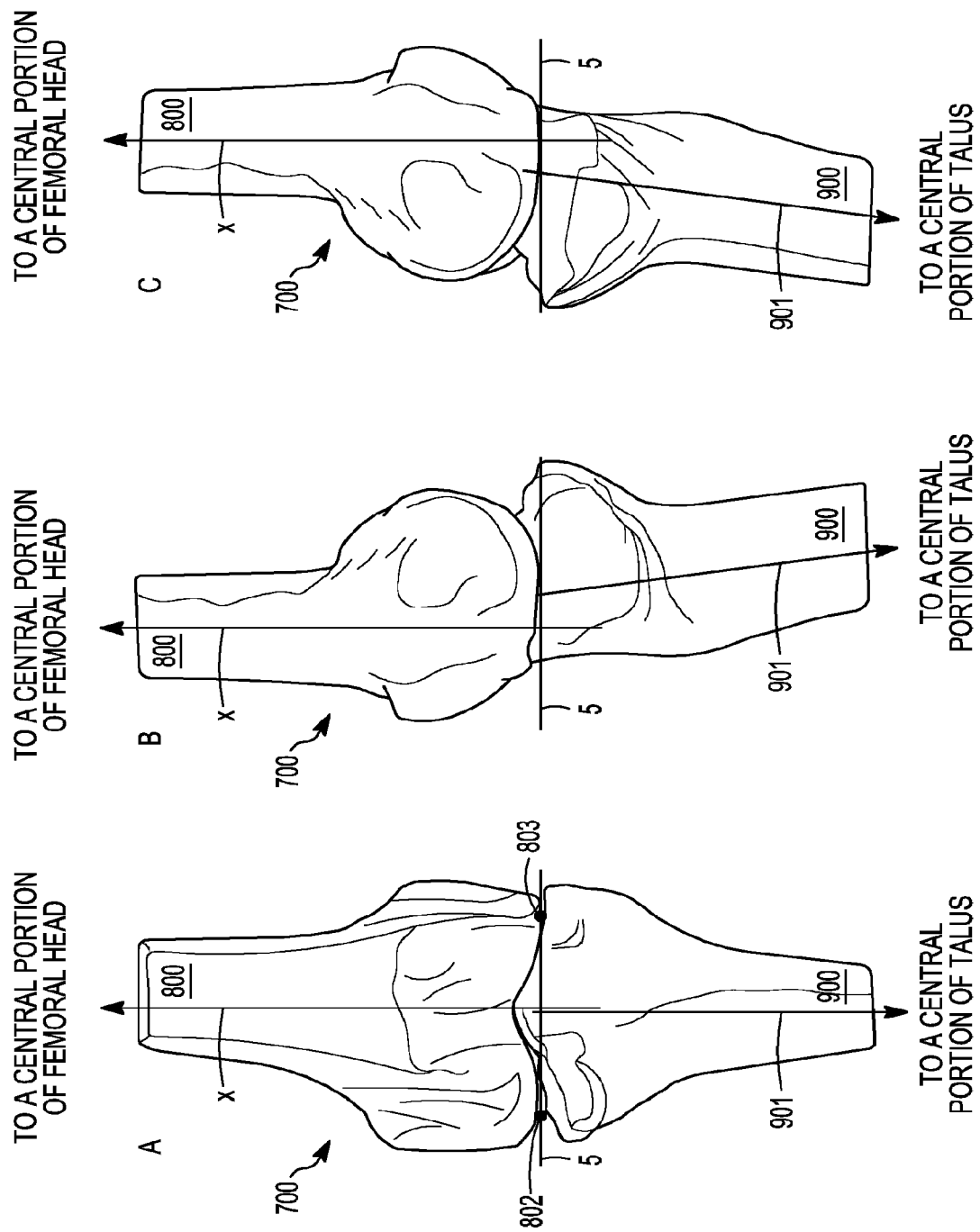
FIG. 3: shows some examples of fourth anatomical indicators and their use in determining a joint line on a front view (A), a lateral side view (B) and a medial side view of the 3D model of FIG. 2.

From FIG. 3, once the femur 800 and the tibia 900 are aligned in the coronal plane a joint line 5 is determined and drawn on the 3D model of the knee joint 700 from one or more anatomical indicators. In the embodiment provided, the joint line 5 is drawn as a line or plane on the 3D model extending between and through a distal portion of the medial condyle 802 and a distal portion of a lateral condyle 803 of the femur 800. Further, the joint line 5 can be observed to be substantially perpendicular to the first alignment axis (x) in both the coronal and sagittal planes of the knee joint 700. The joint line 5 is also shown to be substantially perpendicular to the tibial mechanical axis 901 in the coronal plane of the aligned knee joint 700 in extension.

Figure 4:
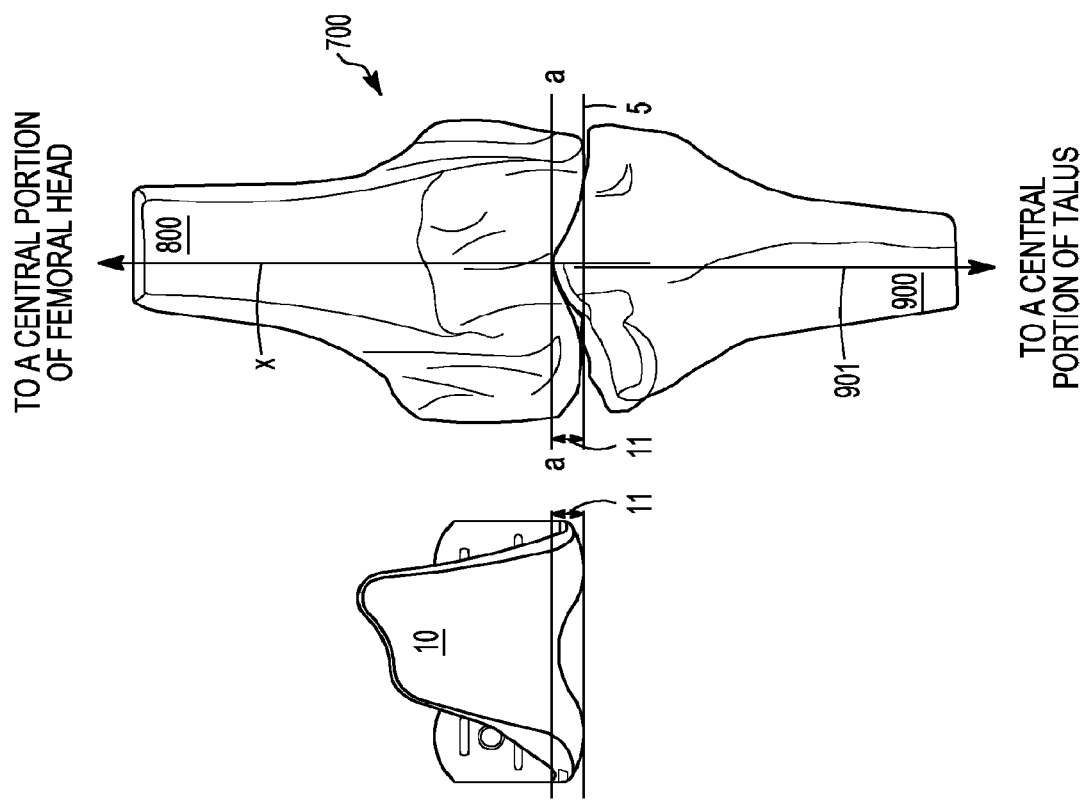
FIG. 4: is a front view of the 3D model of FIG. 3 illustrating an example of determining a distal femoral resection plane from a profile of a femoral prosthesis.

As shown in the embodiment of FIG. 4, a profile or a dimension of a femoral prosthesis 10 to be fitted on the femur 800 is then superimposed on the 3D model of the knee joint 700 in extension. A distal resection plane (a) of the femur 800 is then determined from the 3D model as the distance from the joint line 5 to the distal resection plane (a) equals a first dimension 11 of the femoral prosthesis 10. In the embodiment provided, the first dimension 11 of the femoral prosthesis 10 is the distance between the distal articulation surface of the femoral prosthesis 10 and the distal interface of the femoral prosthesis 10 with the femur 800. In a coronal plane, as can be observed from FIG. 4, the distal resection plane (a) is perpendicular to the first alignment axis (x) and the tibial mechanical axis 901 and substantially parallel to the joint line 5 of the knee joint 700 in extension. Although not shown in FIG. 4, the distal resection plane is also perpendicular to the first alignment axis (x) and substantially parallel to the joint line 5 in the sagittal plane.

Figure 5:
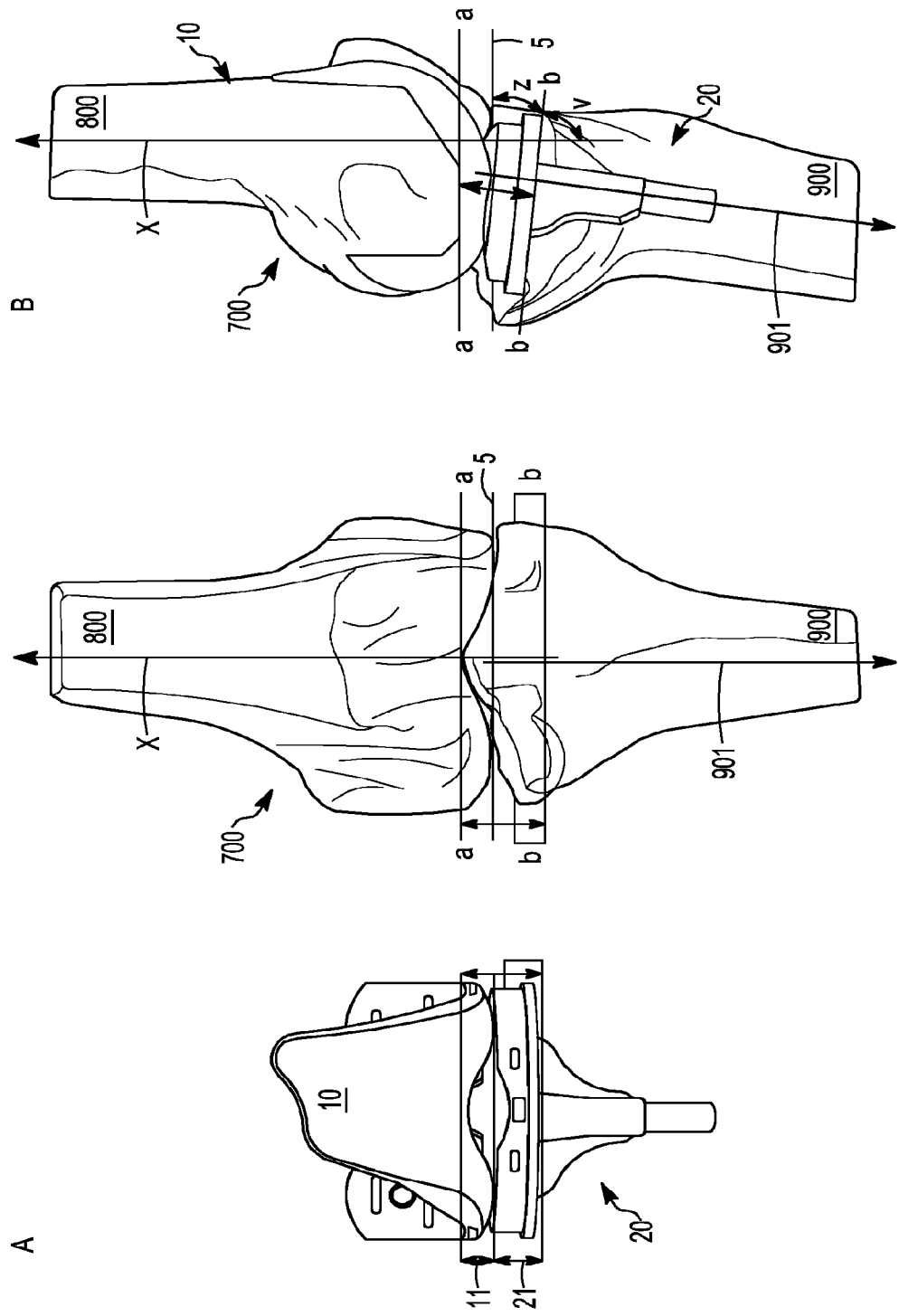
FIG. 5: is a front view (A) and medial side view (B) of the extended knee joint of 3D model of FIG. 4 illustrating an example of determining a proximal tibial resection plane from profiles of a tibial prosthesis and/or a femoral prosthesis.

In FIG. 5, a profile or a dimension of a tibial prosthesis 20 to be fitted on the tibia 900 is then superimposed on the 3D model of the knee joint 700 in extension so as to facilitate determining a proximal resection plane (b) of the tibia 900. In this regard, the proximal resection plane (b) is calculated as that distance from the joint line 5 equal to the first dimension 21 of the tibial prosthesis 20 to be fitted on the tibia 900. As can be seen in FIG. 5b, the tibial prosthesis 10 when suitably fitted on the tibia 900 resides in an antero-posterior slope relative to the joint line 5 and the distal resection plane (a) when viewed in the sagittal plane.

Figure 6:
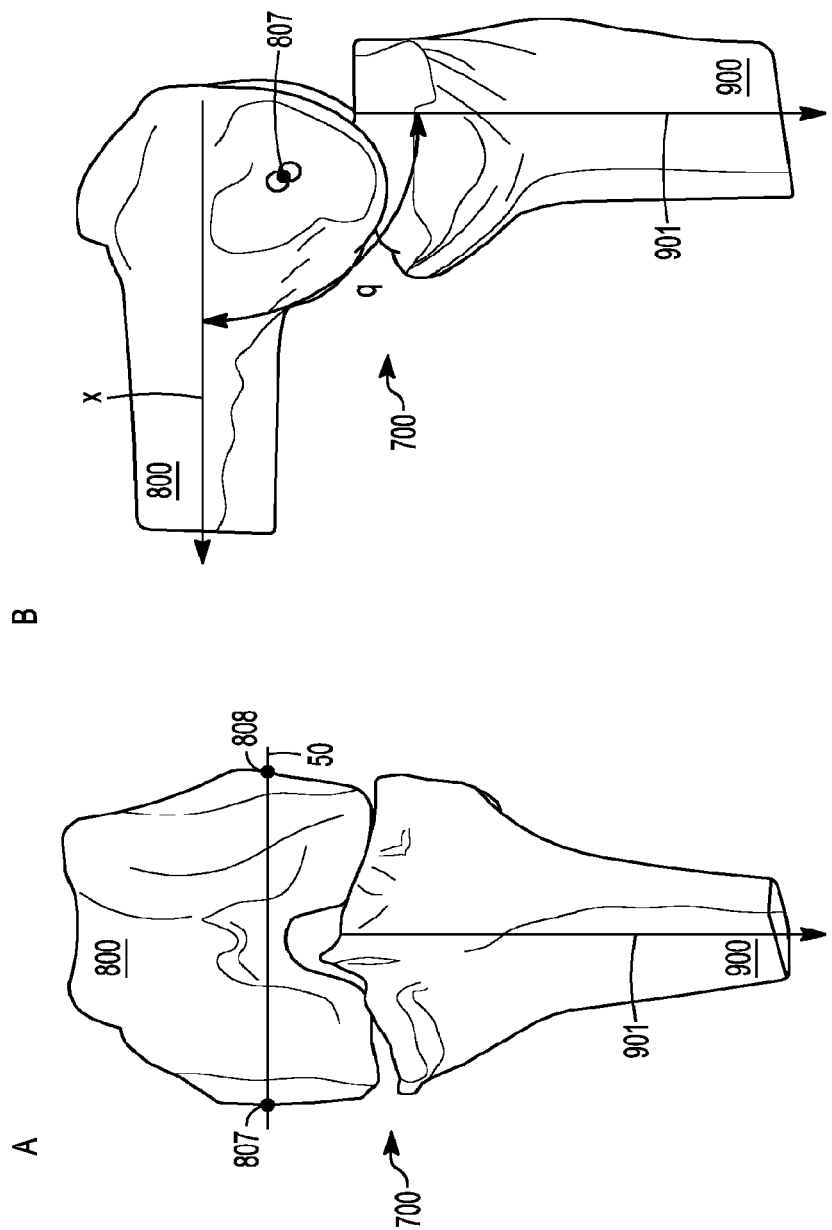
FIG. 6: is a front view (A) and medial side view (B) of the 3D model of FIG. 5 illustrating an example of using a flexion axis to place the knee joint of the 3D model in a flexed position.

Accordingly, the proximal resection plane of the embodiment in FIG. 5 is also determined to be at an angle (z) to the joint line 5 and at an angle (v) to the first alignment axis (x) when viewed in the sagittal plane. The angle (z) is typically between 0 and 15 degrees. Accordingly, the angle (v) is typically between 75 and 90 degrees As illustrated in FIG. 6 and following determination of the distal femoral resection plane (a) and the proximal tibial resection plane (b), the tibia 900 is rotated relative to the femur 800 about a flexion axis 50 so as to provide a 3D model of the knee joint 700 in flexion. Prior to this rotation, the flexion axis 50 is determined on the 3D model of the knee joint 700 by extending a line between a medial condyle arc centre 807 and a lateral condyle arc centre 808. In the embodiment provided, this rotation results in the tibial mechanical axis 901 being substantially perpendicular to the first alignment axis (x) or a femoral mechanical or anatomical axis (not shown) (i.e., angle (q) is approximately 90°).

Figure 7:
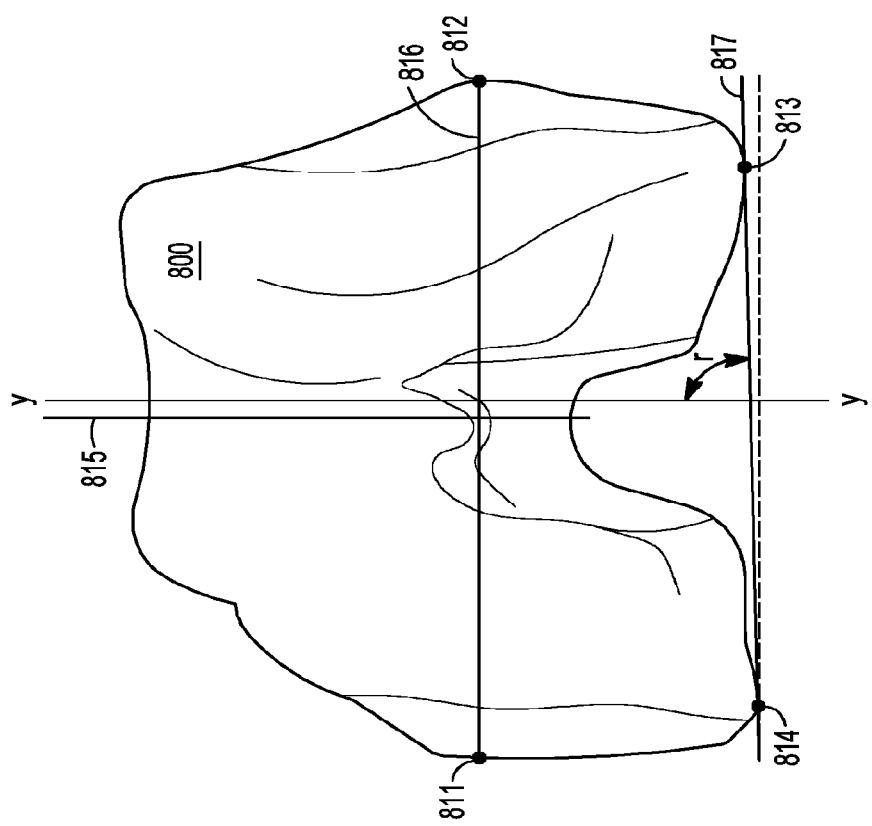
FIG. 7: is a distal end view of the femur of the 3D model of FIG. 6 illustrating some examples of second anatomical indicators and a second alignment axis.

FIG. 7 demonstrates that following placement of the 3D model of the knee joint 700 in a flexed position a second alignment axis (y) is determined from one or a plurality of second anatomical indicators. In the embodiment provided, the transepicondylar axis (TEA) 816 has been drawn on the model, as a line extending between the medial and lateral epicondyles 811, 812 of the femur 800. In addition, a posterior condylar axis 817 extending between posterior portions of the lateral and medial condyles 813, 814 of the femur 800 has been drawn on the 3D model. The second alignment axis (y) can then be determined on the 3D model of the knee joint 700 in flexion from these second anatomical indicators.

In the embodiment provided, the second alignment axis (y) is substantially parallel to the anteroposterior axis 815, is substantially perpendicular to the TEA 816 and is at an angle (r) to the posterior condylar axis 817. As would be appreciated, only one of the anteroposterior axis 815, the TEA 816 and the posterior condylar axis 817 may be determined so as to facilitate calculating the second alignment axis (y). Two or more of these axes, however, may be used to improve a user's accuracy in calculating the second alignment axis (y) on the 3D model of the knee joint 700 in flexion.

Figure 8:
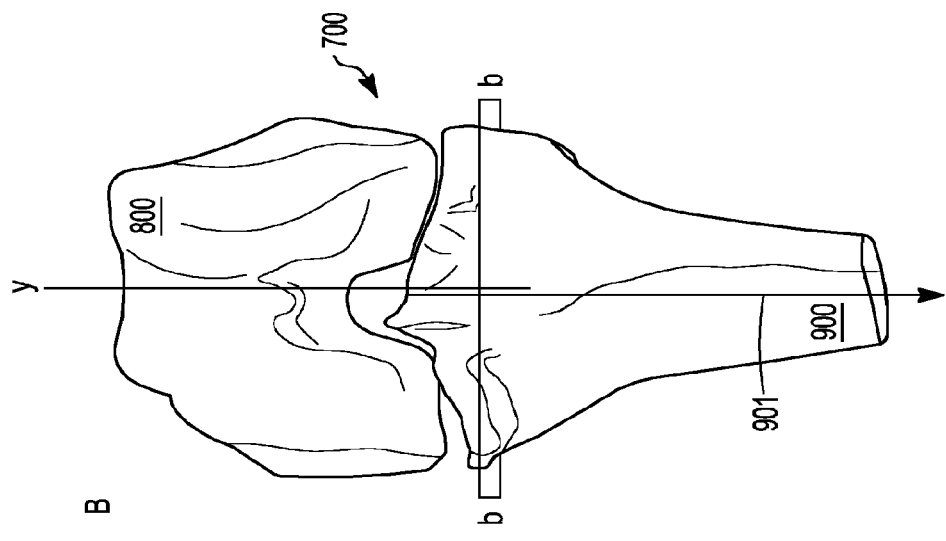
FIG. 8: is a front view of the flexed knee joint of the 3D model of FIG. 7 prior to alignment (A) and a front view of this flexed knee joint illustrating an example of aligning the tibia with the femur in the coronal plane (B).
Figure 8:
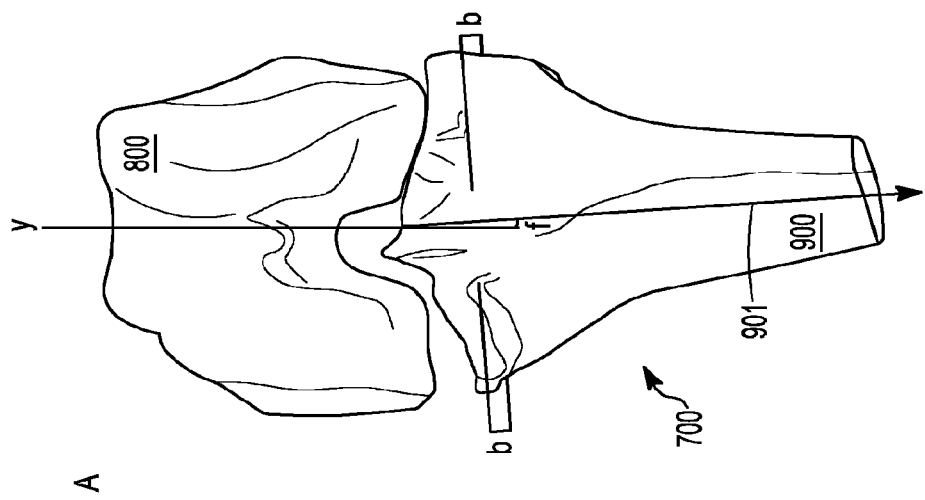

In FIG. 8 and following determination of the second alignment axis (y), coronal alignment of the tibia 900 relative to the femur 800 has been performed on the 3D model of the knee joint 700 in flexion. As can be observed in FIG. 8a, the tibial mechanical axis 901 is at an angle (f) relative to the second alignment axis (y) prior to coronal alignment of the knee joint 700 in flexion. In FIG. 8b, the tibia 900 has now been rotated medially by an amount equal to the angle (f) in a coronal plane, such that the tibial mechanical axis 901 is now substantially parallel to the second alignment axis (y) on the 3D model. Further, in FIG. 8b the proximal resection plane (b) is now substantially perpendicular to the second alignment axis (y) when viewed in a coronal plane.

Figure 9:
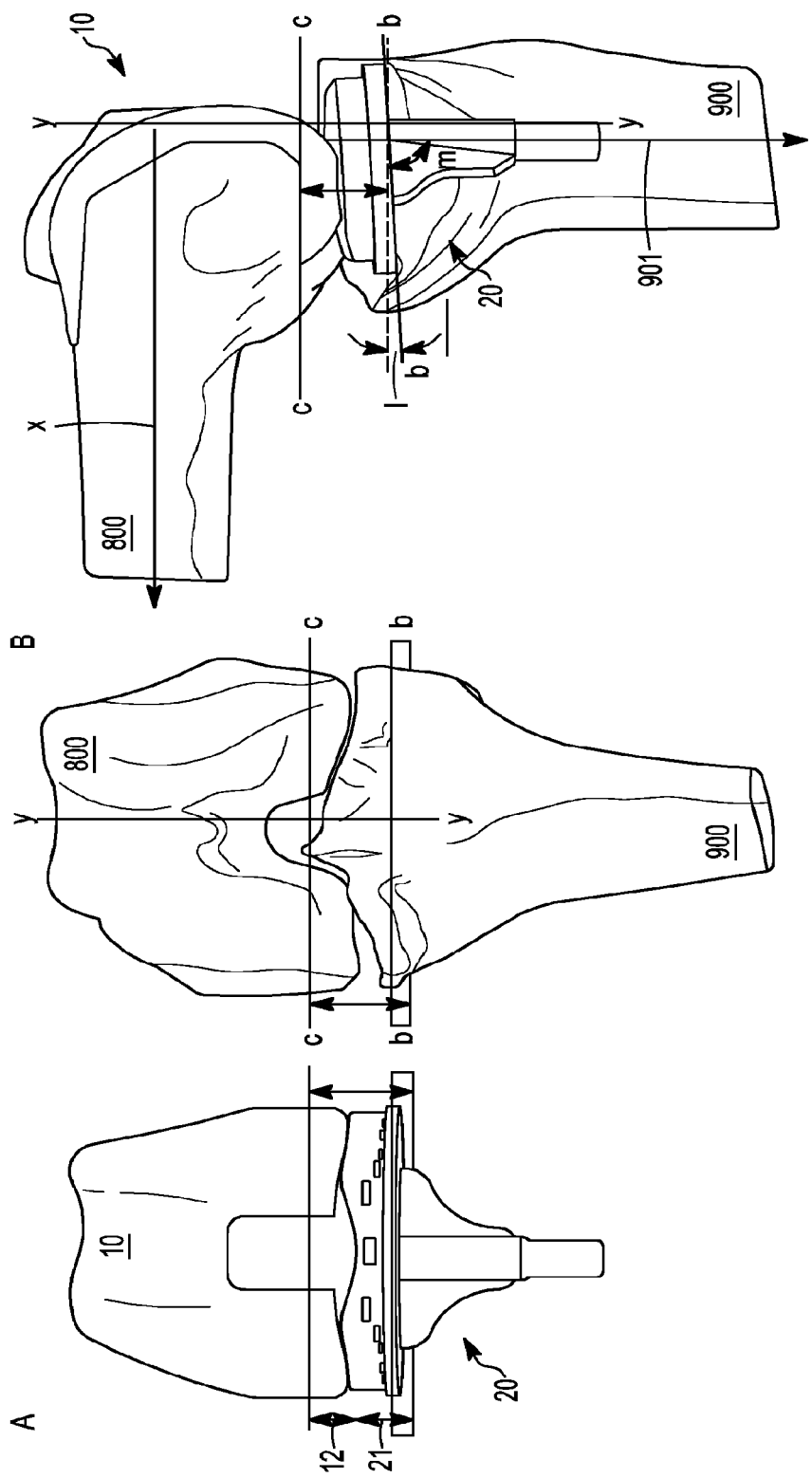

As shown in FIG. 9, a profile of the femoral prosthesis 10 and a profile of the tibial prosthesis 20 are then superimposed on the 3D model of the knee joint 700 in flexion so as to facilitate determining a posterior resection plane (c). To this end, FIG. 9 illustrates that the posterior resection plane (c) has been calculated as that distance from the proximal resection plane (b) equal to the sum of a second dimension 12 of the femoral prosthesis 10 and the first dimension 21 of the tibial prosthesis 20. In the embodiment provided, the second dimension 12 of the femoral prosthesis 10 is the distance between the posterior articulation surface of the femoral prosthesis 10 and the posterior interface of the femoral prosthesis 10 with the femur 800.

As can be seen in FIG. 9b, when suitably fitted on the tibia 900 of the flexed knee joint 700, the tibial prosthesis 10 resides in an anteroposterior slope relative to the posterior resection plane (c) and the second alignment axis (y) (not shown) when viewed in the sagittal plane. Accordingly, the posterior resection plane of the embodiment in FIG. 9 is also determined to be at an angle (l) relative to the proximal resection line (b) and at an angle (m) relative to the tibial mechanical axis 901 and the second alignment axis (y) (not shown) when viewed in the sagittal plane. The angle (l) is typically between 0 and 15 degrees. Accordingly, the angle (m) is typically between 75 and 90 degrees.

Once the patient-specific distal, proximal and/or posterior resection planes have been determined, a patient-specific or customised surgical device may be created and provided.

The patient-specific surgical device preferably conforms in some way to a patient's bone and is generally specific to said patient. For example, the bone-contacting or -engaging surfaces of the patient-specific surgical device may comprise one or more portions or surfaces having mirrored contours of a patient's bone thereon, or the bone-contacting or -engaging surfaces may comprise a few suitably located contact points that reversibly lock the patient-specific surgical device on the patient's bone. In addition, the patient-specific surgical device may comprise one or more means, such as a fixation aperture adapted to receive a fastening member therethrough, so as to facilitate reversible fixation of the device to the patient's bone.

In particular embodiments, the patient-specific surgical device comprises one or a plurality of means, such as resection apertures or slots, for guiding a resection or cutting tool along the distal resection plane, the proximal resection plane and/or the posterior resection plane. Accordingly, the patient-specific surgical devices themselves may function as patient-specific distal femoral, proximal tibial and/or anteroposterior femoral resection members with the resection apertures or slots positioned therein via, at least in part, the methods of designing a patient-specific surgical device described herein rather than previous positioning algorithms.

In other embodiments, the patient-specific surgical device comprise one or a plurality of guide apertures, which indicate or correlate to desired surgical alignments by, for example, inserting alignment pins. In this regard, the alignment pins are inserted along the trajectories defined by the guide apertures, after which the patient-specific surgical device is removed from the knee leaving the alignment pins in place. Alternatively, holes can be drilled in a patient's bone through the guide apertures and alignment pins, posts, or other components can be aligned relative to the holes after the patient-specific surgical device has been removed. The alignment pins can subsequently orient a resection member, for example, by sliding said resection member thereon. When suitably attached to the alignment pins, the resection member preferably comprises one or a plurality of resection apertures for guiding a resection or cutting tool along the distal resection plane, the proximal resection plane and/or the posterior resection plane.

As would be understood by the skilled artisan, in embodiments of the present invention wherein one or a plurality of guide apertures facilitate the positioning of a resection member, the position and orientation (e.g., angle relative to the bone) of these guide apertures, and hence alignment pins received therethrough, may be influenced or determined by the particular type of resection member to be used by the surgeon.

In order to facilitate the positioning of a resection member, the position and orientation of these guide apertures may first facilitate the positioning of an alignment device on the knee joint, such as that described in WO2012/024306. In this regard, the alignment device may engage the tibia and/or femur directly or indirectly, such as by way of a resection member, so as to provide surgical alignment of the bony resections required relative to those of the tibia and/or femur while the knee joint is in extension or flexion. For example, the alignment device can be shaped so as to engage the cutting slot of a distal femoral resection member. Once engaged with said distal femoral resection member, the alignment device may include slots or apertures for aligning the proximal resection of the tibia with the distal resection of the femur in a coronal plane whilst the knee joint is in extension. The alignment device may further define guide apertures or slots through which alignment pins for the placement of a resection member thereon may be inserted.

Preferably, the patient-specific surgical device provided herein comprises a spacer for insertion between the femur and tibia to at least partly facilitate return of the knee joint to an appropriate alignment with the first and/or second alignment axis and/or an appropriate soft tissue balance. The spacer of the device is typically customized and/or predetermined according to the patient-specific anatomical data. In this regard, a spacer may extend to either the lateral or medial sides of the knee joint or both. This would depend upon the individual's preoperative knee anatomy as determined by, for example, magnetic resonance imaging (MRI) or computed tomography (CT), and the presence of any anatomical deformities and/or defects, such as varus or valgus. By way of example, the skilled artisan would readily recognise that a knee demonstrating varus deformity may require a spacer placed only medially in the joint to achieve a desired joint alignment and/or soft tissue balancing. As such, the position, size and shape of the spacer are not to be limited to any particular knee defect and/or deformity.

In particular embodiments, the spacer may extend into the joint space between the femur and the tibia, for example, substantially to the center of the joint space along an anterior-posterior direction. The spacer may extend a greater or lesser distance into the joint space, and may extend completely through the joint space. In certain embodiments, the shape of the spacer preferably allows for the presence of unresected anterior and/or posterior cruciate ligaments within the knee joint.

The spacer may optionally include and upper surface that is patient-matched to conform to a distal surface of the femur, such as a distal condylar surface. Additionally, the spacer may include a lower surface that is patient-matched to conform to a proximal surface of the tibia, such as the proximal tibial plateau. Engagement of one or more of the patient-matched surfaces to the knee can contribute further stability, such as rotational and/or anteroposterior stability, to the engagement of the patient-specific surgical device to the knee.

Figure 14:
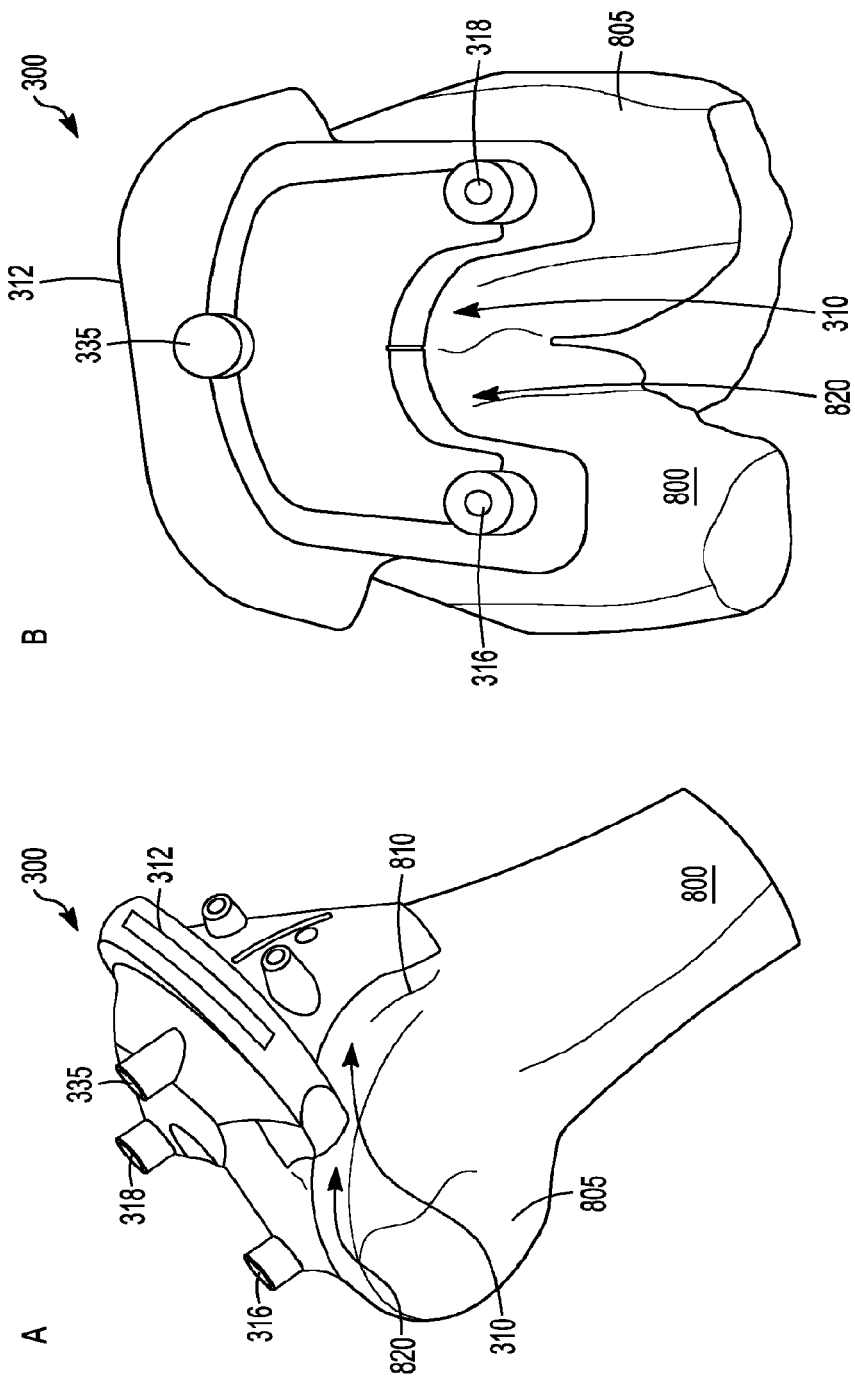
FIG. 14: shows a distal end perspective view (A) and a distal end view of a femur having thereon an embodiment of a patient-specific surgical device.
Figure 15:
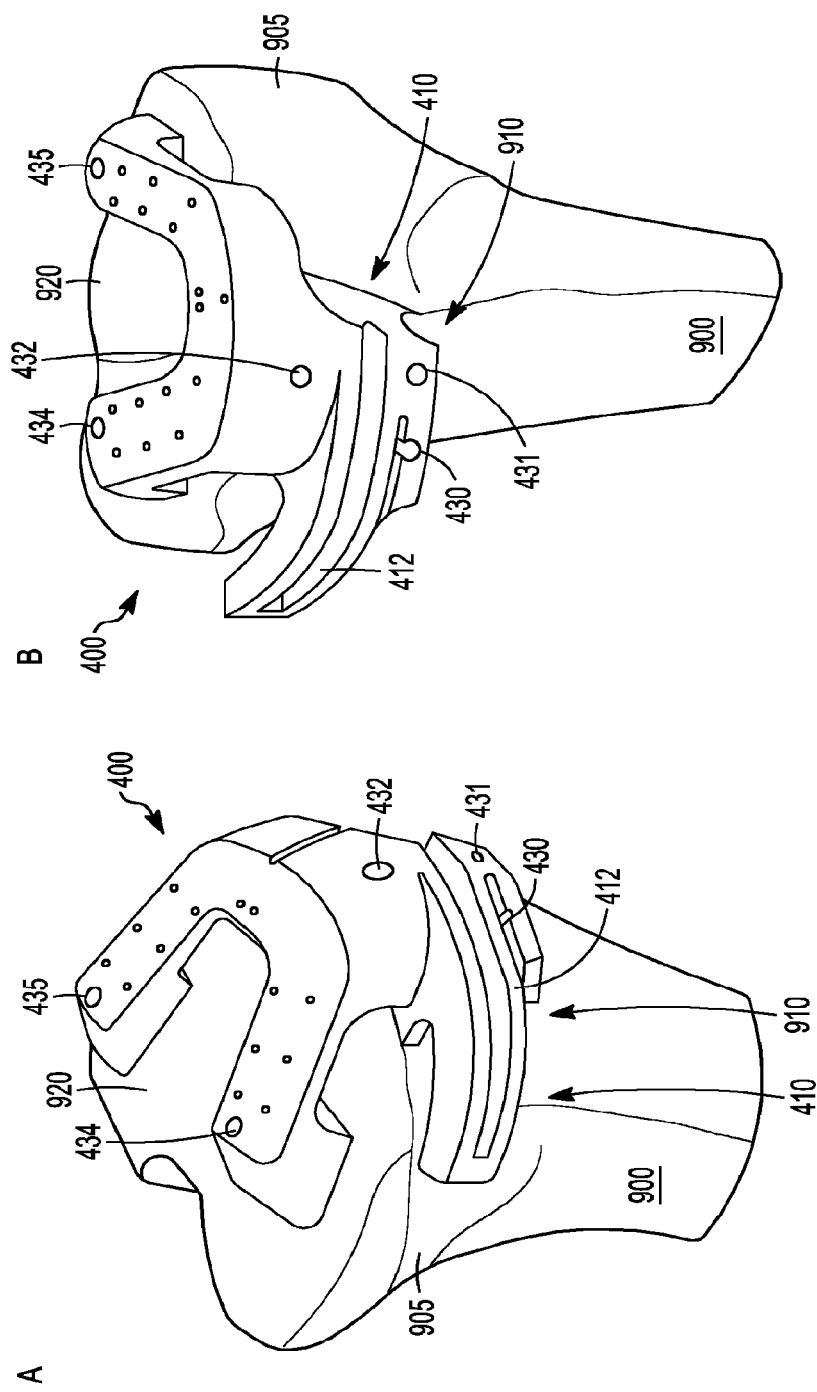
FIG. 15: shows a proximal end perspective view (A) and a proximal end view of a tibia having thereon an embodiment of a patient-specific surgical device.

It would also be appreciated that the spacer to be designed on the 3D model of the knee joint may be only virtual in nature and not constitute part of the final design of the patient specific surgical device. Accordingly, separate patient specific surgical devices for the femur and/or tibia may be manufactured by the design method described herein that do not include a spacer (see, for example, the embodiments of patient specific surgical devices in FIGS. 14 and 15). Such patient specific surgical devices, however, would allow for appropriate soft tissue balancing and knee joint alignment despite the absence of the spacer, as the position of the required resection plane/s have typically been determined after such balancing and alignment on the 3D model of the patient's knee joint. Further, a spacer may not be required regardless of whether the patient specific surgical device has been designed for directly resecting the femur and/or tibia or facilitating positioning of a resection member on the femur and/or tibia.

In certain embodiments, the patient-specific surgical device is designed so as to facilitate, at least partly, return of the knee to an appropriate and/or balanced soft tissue tension when in extension and/or flexion. Balanced soft tissue tension requires placing the soft tissues surrounding and/or interconnecting the bones of the knee, such as that of the medial and lateral knee, at an approximately equal or similar tension relative to one another when the femur and its corresponding tibia are placed in a desired alignment as determined by the surgeon. Preferably, an appropriate soft tissue tension is approximately equal or similar to the physiological tension of these soft tissues in the native knee at rest. In this regard, a patient's soft tissue tension may be compared to that of a control or reference sample or population. Non-limiting examples of the soft tissues surrounding and/or interconnecting the bones of the knee include the medial and lateral collateral ligaments, the anterior and posterior cruciate ligaments, the posteromedial and posterolateral ligamentous structures and the posterior capsule. It would be appreciated that the present invention is not to be limited to any particular means of measuring soft tissue tension of the knee, which may include, for example, an arthrometer, a dynamometer, radiography, MRI, computer assisted surgery and a knee joint tension meter.

For the purposes of the present invention, such appropriate and/or balanced soft tissue tensioning may be achieved during and/or after surgery. Further, an appropriate and/or balanced soft tissue tension may be transient in nature.

In particular embodiments, with respect to an appropriate soft tissue tension, medial and/or lateral soft tissue laxity of the knee in flexion and/or extension is about 1° to about 7.0°. In particular embodiments of the present invention, the medial and/or lateral soft tissue laxity of the knee in flexion and/or extension is about 1.0°, 1.1°, 1.2°, 1.3°, 1.4°, 1.5°, 1.6°, 1.7°, 1.8°, 1.9°, 2.0°, 2.1°, 2.2°, 2.3°, 2.4°, 2.5°, 2.6°, 2.7°, 2.8°, 2.9°, 3.0°, 3.1°, 3.2°, 3.3°, 3.4°, 3.5°, 3.6°, 3.7°, 3.8°, 3.9°, 4.0°, 4.1°, 4.2°, 4.3°, 4.4°, 4.5°, 4.6°, 4.7°, 4.8°, 4.9°, 5.0°, 5.1°, 5.2°, 5.3°, 5.4°, 5.5°, 5.6°, 5.7°, 5.8°, 5.9°, 6.0°, 6.1°, 6.20, 6.3°, 6.4°, 6.5°, 6.6°, 6.7°, 6.8°, 6.9°, 7.0°, or any range therein. As would be appreciated by the skilled artisan, this measurement of medial and/or lateral soft tissue laxity may vary according to the means used to measure such laxity.

In certain embodiments, with respect to a balanced soft tissue tension, the difference between medial and lateral soft tissue laxity of the knee in flexion and/or extension is equal to or less than about 5°. In particular embodiments of the present invention, the difference between medial and lateral soft tissue laxity of the knee is about 0°, 0.1°, 0.2°, 0.3°, 0.4°, 0.5°, 0.6°, 0.7°, 0.8°, 0.9°, 1.0°, 1.1°, 1.2°, 1.3°, 1.4°, 1.50, 1.6°, 1.7°, 1.8°, 1.9°, 2.0°, 2.1°, 2.2°, 2.3°, 2.4°, 2.5°, 2.6°, 2.7°, 2.8°, 2.9°, 3.0°, 3.1°, 3.2°, 3.3°, 3.4°3.5°, 3.6°, 3.7°, 3.8°, 3.9°, 4.0°, 4.1°, 4.2°, 4.3°, 4.4°, 4.5°, 4.6°, 4.7°, 4.8°, 4.9°, 5.0°, or any range therein. Such soft tissue laxity of the knee may be measured by any means known in the art, such as those hereinbefore described.

Figure 10:
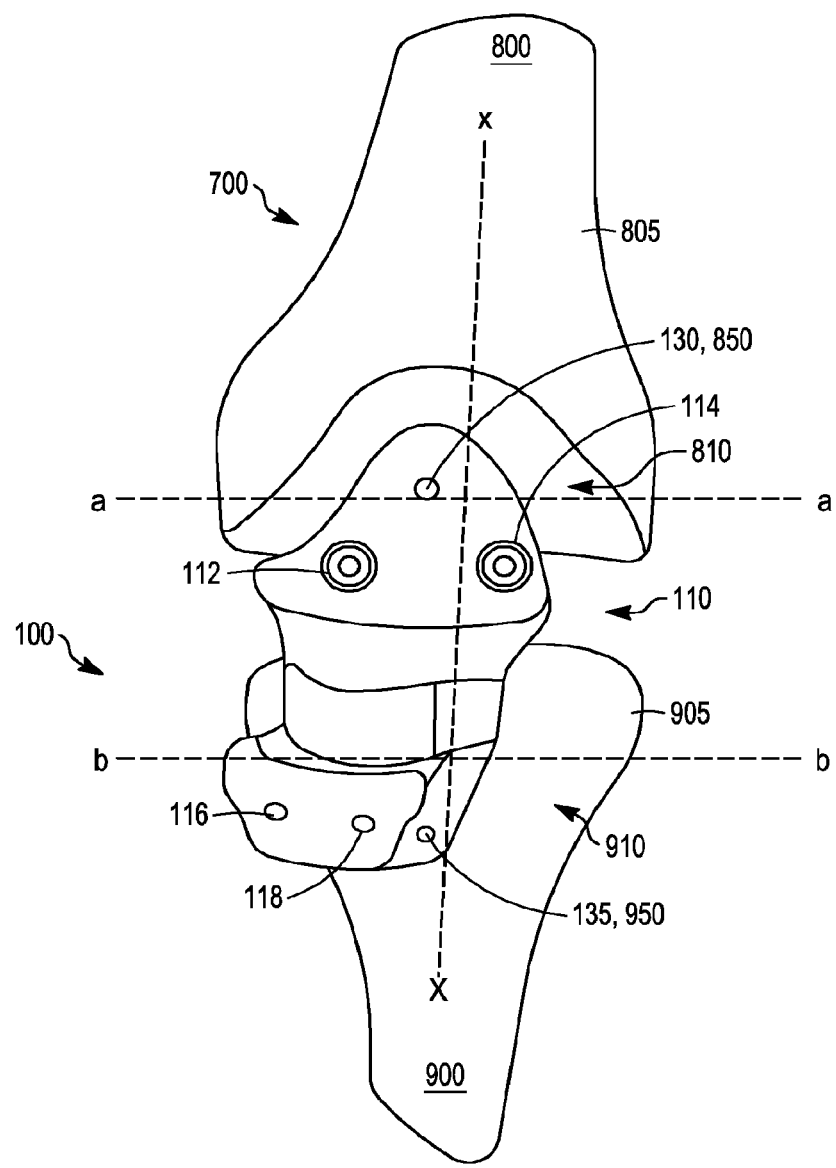
FIG. 10: shows a front view of an embodiment of the device according to one aspect of the invention as applied to a left knee joint in extension.
Figure 11:
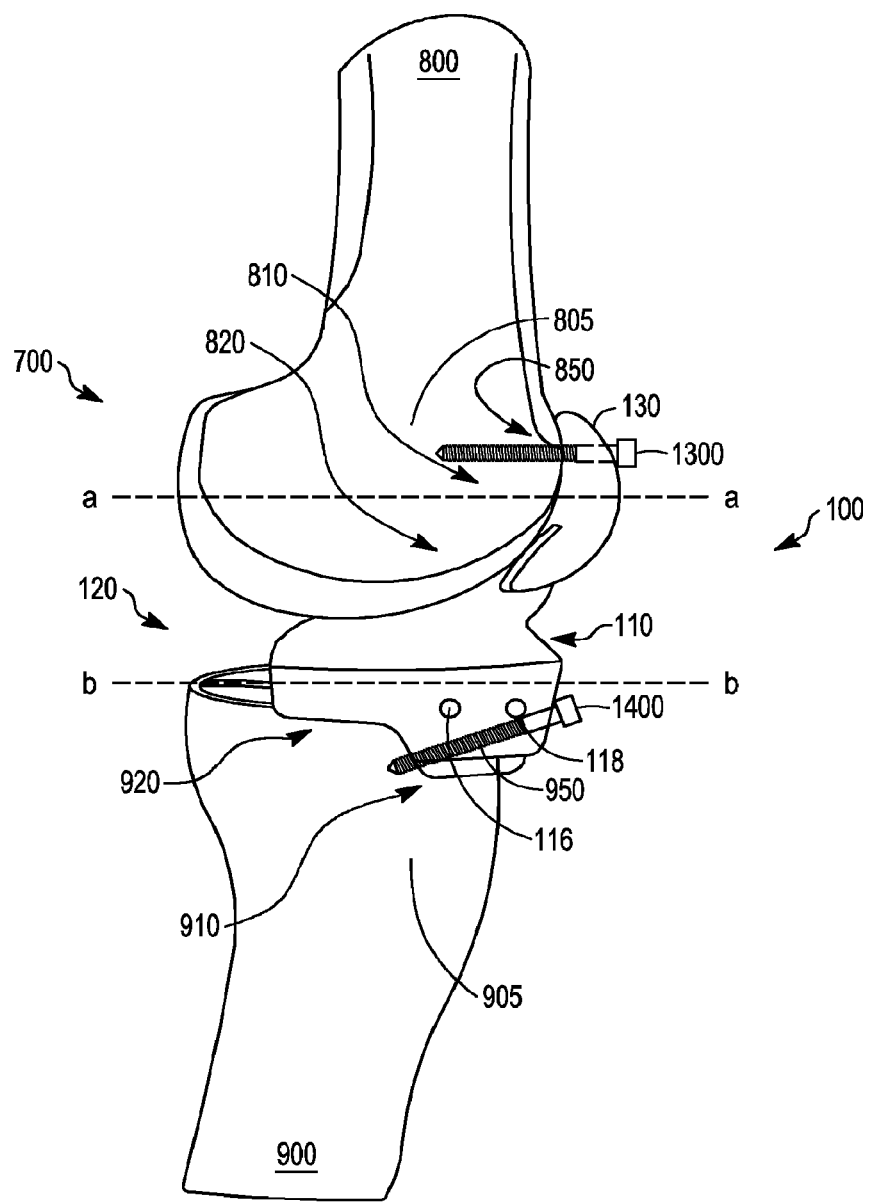
FIG. 11: shows a side view of the device of FIG. 10 following fastening to the femur and tibia.

FIGS. 10 and 11 show one embodiment of a patient-specific surgical device 100 designed by the method hereinbefore described to be used when the knee joint 700 is in extension. The patient specific device 100 comprises an engaging portion 110 adapted to engage one or more anterior surfaces 810 of a distal portion 805 of the femur 800 and one or more anterior surfaces 910 of a proximal portion 905 of the tibia 900. The device 100 further comprises a spacer 120, which engages one or more articular surfaces 820 of a distal portion 805 of the femur 800 and one or more articular surfaces 920 of a proximal portion 905 of the tibia 900. In this regard, the spacer 120 is adapted to at least partly align in a coronal axis the tibia 900 and/or the femur 800 with a first alignment axis (x). In the embodiment shown, the spacer 120 is integral with the engaging portion 110 of the device 100.

In addition, the device 100 comprises guide apertures 112 and 114 for facilitating the placement of one or more alignment pins or markers so as to facilitate resection of the femur 800 along a distal resection plane (a). In this regard, these alignment pins or markers are subsequently used to facilitate positioning of a distal femoral resection member on the femur 800. After positioning or placement of the distal femoral resection member on the alignment pins or markers, the femur 800 may be subsequently resected by way of resection apertures in the distal femoral resection member that guide a resection tool along the distal resection plane (a).

As seen in FIGS. 10 and 11, the device 100 further includes guide apertures 116 and 118 for facilitating the placement of one or more alignment pins or markers so as to facilitate resection of the tibia 900 along a proximal resection plane (b). Following their placement, a proximal tibial resection member can now be positioned or oriented on the tibia 900 by way of sliding the resection member onto these alignment pins or marks. After positioning or placement of the proximal tibial resection member on the alignment pins or markers, the tibia 900 may be subsequently resected by way of resection apertures in the proximal tibial resection member that guide a resection tool along the proximal resection plane (b).

The embodiment of the device 100 shown in FIGS. 10 and 11 further comprises fixation apertures 130 and 135 for receiving fastening members 1300 and 1400 respectively therethrough into femoral and tibial holes 850 and 950 respectively so as to facilitate reversible fixation of the device 100 to the knee joint 700.

Figure 12:
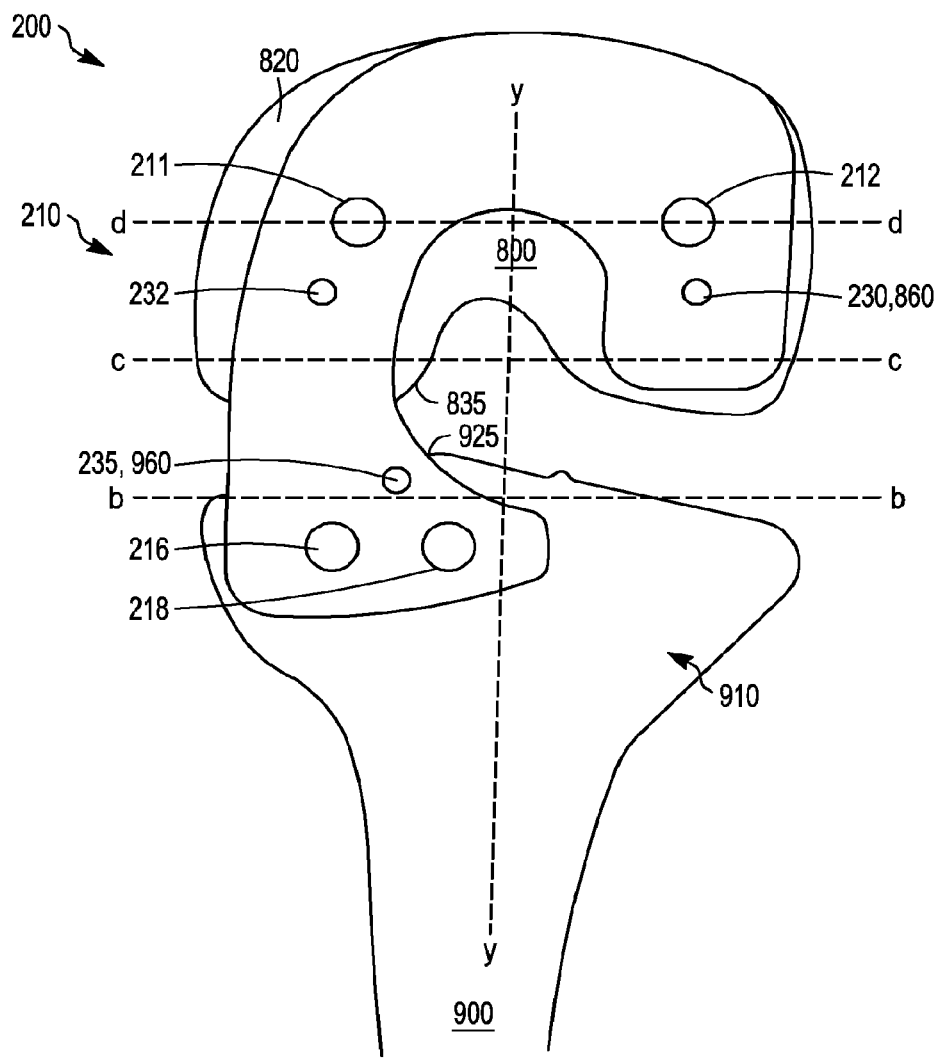
FIG. 12: shows a front view of an embodiment of the device according to one aspect of the invention as applied to the left knee joint in flexion.
Figure 13:
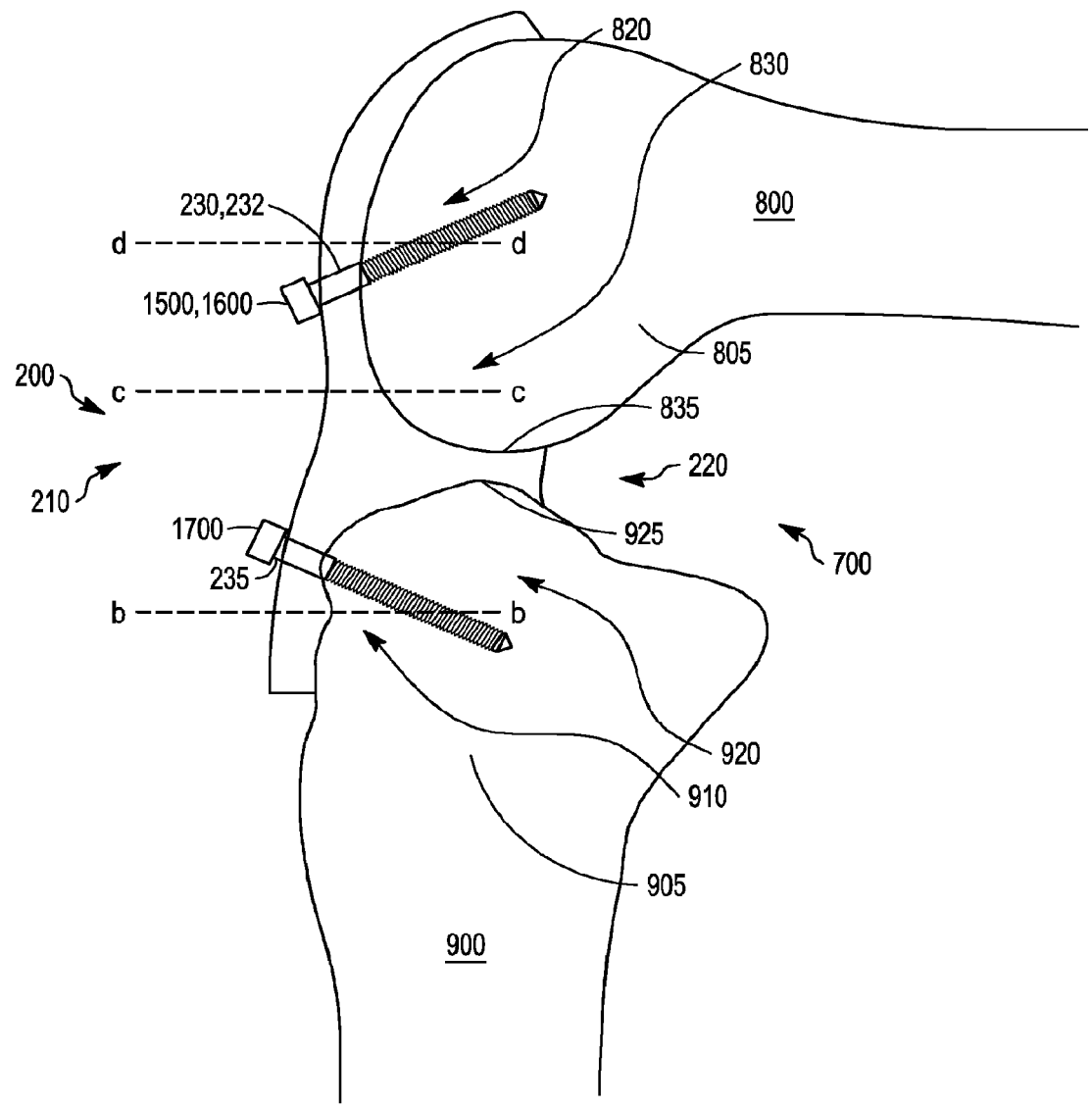
FIG. 13: shows a side view of the device of FIG. 12 following fastening to the femur and tibia.

FIGS. 12 and 13 demonstrate an embodiment of a device 200 designed by the method hereinbefore described to be used when the knee joint 700 is in flexion. The device 200 comprises an engaging portion 210 adapted to engage one or more articular surfaces 820 of a distal portion 805 of the femur 800 and one or more anterior surfaces 910 of a proximal portion 905 of the tibia 900. The device 200 further comprises a spacer 220, which engages one or more articular surfaces 820 and/or posterior surfaces 830 of a distal portion 805 of the femur 800 and one or more articular surfaces 920 of a proximal portion 905 of the tibia 900. In the embodiment shown, the spacer 220 is engaging the medial articular surfaces 835, 925 of the distal portion 805 of the femur 800 and the proximal portion 905 of the tibia 900 respectively. Further, the spacer 120 is adapted to at least partly align in a coronal axis the tibia 900 and/or the femur 800 with a second alignment axis (y). Similar to that for the device 100, the spacer 220 is integral with the engaging portion 210 of the device 200.

The device 200 comprises guide apertures 211 and 212 for facilitating the placement of one or more alignment pins or markers in the femur so as to facilitate resection of the femur 800 along a posterior resection plane (c). To this end, these alignment pins or markers are subsequently used to facilitate positioning or orientation of an anteroposterior femoral resection member on the femur 800, typically by sliding the resection member thereon. After positioning or placement of the anteroposterior femoral resection member on the alignment pins or markers, the femur 800 may be subsequently resected by way of resection apertures in the anteroposterior femoral resection member that guide a resection tool along the posterior resection plane (c). Furthermore, the guide apertures 211 and 212 of the embodiment of the device in FIG. 12 also mark the transepicondylar axis (TEA) (d) of the femur 800.

The device 200 further includes guide apertures 216 and 218, which, similar to that for guide apertures 116, 118 of the device 100, facilitate the placement or marking of one or more alignment pins or markers for facilitating resection of the tibia 900 along the proximal resection plane (b).

The embodiment of the device 200 shown in FIGS. 12 and 13 further comprises apertures 230, 232 and 235 for receiving fastening members 1500, 1600 and 1700 respectively therethrough into femoral and tibial holes 860 and 960 respectively so as to facilitate reversible fixation of the device 200 to the knee joint 700.

FIGS. 14A and 14B illustrate a further embodiment of a patient-specific surgical device 300 designed by the method hereinbefore described to be engaged with the femur 800. The patient-specific surgical device 300 comprises an engaging portion 310 adapted to engage one or more anterior surfaces 810 and articular surfaces 820 of a distal portion 805 of the femur 800.

The device 300 further comprises a resection aperture 312 for guiding a resection tool along a distal femoral resection plane (not shown). In this regard, the distal resection plane has been determined by that design method hereinbefore described. Additionally, the device 300 includes guide apertures 316 and 318 for facilitating the placement of one or more alignment pins or markers so as to assist in marking the transepicondylar axis of the femur 800 for subsequent placement or positioning of a anteroposterior femoral resection member thereon to perform the anterior and/or posterior femoral resections.

As shown in FIGS. 14A and 14B device 300 further comprises fixation apertures 330 and 335 for receiving fastening members therethrough so as to facilitate reversible fixation of the device 300 to the femur 800.

FIGS. 15A and 15B illustrate a further embodiment of a patient-specific surgical device 400 designed by the method hereinbefore described to be engaged with the tibia 900. The patient-specific surgical device 400 comprises an engaging portion 410 adapted to engage one or more anterior surfaces 910 and articular surfaces 920 of a proximal portion 905 of the tibia 900.

As illustrated in FIGS. 15A and 15B, the device 400 includes a resection aperture 412 for guiding a resection tool along a proximal tibial resection plane (not shown), which has been determined by that design method hereinbefore described. The device 400 further comprises fixation apertures 430, 431, 434, 434 and 435 for receiving fastening members therethrough so as to facilitate reversible fixation of the device 400 to the tibia 900. The fixation apertures 430, 431 and 431, 432 may further function to produce pinholes or markings on the superior surface of the tibia 900 so as to facilitate marking the anteroposterior and mediolateral position respectively of the tibia 900 relative to the femur 800. Similarly, fixation apertures 434 and 435 may also function to facilitate marking axial rotation of the tibia 900 relative to the femur 800.

As would be readily understood by the skilled artisan, the dimensions for the device of the third aspect as well as the relative positions of the guide apertures and/or resection apertures therein will depend to some degree on the size of the knee joint to which the devices are to be applied.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

The following non-limiting examples illustrate the patient-specific surgical devices and methods of the invention. These examples should not be construed as limiting: the examples are included for the purposes of illustration only. The patient-specific surgical devices and methods discussed in the Examples 1-4 will be understood to represent an exemplification of the invention.

Example 1

Method

Patient-specific surgical devices designed as per Scheme A were applied to the intact knee in extension and/or flexion at the start of a TKA prior to soft tissue releases to mark bone resections. The Patient-specific surgical devices contacted the femur and tibia simultaneously and acted to re-align the knee and tension the peri-articular soft tissues. Ten (10) patients had guides applied in flexion and extension and 3 additional patients used guides in extension only. A forty (40) patient cohort was similarly analysed. Data was prospectively collected on these 13 patients examining medial and lateral soft tissue laxity in maximum extension, 20° and 90° of flexion pre and post-operatively.

Results

Values for periarticular tissue tension of the knee within normal ranges and minimal medial lateral and 0 vs 90° difference is provided in Table 1 below. An appropriately balanced knee will typically meet all of these criteria.

TABLE 1

Normal ranges for periarticular tissue tension

| | Medial (°) | Lateral (°) | Medial vs Lateral (°) |
|---|---|---|---|
| 0° | 1.5-7 | 2-8 | ≤2 |
| 20° | 0-6 | 0.5-9 | ≤3 |
| 90° | 0.5-5 | 1-6 | ≤3 |
| 0° vs 90° | ≤2 | ≤3 | Medial and Lateral |

Conventional Metal Jigs

Table 2 below demonstrates the balance achieved with respect to the normal ranges in Table 1, in the first proof of concept study using computer navigation and conventional metal resection jigs. As can be seen from this data, the balance is particularly good in extension and medially which is advocated as being of primary importance.

Figure 22:
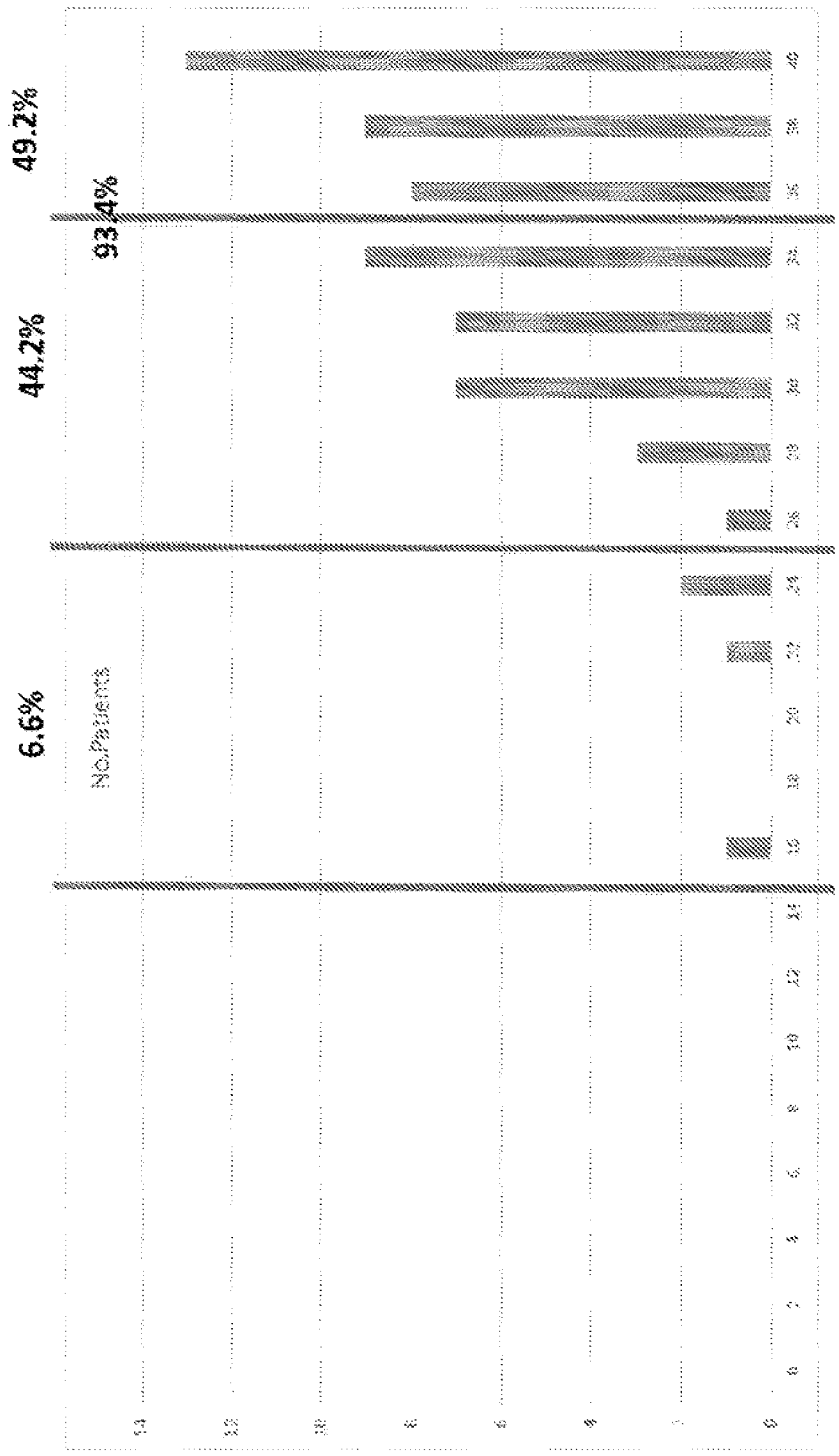
FIG. 22. Patient satisfaction based on the validated satisfaction section of the American knee society.

This degree of balance was associated with high patient satisfaction based on the validated satisfaction section of the American knee society (see FIG. 22). These results are equivalent to the best published results for satisfaction seen in recent studies where force sensors were used to measure pressure to document balance in a knee.

TABLE 2

Balance achieved versus normal values (Table 1)

| | Medial (°) | Lateral (°) | Medial vs Lateral (°) |
|---|---|---|---|
| 0° | 98.3% | 96.7% | 93.4% |
| 20° | 93.4% | 96.7% | 90.2% |
| 90° | 93.4% | 55.7% | 57.4% |
| 0° vs 90° | 91.8% | 59.0% | 59.0% |

Ten Patient Cohort:

Soft tissue tension within parameters described for normal subjects was attained medially and laterally in: 0 and 20° of flexion for all 13 cases utilising the extension guide and in all 10 cases in 90° of flexion utilising the flexion guide.

Post-operatively the mean difference in medial versus lateral laxity was 0.8° at 0°, 0.88° at 20° and 0.85° at 90° of flexion with a range of 0-1.5° across all positions and all knees. Pre-operatively the difference between medial and lateral laxity across all knees and assessed at each position tested ranged from 0-9°. Preoperatively the mean difference in medial versus lateral laxity was 4.3° at 0°, 5.5° at 20° and 1.58° at 90° of flexion.

In the ten cases utilising both flexion and extension guides, 0 versus 90° flexion laxity on the medial side displayed a mean difference of 1.4° (range 0-3) and on the lateral side a mean difference of 1.75° (range 0.5-4) was recorded.

Forty Patient Cohort

TABLE 3

Balance achieved versus normal values (Table 1)

| | Medial (°) | Lateral (°) | Medial vs Lateral (°) |
|---|---|---|---|
| 0° | 95% | 87.5% | 97.5% |
| 20° | 100% | 97.5% | 90% |
| 90° | 95% | 82.5% | 85% |
| 0° vs 90° | 90% | 82.5% | 80% |

The data for the forty patient cohort also demonstrates a minimal side to side difference in tissue laxity at different flexion points (see Table 4). These are very similar results to those for the conventional metal jigs (see Table 2), except for an increase in normality of lateral tissues

TABLE 4

Medial vs lateral balance

| Difference Medial vs Lateral tissue laxity | Pre-op | Post-op |
|---|---|---|
| 0° | 5.2° | 0.79° |
| 20° | 5.81° | 1.4° |

TABLE 4-continued

Medial vs lateral balance

| Difference Medial vs Lateral tissue laxity | Pre-op | Post-op |
|---|---|---|
| 90° | 1.92° | 1.51° |
| Range all knees and positions | 0-12.5° | 0-4.5° |

As shown in Table 5, this data seemingly closely approximates the normal situation, such as that demonstrated by a recent cadaver study (i.e., Roth et al.), which measured the difference in laxity in normal knees between 0 and 90 degrees of flexion.

TABLE 5

Difference in laxity between 0 and 90 degrees of flexion

| | Mean Difference 0 vs 90° tissue laxity | Range | Roth et al. Mean Difference 0 vs 90° tissue laxity |
|---|---|---|---|
| Medial | 1.13° | 0.5-5.5° | 1 ± 0.5 |
| Lateral | 2° | 0.5-8° | 2.5 ± 0.8 |

In addition to the above, medial and lateral laxity in 0 and 90 degrees of flexion when compared against those values recommended by Hesterbeek et al. (see below) for TKA, demonstrate that our mean laxities sit close to the mid point of the recommended ranges with very few readings outside the recommended range.

Hesterbeek Recommended Laxity Values:
  medial: 0.7-3.9° (extension); 0-5.5° (flexion)
  lateral: 0.2-5.4° (extension); 0-7.1° (flexion)
  Mean medial laxity extension—2.4° (range 1-5.5°) (1 reading outside Hesterbeek range)
  Mean medial laxity flexion—3.2° (range 1-8°) (2 readings outside Hesterbeek range)
  Mean lateral laxity extension—2.4° (range 1-4°)
  Mean lateral laxity flexion—4.1° (range 0-10°) (3 readings outside Hesterbeek range)

Conclusions

These patient-specific surgical devices show promise for attaining soft tissue tension that is both normal and balanced across the knee joint. This may help diminish revision due to instability which was recorded as the revision diagnosis in 18.7% of patients (Lombardi 2013).

Example 2

The primary purpose of the study was to determine whether the coronal plane tissue of the varus OA knee is contracted medially or lax laterally. Our null hypothesis was that medial contractures would not be present in the varus OA knee when referenced to the corrected, neutral axis of each knee.

Materials and Methods

Seventy-two Computer Assisted Surgery (CAS) TKA patients contributing 79 knees were included in the study. Inclusion criteria were patients with varus degenerative osteoarthritis of any degree scheduled for primary TKA who had not undergone previous ligament reconstruction surgery, knee osteotomy or suffered other trauma likely to distort the peri-articular soft tissues. Exclusion criteria were patients who declined consent or where intra-operatively placement of navigation pins was considered high risk due to poor bone stock or soft tissue. Ethical approval was obtained from the relevant institutional review board and written informed consent was obtained pre-operatively for all patients.

A medial para-patellar approach to the knee was undertaken. Femoral and tibial navigation pins were inserted. All landmarks were identified and registered in the navigation system for calculation of the mechanical axes of the femur, tibia, lower limb and generation of an individualised 3D model of the patient's anatomy using computer navigation software (BrainLab, Munich, Germany). The status of the anterior cruciate ligament (ACL) and posterior cruciate ligament (PCL) was recorded. Osteophytes were left in-situ to assess the knee as close to its pathological OA state as possible. The anterior horn of the medial meniscus was left intact. If required release of the deep band of the medial collateral ligament was limited to 5 mm by sharp dissection in order to maintain the state of medial soft tissues as close to the pre-operative state as possible whilst allowing clear navigation registration similar to the methods of Bellemans et al [2].

Figure 16:
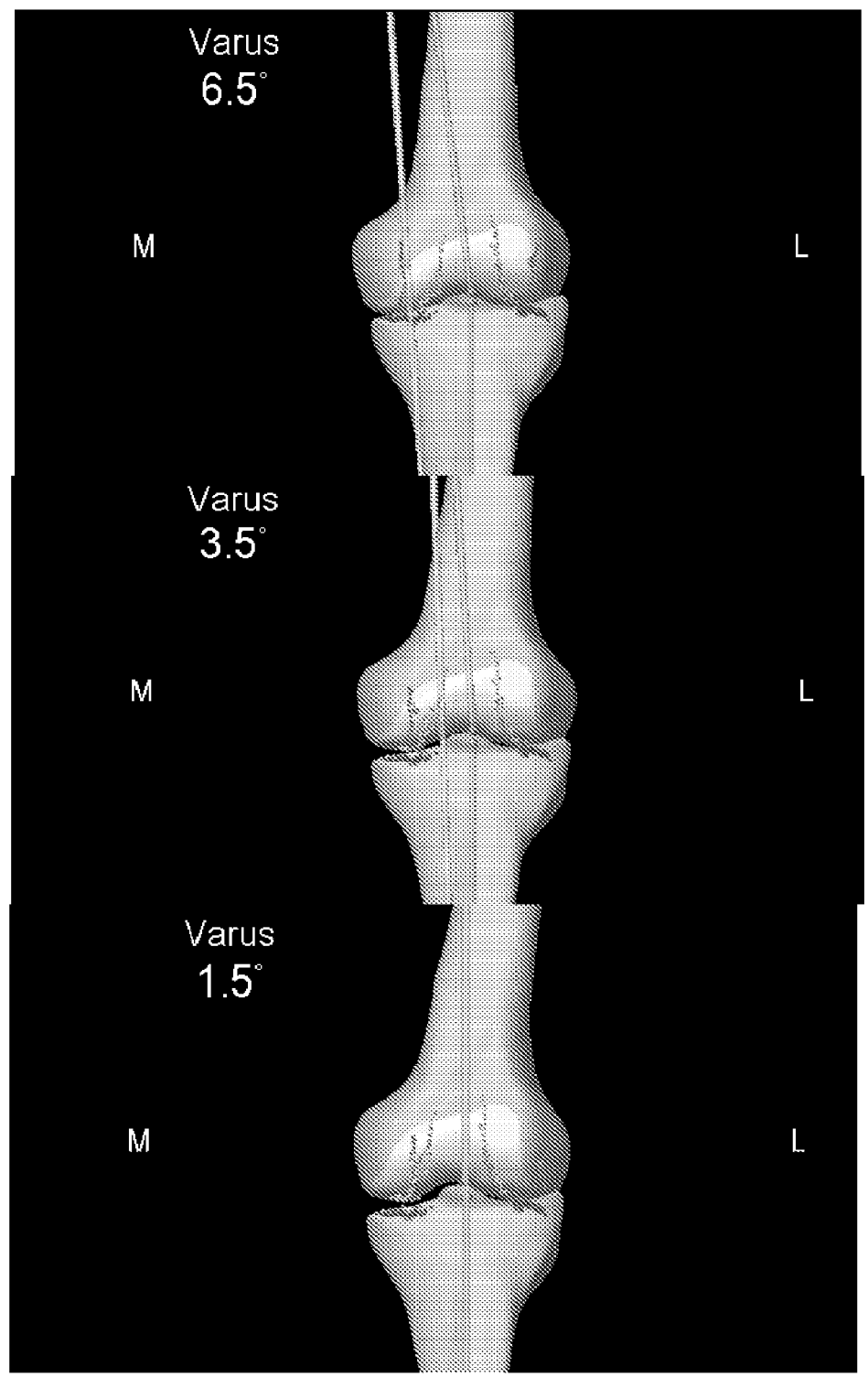
FIG. 16: Demonstration of the method of knee alignment moving from deformity to maximum co-axiality of the lower limb, tibial and femoral mechanical axes through a central portion of the knee (Medial and lateral laxity was measured in maximum extension and 20° flexion as deviation from this point).

The patella was reduced and the degree of fixed flexion deformity (FFD) or hyperextension was recorded in maximum extension. The mechanical axis of the limb was corrected to the centre of the knee by observing CAS displays. The femoral and tibial mechanical axes were manipulated to be as co-linear as possible to the limb axes at this position. Direct observation of the joint was undertaken during measurements to prevent subluxation and ensure congruency (FIG. 16). These methods produced a limb position acting to define a neutral, corrected alignment for each knee consistent with prior literature [6,7]. The Hip Knee Ankle Angle (HKAA) was recorded at this point. The knee was moved through a medial-lateral arc via manual force from this corrected position. Measurements were defined by medial and lateral deviation from the corrected axis point in degrees as indicated by the navigation software. These measurements were undertaken in maximal extension and 20 degrees of flexion. The point of maximum varus deformity or the "loaded HKAA" was recorded.

Modern navigation systems have been validated for these measurements [2]. A medial coronal plane contracture was considered present when the knee could not be aligned to its neutral, corrected axis or when the knee did not correct beyond its axis displaying movement within previously documented physiological ranges for elderly controls [8]. In these circumstances, medial laxity was recorded as zero. Lateral laxity was considered abnormal when it exceeded 8° [2, 8, 9]. Once the data was recorded a CAS TKA was performed. In all cases, the procedure and measurements were performed by a single, high volume arthroplasty surgeon (MM) at a single centre.

All data was prepared and analysed using Prism 5 for Mac OS X Version 5 (GraphPad Software Inc. La Jolla, CA). Statistical comparisons were made using one-way analysis of variance with Tukey's Multiple Comparison tests.

Results

Seventy-two patients contributed 79 TKA's. Five males and two females underwent bilateral TKA's. Table 6 demonstrates the demographics of the study population.

TABLE 6

Patient demographic detail.

| | Mean +/− SD | Range |
|---|---|---|
| Age (years) | 64.1 +/− 7.2 | 49-81 |
| Sex | 40 Male, 32 Female | |
| Body Mass Index (BMI) | 32.3 +/− 5.3 | 20.2-52.2 |
| FFD (degrees) (−ve hyperextension) | 5.0 +/− 5.2 | 18.5 to −8.5 |
| Varus (degrees) | −7.8 +/− 3.1 | −15 to −3 |

Seventy-nine knees were included in the study; however, 78 knees were available to examine individual patterns of medial and lateral laxity. The reason for this was in one subject, the mechanical axis of the limb could not be manipulated to pass through the centre of the knee to attain a corrected, neutral axis in maximum extension or 20° of flexion. Therefore, no zero point was attained and thus no medial and lateral laxity values were recorded. This subject was a 54-year-old female with a FFD of 0.5° and a varus deformity (loaded HKAA) of −13.5°. This patient was important to the study as a contracted knee. A medial contracture was thus present in 13.9% (11/79) of knees. Table 7 displays the patterns of contracture and laxity in the remaining 78 patients compared to published values in healthy knees.

TABLE 7

Distribution of Laxity Patterns in 78 subjects with individual laxity assessment. Normal medial and lateral laxity was defined in relation to published laxity data ranges for healthy subjects [2, 8, 9].

| | Normal Medial laxity (≥0.5°) | Medial contracture (<0.5°) |
|---|---|---|
| Normal Lateral laxity (≤8°) | 74.4% (58/78) | 6.4% (5/78) |
| Abnormally increased lateral laxity (>8°) | 12.8% (10/78) | 6.4% (5/78) |

The majority of subjects (74.4%) recorded coronal laxity parameters within limits previously published for healthy knees. We then examined those subjects with medial contractures, abnormal lateral laxity and the relationship between varus deformity and soft tissue alteration in more detail.

The neutral, corrected HKAA in the 10 patients with a medial contracture who could be manipulated to but not beyond their corrected axis point within physiological laxity ranges was −1.5+/−0.9°. There was no significant difference between the neutral, corrected HKAA of these 10 contracted knees and the neutral, corrected HKAA of the 68/78 non-contracted knees (p=0.819). A significant difference 2.3°±0.9° (p=0.015) was seen between the mean maximum varus (loaded axis) of contracted (−9.7°+/−0.8°, −14.5° to −6.5°) and non-contracted knees (−7.4°+/−0.3°; −15° to −2°).

In 20° of flexion a significant mean difference 2.2°±0.5° (p<0.001) in medial laxity persisted between contracted and non-contracted knees. Two of the ten contracted knees were still unable to be manipulated in 20° of flexion beyond their neutral, corrected HKAA within physiological ranges. In these knees, medial laxity was recorded as zero.

Contracted knees were more lax laterally. A significantly increased difference in the mean lateral laxity of contracted versus non-contracted knees in maximum extension 2.2°±0.8 (p=0.01), and 20° of flexion 2.4°±0.9 (p=0.008) was recorded.

TABLE 8

Laxity data in degrees for all knees, corrected and uncorrected knees with comparison of contracted versus non-contracted knees.

| | All Varus Knees (78) | Non-contracted Knees (68) | Contracted Knees (10) | Non-contracted vs Contracted - p-value |
|---|---|---|---|---|
| Medial Laxity - Max Ext | 1.6 +/− 1.0 | 1.8 +/− 0.9 (0.5-4) | 0 | NA |
| Medial Laxity - 20deg | 3.0 +/− 1.7 | 3.3 +/− 1.6 (0.5-7.5) | 1.1 +/− 0.7 (0-2) | <0.001 |
| Lateral Laxity - Max Ext | 6.1 +/− 2.5 | 5.9 +/− 2.4 (1-11.5) | 8.1 +/− 2.4 (4.5-11) | 0.010 |
| Lateral Laxity - 20deg | 6.8 +/− 2.7 | 6.5 +/− 2.6 (2-13) | 8.9 +/− 2.4 (5.0-14.5) | 0.008 |
| Laxity Arc - Max Ext | 7.7 +/− 2.3 | 7.7 +/− 2.2 (3.5-14) | 8.1 +/− 2.4 (4.5-11.0) | 0.607 |
| Laxity Arc - 20deg | 9.7 +/− 2.4 | 9.8 +/− 2.3 (6-16) | 10.0 +/− 2.0 (7-14.5) | 0.697 |

Figure 17:
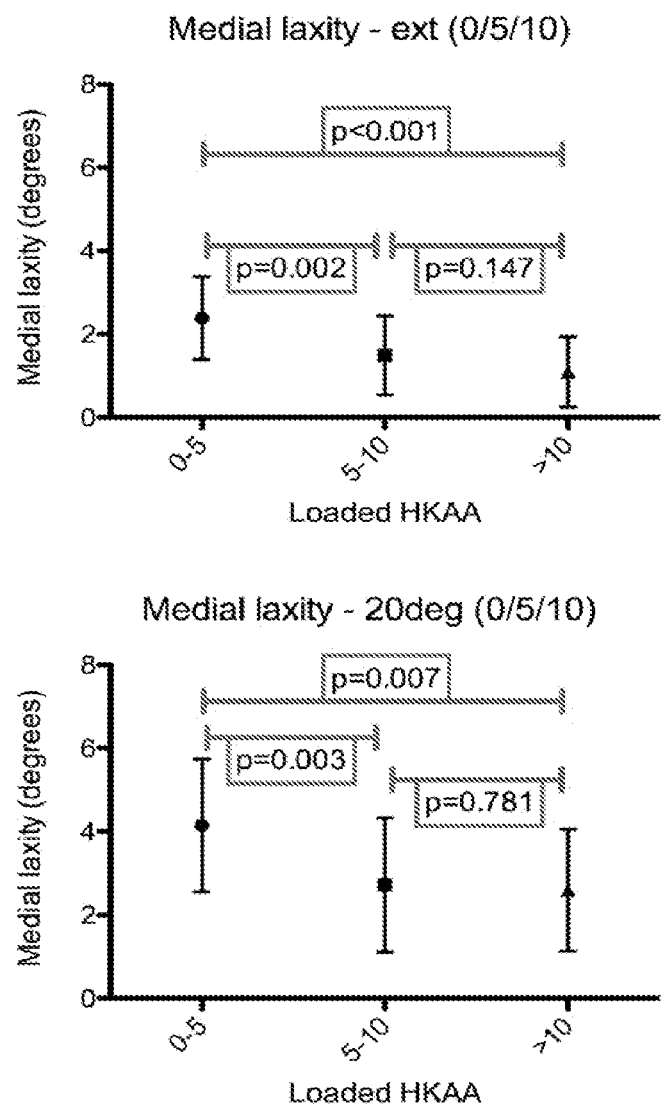
FIG. 17: Medial laxity compared to subjects grouped by maximum varus deformity.

We then examined the entire cohort for changes in medial and lateral laxity by grouping subjects according to their maximum varus deformity (loaded axis) and comparing laxity parameters between these groups. Medial laxity decreased as the varus deformity of the limb increased. FIG. 17 demonstrates a statistically significant mean difference in medial laxity between 0-5° vs 5-10° but non-significant for 5-10° vs >10° in both maximum extension and 20° of flexion.

Figure 18:
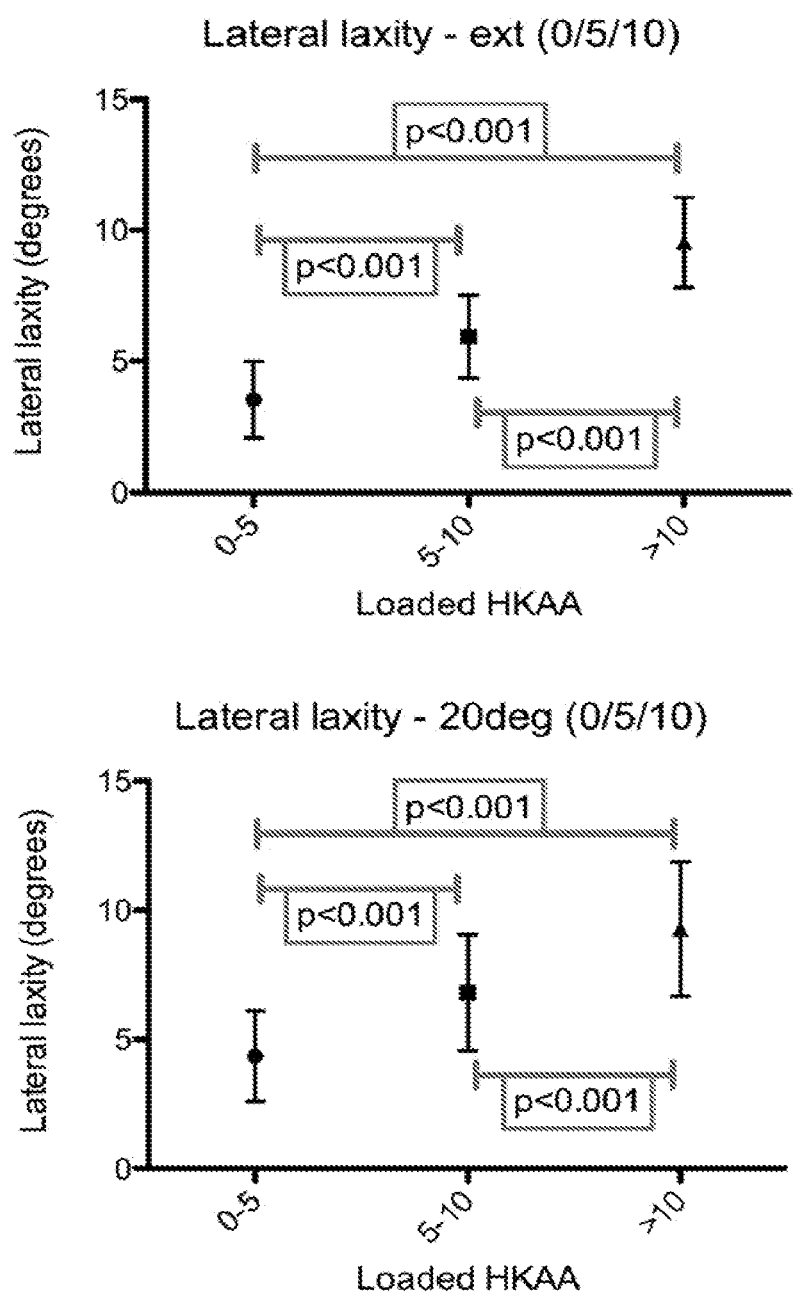
FIG. 18: Lateral laxity compared to subjects grouped by maximum varus deformity.

Lateral laxity increased as the varus deformity of the limb increased. There was a significant increase in laxity between each point of increasing varus deformity in both maximum extension and 20° of flexion (FIG. 18).

We analysed the soft tissue parameters in maximum extension and 20° of flexion to confirm that a true difference existed between these two measurement positions. We found the coronal soft tissues to have a total medial-lateral coronal arc at 20° of flexion (9.7°±2.4°) that was significantly greater (p<0.001) compared with the arc demonstrated at maximum extension (7.7°±2.3°). Both medial and lateral laxity for 20° flexion versus maximum extension was significantly increased with mean differences of 1.4° (p<0.001) and 0.6° (p=0.007).

The study was primarily designed to define the incidence of medial contracture and abnormal lateral laxity. Additionally we identified unexpected patterns of laxity in the study group that would potentially affect surgery. These alterations in coronal laxity were not constant between maximum extension and 20° of flexion. More medial laxity than lateral laxity at full extension was recorded in 6/78 (7.6%) knees. Five of these six knees maintained the same pattern at 20° of flexion, while six other knees displayed greater medial than lateral laxity at 20° of flexion. Therefore, at 20 degrees of flexion, 14.1% (11/78) of varus knees have greater medial than lateral laxity.

DISCUSSION

The effect of OA on the soft tissues of the knee still requires comprehensive definition. This information is important for intra-operative decision making during TKA.

Studies to date have examined the coronal plane tissues of the knee in a single position preoperatively, varied positions intraoperatively after bony resection or post-operatively without reference to initial soft tissue parameters [2, 3, 4, 5, 9, 10, 11, 12]. The purpose of this study was to define the coronal plane medial and lateral laxity of the end stage OA, knee prior to TKA, referenced from the corrected, neutral HKAA of each knee. This was undertaken in maximum extension and 20° of flexion to assess the contributions of posterior and coronal plane structures to any alteration of tissue laxity. These measurements were compared to published values for healthy subjects to assess the impact of OA on the coronal plane soft tissues of the knee. Given this comparison, it is important to understand the measurement of medial and lateral laxity in the healthy knee and how this corresponds to our study methods.

In the healthy knee, medial and lateral laxity is measured as deviation from the resting point of the knee. This point is not constant between subjects. This is seen in studies of healthy knees assessing their resting or neutral position with mean HKAA values ranging between −1 to −1.3° and standard deviations in these studies between 2-2.8° [6, 7, 13, 14, 15, 16]. The laxity measures documented when measuring from these resting positions in normal subjects are displayed in Table 9 [8, 9, 17, 18, 19, 20].

The individual initial neutral position of the OA knee and lower limb is unknown, due to its alteration by disease. This is important because if we cannot return a knee to its pre-disease position it is impossible to measure any medial and lateral distortion of the soft tissues by OA. Previous studies have used differing techniques to address this issue.

Bellemans and Hohman et al both determined contracture to be present based on whether a knee could be realigned to a constant reference point of a hip knee ankle angle (HKAA) of 0° and the correlation between the subject's initial varus deformity and measures of maximal varus and valgus stress alignment [2,3]. The healthy knee has a mean HKAA of −1.33°+/−2.34° [6]. The mean medial and lateral laxity in extension has been reported in the elderly healthy knee to be 2.3+/−0.9° and 2.8+/−1.3° respectively [8]. An osteoarthritic knee that had a pre-disease HKAA of −4° (varus) is unlikely to realign to a HKAA of 0° whether or not a medial contracture is present. Therefore, whether a varus knee can attain a HKAA of 0° is not definitive evidence for the presence or absence of a medial contracture. Similarly, the points of maximum varus or valgus attained under manual stress will be affected by initial limb alignment.

Other studies have assessed the absolute gap with tensor devices after bone resection, with or without the consideration of the amount of bone resected [4,5]. This approach measures gaps after alteration of both the bony and ligamentous anatomy of the knee and equalisation of pressure on the medial and lateral sides of the knee. It does not account for the initial position of the limb or the fact that medial and lateral laxity is typically different both in in-vivo studies and a recent cadaver study has confirmed these findings [8, 9, 17, 18, 19, 20, 21].

To address these concerns we placed the mechanical axis of the limb through the centre of the knee, whilst ensuring congruency of the joint under direct vision and made the femoral and tibial mechanical axes as co-linear as possible. This created a corrected or neutral HKAA position for each knee that is consistent with prior literature and thus allowed the measurement of laxity to be individualised for each subject [6, 16]. It is important to note a HKAA of 0° will only occur when the tibial and femoral axes match at the knee and they are both co-linear with the mechanical axis of the limb. More commonly, the neutral HKAA will approach 0° (FIG. 1). In our subjects, the mean neutral, corrected HKAA in maximum extension was −1.4+/−1.3 with a range of 1.5 to −5.5. This is similar to the mean HKAA and the varus range in the healthy population [6]. We believe these factors mean our neutral point from which we measured medial and lateral laxity in each knee is a close approximation of the pre-disease alignment of that knee and addresses many of the issues demonstrated in previous studies that have sought to examine the alteration of coronal plane knee tissues by OA [2, 3, 4, 5].

Our results have demonstrated the variable nature of laxity patterns in the coronal plane of the varus OA knee with up to 15° varus deformity. Our findings support both the findings of contracture and laxity by previous authors but place them in a more individual context and help reconcile the conflicting prior findings in the orthopaedic literature [2, 3, 4, 5]. The "classic" pattern of contracted medial tissue and lax lateral tissue was only recorded in 6.4% (5/78) of patients. Medial contracture and lateral laxity also exist in isolation with normal tissue laxity found on the opposite side of the joint in many patients. The majority of patients in this study had medial and lateral laxity measurements within ranges previously described for healthy subjects [8, 17, 18, 19, 20].

We found a medial contracture to be present in 12.8% (10/78) of patients in maximum extension. Hohman and Bellemans et al found contractures developed at varus deformity beyond ten degrees. In our subjects, knees with contracture had a significantly higher mean maximum deformity (loaded axis) value than non-contracted knees but displayed a range of maximum deformity of −6.5 to −14.5°. The initial alignment from which these knees developed this deformity and contracture did not appear to be different between contracted and non-contracted knees with no significant difference found between the neutral corrected HKAA of these two groups. In the cohort as a whole we found a non-significant decrease in medial laxity comparing subjects with 5-10° of deformity to >100 of deformity. Therefore, increased varus deformity is often present with contracture but deformity of >10° is not a reliable proxy marker for the presence of contracture, indeed the mean varus deformity of contracted knees in our series was 9.7°. When contractures are present they have both a posterior and medial contribution as demonstrated by the significant difference in medial laxity between contracted and non-contracted knees at both maximum extension and 20° of flexion. The influence of the posterior structures is also demonstrated by the fact that of the eleven subjects with contracture in maximum extension only three met the same criteria for contracture in 20° of flexion. Additionally, significant increases in medial and lateral laxity, and total coronal motion were seen in 20° of flexion once the influence of the posterior structures was removed.

The mean medial laxity in our subjects at maximum extension with was 1.6+/−1.0° this compares to the healthy population where mean medial laxity is reported to range between 2.3-3.6° [8, 9, 18]. The small differences in results may reflect variations in subject groups and investigative techniques but in any case, these differences in medial laxity are likely below or at the margin of clinical significance.

These findings have disproved our null hypothesis that medial contracture is not present in the varus OA knee when referenced to the corrected, neutral HKAA of each knee.

Studies of healthy knees have shown mean lateral laxity in either maximum extension or 10° of flexion varying between 4.1-4.9° [8, 9, 18]. In a study utilising similar investigative techniques to ours Jenny found a range for lateral laxity in maximum extension in healthy subjects of 2-8°, similar findings are seen in other studies [2,8,9]. Our subjects had a mean lateral laxity of 6.1+/−2.5°. In our subjects, 19.2% (15/78) of knees had lateral laxity of more than 8° (8.5°-11.5°) in maximum extension. We found a significant increase in laxity as varus deformity increased. Therefore, we would agree with the findings of Okamoto et al who described lateral laxity in the varus knee with more severe deformity [3.] We have been able to better quantify the individual degree and patterns of increased laxity showing it can exist in isolation or combined with a medial contracture.

Counter intuitively given the varus alignment of our subjects, 6/79 (7.6%) knees in extension and 11/79 (13.9%) knees in 20° of flexion showed an unexpected pattern of increased medial versus lateral laxity which has not been previously reported.

The findings of these laxity patterns in our subjects have direct relevance to TKA. Surgeons should not assume laxity patterns based on deformity or that abnormality in the coronal plane of the knee on one side of the joint correlates to abnormality on the opposite side of the joint. The "releases" that occur as part of the approach to the knee during TKA and resection of osteophytes will likely address the degree of medial contracture we have demonstrated in the majority of cases with a varus deformity of up to 15°. Therefore, if an extensive medial release is required it may represent an uncommon clinical situation or importantly reflect errors within the surgical procedure. If a contracture is present then both a medial and posterior cause should be sought. In patients with abnormal lateral laxity the surgeon should not release medial tissue to attain balance based on abnormal lateral tissue and careful surgical technique should avoid any further increase in lateral laxity to potentially problematic levels [22].

We would acknowledge the limitations of our study. The patient group was predominantly Caucasian and their selection for TKA may not be indicative of other surgical series. Our study is consistent with described in-vivo techniques for measuring coronal plane laxity and our subjects had flexion and varus deformity parameters similar to previously examined OA knee groups in the literature [2, 3, 6, 7, 8, 17, 18, 23, 24]. Many studies define coronal plane knee laxity by a total arc of movement at 20° of flexion and our findings are consistent these prior studies [17, 23, 24]. Therefore, we believe the findings of our study are valid in the OA knee with varus deformity of up to 15°.

Manual stress testing was performed to assess coronal plane laxity. This is consistent with prior studies [2, 9]. Whilst an experienced surgeon performed this, some degree of variability in the forces exerted during testing is inevitable. Mitigating this is the fact that ligaments are viscoelastic structures and measurements were recorded at maximal displacement. This should correspond to the plateau of the tension/length curve minimising any effects of variation in force [9]. It is not possible in an in-vivo setting to utilise the same invasive techniques with multiple controlled parameters and measurements that are utilised in cadaver studies given the ethical implications of prolonging surgery particularly in relation to infection and fracture risk [21]. It is also possible to take a pragmatic view of our study given that our laxities were measured at a point in the surgical exposure less than that required to complete the operation. Therefore, the measured laxities approximate those present at a point near the commencement of surgery and thus our results are useful for planning surgery from this initial point even if they do not represent the pure measure of medial and lateral laxity in the in-vivo setting of the end stage OA knee.

We cannot know that the corrected, neutral HKAA was the best starting point from which to measure medial and lateral coronal laxity but we do not believe it would have altered the conclusions of our study. Our corrected, neutral HKAA range of 1.5 to −5.5° is consistent with the varus HKAA range demonstrated by Bellemans et al in the healthy population of 0° to −8° [6]. Our measurements were non-weight bearing. Studies show increased varus alignment with weight bearing of 1.6-2° [25, 26]. An increase in varus alignment would have acted to further normalise our HKAA range and medialize the initial corrected, neutral point. The effect of measuring displacement from a more varus starting position would have been to increase the medial and decrease the lateral laxity measured further normalising our results.

In conclusion we have shown medial contractures referenced to the individual corrected, neutral axis of the varus OA knee with up to 15° deformity are uncommon. When present they are relatively small and occur via contributions from both medial and posterior structures. Increased lateral laxity is a more common finding but the patterns of coronal plane laxity alteration in the end stage OA knee at the time of TKA are highly variable and correlate poorly to the initial or subsequent varus deformity of the limb. Our findings help reconcile the previous conflict in the orthopaedic literature. An awareness of these findings will assist the surgeon during TKA to optimally balance and normalise the coronal plane soft tissues.

TABLE 9

Literature review of in-vivo coronal plane laxity in the normal and OA knee. Mean with standard deviation data (+/− range).

| Paper | Population | Number of Knees | Age | Measurement Technique | Medial Laxity- 0 deg | Medial Laxity- 10 deg | Medial Laxity- 20 deg | Medial Laxity- 70 deg |
|---|---|---|---|---|---|---|---|---|
| Okazaki (2005) | Healthy | 50 | 25.9 +/− 7.5 | Stress X-ray | | 2.4 +/− 1.6 | | |
| Heesterbeek (2008) | Healthy | 30 | 62 (6.4) | Stress X-ray | 2.3 +/− 0.9 (range 0.2-4.1) | | | 2.5 +/− 1.5 (range 0-6.0) |
| Jenny (2009) | Healthy | 20 | 24 (18-36) | Computer assisted surgery | 3.6 +/− 1.2 (range 2-7) | | | |
| Creaby (2010) | Healthy | 32 | 59 | Dynamometer | | | 8.4 +/− 3.2 | |
| Tokohura (2004) | Healthy | 20 | 27.2 (18953) | MRI leg weight | | | | |

TABLE 9-continued

Literature review of in-vivo coronal plane laxity in the normal and OA knee. Mean with standard deviation data (+/- range).

| | | | | | | | |
|---|---|---|---|---|---|---|---|
| Bellmans (2009) | Varus OA | 35 | — | Computer assisted surgery | 0.6 (range 3-4) | | |
| Creaby (2010) | Varus OA | 32 | 66 | Dynamometer | | 9.2 +/- 2.9 | |
| McAuliffe (2015) | Varus OA | 55 | 64 (49-79) | Computer assisted surgery | 1.6 +/- 1.1 (0-4) | 3.1 +/- 1.7 (0-7.5) | |

| Paper | Medial Laxity- 80 deg | Medial Laxity- 90 deg | Lateral Laxity- 0 deg | Lateral Laxity- 10 deg | Lateral Laxity- 20 deg | Lateral Laxity- 70 deg | Lateral Laxity- 80 deg | Lateral Laxity- 90 deg |
|---|---|---|---|---|---|---|---|---|
| Okazaki (2005) | 1.7 +/- 1.4 | | | 4.9 +/- 2.0 | | | 4.8 +/- 3.2 | |
| Heesterbeek (2008) | | | 2.8 +/- 1.3 (range 0.6-5.4) | | | 3.1 +/- 2.0 (range 0.1-7) | | |
| Jenny (2009) | | 2.1 +/- 1.2 (range 0-5) | 4.1 +/- 1.9 (range 2-8) | | | | | 3.7 +/- 1.2 (range 2-6) |
| Creaby (2010) | | | | | 10.7 +/- 3.7 | | | |
| Tokohura (2004) | | 2.8 +/- 0.9 | | | | | | |
| Bellemans (2009) | | | 4.1 (range 2-8) | | | | | |
| Creaby (2010) | | | | | 8.5 +/- 2.7 | | | |
| McAuliffe (2015) | | 3.9 +/- 1.4 (1-7.5) | 6.2 +/- 2.8 (0-12) | | 6.9 +/- 2.9 (2-15) | | | 4.7 +/- 2.0 (1-12) |

REFERENCES

1. Whiteside L A, Saeki K, Mihalko W M. Functional Medial Ligament Balancing in Total Knee Arthroplasty. Clin Orthop Relat Res 2000, 380:45
2. Bellemans J, Vandenneucker H, Vanlauwe J, Victor J. The Influence of Coronal Plane Deformity on Mediolateral Ligament Status: An Observational Study in Varus Knees. Knee Surg Sports Traumatol Arthrosc. 2010, 18:152.
3. Hohman D W, Nodzo S R, Phillips M, Fitz Wolfgang. The Implications of Mechanical Alignment on Soft Tissue Balancing in Total Knee Arthroplasty. Knee Surg Sports Traumatol Arthrosc. 2014 Epub September
4. Matsumoto T, Muratsu H, Tsumura N, Mizuno K, Kurosaka M, Kuroda R. Soft Tissue Balance Measurement in Posterior-Stabilized Total Knee Arthroplasty With a Navigation System. J Arthroplasty 2009, 24: 358
5. Okamoto S, Okazaki K, MitsuyasuH, Matsuda S, Iwamoto Y. Lateral Soft Tissue Laxity Increases but Medial Laxity does not Contract with Varus Deformity in Total Knee Arthroplasty. Clin Orthop Rel Res 2013, 471:1334.
6. Bellemans J, Colyn W, Vandenneucker H, Victor. The Chitranjan Ranawat Award: Is Neutral Mechanical Alignment Normal for All Patients? The Concept of Constitutional Varus. J Clin Orthop Rel Res 2012, 470:45
7. Cooke D, Scudamore A, Li J, Wyss U, Bryant T, Costigan P. Axial Lower Limb Alignment: Comparison of Knee Geometry in Normal Volunteers and Osteoarthritic Patients. Osteoarthritis and Cartilage. 1997, 5:39.
8. Heesterbeek P J C, Verdonschot N, Wymenga A B. In Vivo Knee Laxity in Flexion and Extension: A Radiographic Study in 30 Older Healthy Subjects. The Knee. 2008, 15:45.
9. Jenny J-Y. Coronal Plane Knee Laxity Measurement: Is Computer-Assisted Navigation Useful? Orthop & Traumatol:Surg and Res 2010, 96:583.
10. Aunan E, Kibsgard T, Clarke-Jenssen J, Rohrl S M. A New Method to Measure Ligament Balancing in Total Knee Arthroplasty: Laxity Measurements in 100 Knees. Arch Orthop Trauma Surg. 2012; 132:1173
11. Joseph J, Simpson P M S, Whitehouse S L, English H W, Donnelly W J. The Use of Navigation to Achieve Soft Tissue Balance in Total Knee Arthroplasty—A Randomized Clinical Study. The Knee 2013; 20:401
12. Aunan E, Kibsgard T, Diep L M, Rohrl S M. Intraoperative Ligament Laxity Influences Functional Outcome 1 Year after Total Knee Arthroplasty. Knee Surg Sports Traumatol Arthrosc. 2014; June:
13. Chao E Y S, Neluheni E V D, Hsu R W W, Paley D. Biomechanics of malalignment. Orthopedic Clinics of North America. 1994 July; 25(3):379.
14. Hsu R W W, Himeno S, Coventry M B, Chao E Y S. Normal axial alignment of the lower extremity and load-bearing distribution at the knee. Clinical Orthopaedics and Related Research. 1990 June; 255:215.
15. Moreland J R, Bassett L W, Hanker G J. Radiographic analysis of the axial alignment of the lower extremity. J Bone Joint Surg Am. 1987 June; 69(5):745.
16. Cooke T D V, Sled E A, Scudamore R A. Frontal plane knee alignment: a call for standardized measurement. J Rheumatol. 2007; 34:1796.
17. Creaby M W, Wrigley T V, Lim B W, Bowles K, Metcalf B R, Hinman R S, Bennell K L. Varus-Valgus Laxity and Passive Stiffness in Medial Knee Osteoarthritis. Arthritis Care Res 2010, 62:1237
18. Okazaki K, Miura H, Matsuda S, Takeuchi N, Mawatari T, Hashizume Metal. Asymmetry of Mediolateral Laxity of the Normal Knee. J Orthop Sci. 2006, 11:264
19. Tokuhara Y, Kadoya Y, Nakagawa S, Kobayashi A, Takaoka K. The Flexion Gap in Normal Knees: An MRI Study. J Bone Joint Surg Br 2004; 86-B:1133.

20. Pottenger L A, Phillips F M, Draganich L F. The Effect of Marginal Osteophytes on Reduction of Varus-Valgus Instability in Osteoarthritic Knees. Arthritis and Rheumatism. 1990, 33:853
21. Roth J D, Howell S M, Hull M L. Native Knee Laxities at 0°, 450 and 900 of Flexion and their Relationship to the Goal of the Gap-Balancing Alignment Method of Total Knee Arthroplasty. J Bone Joint Surg Am 2015; 97:1678
22. Matsuda S, Ito H. Ligament Balancing in Total Knee Arthroplasty—Medial Stabilizing Technique. Asia-Pacific Journal of Sports Medicine, Arthroscopy, Rehabilitation and Technology (2) 2015:108
23. Wada M, Imura S, Baba H, Shimada S. Knee Laxity in Patients with Osteoarthritis and Rheumatoid Arthritis. Br J of Rheum 1996, 35:560
24. Brage M E, Draganich L F, Pottenger L A, Curran J J. Knee Laxity in Symptomatic Osteoarthritis. Clin Orthop Rel Res 1994, 304:164
25. Specogna A V, Birmingham T B, Hunt M A, et al.Radiographic measures of knee alignment in patients with varus gonarthrosis: effect of weightbearing status and associations with dynamic joint load. *Am J Sports Med.* 2007; (1):65-70.
26. Brouwer R W. Unicompartmental Osteoarthritis of the Knee: Diagnosis and Treatment of Malalignment. Proefschrift Rotterdam 2006. ISBN 90-75092-47-4

Example 3

The purpose of our study was to use computer navigation to correct the HKAA in maximum extension to a neutral alignment for that limb prior to TKA and compare this data to normative HKAA values and examine whether this could focus the current 6° alignment range for each knee.[4, 10-13] Our hypothesis was that the corrected, neutral HKAA of limbs undergoing TKA was not significantly different to the HKAA of healthy knees and that this method of individualizing coronal plane alignment may be useful in optimizing coronal alignment goals for TKA.

Materials and Methods

80 Computer Assisted Surgery (CAS) TKA patients contributing 89 knees were included in the study. These patients were part of a broader study examining the peri-articular soft tissue envelope at the time of TKA. Inclusion criteria were: patients with degenerative osteoarthritis scheduled for primary TKA who had not undergone previous ligament reconstruction surgery; knee osteotomy or suffered other trauma likely to distort the peri-articular soft tissues or the overall alignment of the limb. Exclusion criteria were: patients who declined to consent to participation or where intra-operatively placement of navigation pins was considered high risk due to bone stock or poor soft tissue quality. Ethical approval was attained from the relevant institutional review board and written informed consent was obtained pre-operatively for all patients.

A medial para-patellar approach to the knee was undertaken. Femoral and tibial navigation pins were inserted. All landmarks were identified and registered in the navigation system for calculation of the mechanical axes of the femur, tibia, lower limb and generation of an individualised 3D model of the patient's anatomy using computer navigation software (BrainLab, Munich, Germany). The patella was reduced and the degree of fixed flexion deformity (FFD) or hyperextension was recorded in maximum extension. The mechanical axis of the limb was corrected in maximum extension by manipulating the knee, while observing CAS displays and direct observation of the joint to prevent subluxation and ensure congruency. These methods produced a limb position from which we measured a neutral or corrected HKAA for each knee consistent with prior literature.[3, 4] FIG. 16 demonstrates this correction.

Limbs were also loaded manually to exacerbate their initial deformity to a maximum varus or valgus position. This produced a "loaded HKAA" or maximum point of deformity, which was also recorded. In all cases, the procedure and measurements were performed by a single, high volume arthroplasty surgeon (MM) at a single centre.

All data was prepared and analysed using Prism 5 for Mac OS X Version 5 (GraphPad Software Inc. La Jolla, CA).

Results 80 patients contributed 89 TKA's, six male subjects and three female subjects underwent bilateral TKA. The demographics of the study population are shown in Table 10.

TABLE 10

Patient demographic detail. Negative FFD denotes hyperextension.

| | Mean +/− SD | Range |
|---|---|---|
| Age (years) | 63.8 +/− 7.1 | 49-81 |
| Sex | 39 Male, 41 Female | |
| Body Mass Index (BMI) | 32.1 +/− 5.2 | 20.2-52.2 |
| FFD (degrees) | 4.5 +/− 4.9 | −8.5-15 |

The loaded and corrected HKAA values for all varus and valgus knees are presented in Table 11. There was no significant difference in the absolute change in HKAA between loaded and corrected axes when comparing varus to valgus knees (p=0.40). A significant difference was seen in varus and valgus knees with respect to FFD (p=0.02)

TABLE 11

Analysis of the corrected and loaded HKA in extension for the entire cohort and varus and valgus knees.

| | Overall (n = 89) | Varus knees (n = 72) | Valgus knees (n = 17) |
|---|---|---|---|
| Loaded HKA (degrees) | −5.1 +/− 6.7 (−20 to 13.5) | −7.9 +/− 3.3 (−20 to −0.5) | 6.9 +/− 2.9 (2.5 to 13.5) |
| Corrected HKA Angle (degrees) - max. ext. | −1.2 +/− 1.4 (−5.5 to 2) | −1.5 +/− 1.3 (−5.5 to 1) | 0.0 +/− 1.0 (−1 to 2) |
| Absolute change in HKA axis between loaded and corrected axes (degrees) for varus and valgus knees | N/A | 6.3 +/− 3.1 (0 to 17.5) | 7.0 +/− 2.8 (2 to 12.5) |
| FFD (degrees) (negative FFD denotes hyperextension) | 4.5 +/− 4.9 (15 to −8.5) | 5.1 +/− 5.1 (15 to −8.5) | 2.0 +/− 3.3 (−5.5 to 6) |

All values are in degrees and expressed as Mean +/− SD (Range). Negative denotes varus or hyperextension.

All values are in degrees and expressed as Mean +/−SD (Range). Negative denotes varus or hyperextension.

Figure 19:
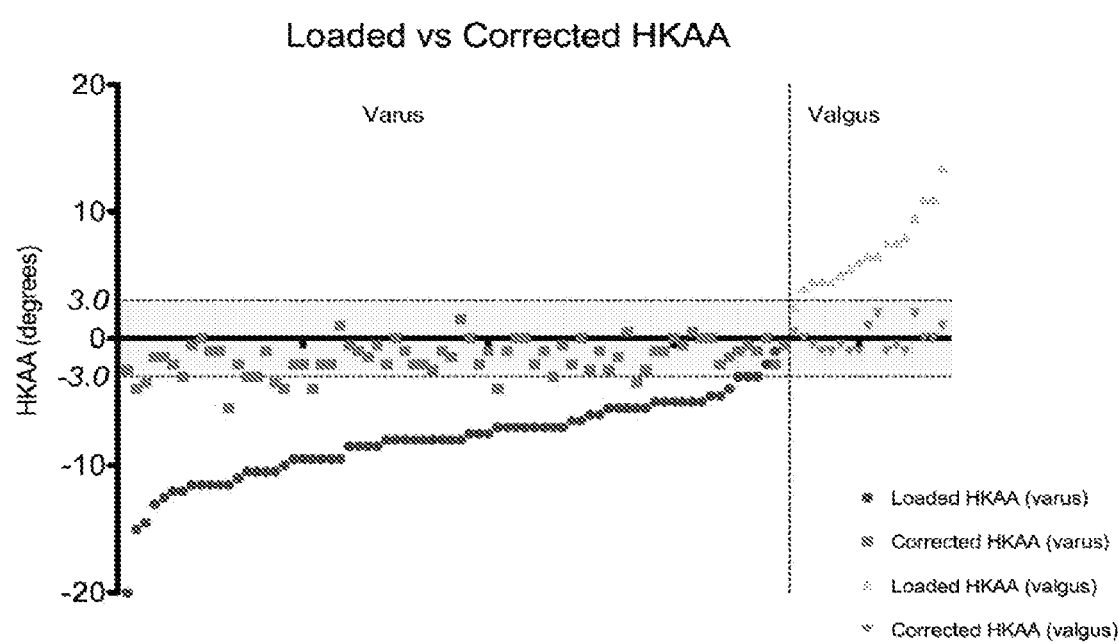
FIG. 19: The relationship of the loaded and corrected HKA with reference to neutral mechanical alignment+/−3°.
Figure 20:
FIG. 20: Demonstration of correction of the limb axes in 90° flexion. The limb, femoral and tibial mechanical axes were placed in a co-axial or parallel position and then medial and lateral laxity was measured as deviation from this point using the weight of the limb and manual force.

FIG. 19 depicts the alteration from the loaded HKAA to the corrected HKAA. The corrected HKAA in maximum extension was within +/−3° of 0° in 91.0% of patients. All valgus knees corrected to +/−3°. Eight varus knees did not display a corrected HKAA within this range. They recorded a corrected HKAA between −3.5° and −5.5°.

DISCUSSION

In TKA, a HKAA of 0° is often referred to as neutral mechanical alignment. It is important to understand that the neutral axis of a limb is not necessarily reflected by a HKAA of 0° although in some knees the neutral axis will also be 0°. This is seen in studies of healthy knees assessing their resting or neutral position where only a minority of knees record a I-IKAA of 0° with mean values ranging between −1°--1.3° and standard deviations in these studies between 2°-2.8°. These studies measure the HKAA in maximum extension but do not quantify the exact position of flexion or extension in their subjects. Cooke et al note the exclusion of patients with radiographs taken in greater than 20° of flexion.[4, 10-13] A limb axis of 0° will only occur when the centre of the tibia and femur match at the level of the knee joint and bony and soft tissue structures allow co-linearity of both the tibial and femoral mechanical axes. More typically, the axes approach co-linearity and a small degree of varus or valgus will be recorded. By placing the mechanical axis of the limb through the centre of the knee, ensuring congruency of the joint under direct vision and making the femoral and tibial mechanical axes as co-linear as possible we have created a corrected HKAA measurement for each knee that is consistent with prior literature.[3, 4] Modern navigation systems have been validated for measurements of alignment with an accuracy of 0.5°-1.0° depending on the level of deformity.[15]

In the non-arthritic knee the mean HKAA has been reported by Bellemans et al as −1.33°+/−2.34°.[4] The HKAA measured in our study was −1.2°+/−1.4° (Range: −5.5° to 2°). There is no significant difference between these values (p=0.61). The values we recorded displayed a lower SD. Our mean HKAA is consistent with the HKAA recorded in other studies of healthy populations.[4, 10-13] It is likely we have idealised the HKAA by removing the influence of weight bearing and hindfoot alignment. Previous studies have found weight bearing increases varus mal-alignment by a mean 1.6°-2° in varus knees.[16, 17] In addition, we found 91.0% of knees aligned to +/−3° and the remaining knees displayed a neutral HKAA between −3° and −5.5°. Therefore, it was possible to place knees undergoing TKA in an individualised neutral alignment either within accepted current alignment parameters of 0+/−3° or within 2.5° of these parameters in 100% of cases.

This has confirmed our hypothesis that the neutral HKAA of limbs undergoing TKA is not significantly different to the HKAA of normal knees unaffected by OA. It also suggests that this method of individualizing coronal plane alignment of the knee may be useful in TKA. A TKA aligned within the current safe zone of +/−3° may be significantly altered from its individual neutral alignment. TKA is non-anatomic and results in at least some distortion of the peri-articular soft tissue envelope. It is important the selected coronal alignment does not further heighten this disturbance. Depending on the degree of alteration, this may cause distortion or require release of the coronal plane soft tissues, which have, mean medial and lateral values in healthy subjects of 2.3°+/−0.90 and 2.8°+/−1.3° respectively.[5] Our results regarding the individualised neutral alignment of a knee would indicate that 91.0% of prostheses could be placed both in an alignment that would not exceed the mechanical properties of a total knee prosthesis nor cause significant distortion of the coronal plane soft tissues of the knee. It may be appropriate to align knees to >3° of varus to encompass the knees in our study where their neutral alignment was found to be between −3°--5.5° as there is support, though not universal, for this alignment not altering prosthetic survivorship.[18-21] Alternatively, these knees could be aligned to the limit of the −3° range, which would result in less soft tissue distortion whilst still respecting the mechanical limits of the prosthesis and neutral mechanical alignment goals. If we are to place prostheses at the limit of current mechanical alignment parameters, this requires the development of consistently accurate and reliable surgical techniques that prevent further unintended coronal plane alignment deviations. These deviations have been documented in some cases with current surgical techniques and this may compromise the longevity of the prosthesis.[22]

Regardless of the theoretical advantages or disadvantages of deviating from 0° of mechanical limb alignment we found that varus and valgus knees in our subjects did not show neutral alignment at the opposite end of the +/−3° range. Therefore, we believe optimal coronal plane TKA alignment might be better and safely redefined to −1° to 3° for a valgus knee and 1.5° to −3° for a varus knee and focused on the corrected neutral axis of the limb.

We would acknowledge our study has limitations. We have analysed data attained from CAS navigation techniques which is highly accurate for measurement but may not be identical to HKAA values recorded on long leg weight bearing radiographs in other studies.[4, 10-13] Our patient group is reflective of the practice of a single surgeon and therefore may not be applicable broadly to patients undergoing TKA, however, given the similarity in the coronal and flexion deformity parameters for our subjects compared to other studies we believe our results are a valid contribution to the literature.[4, 13, 25] We acknowledge that there is no way of knowing the original position of the lower limb prior to its alteration by OA and passage to TKA. However, we are unlikely to ever definitively answer this question given the logistics associated with such a study. Weight bearing is likely to have increased the spread of our results but is not likely to have altered the conclusions of our study.[16, 17] We have only examined static not dynamic alignment or other factors which are known to be important to OA progression.[24] Whether the suggested coronal plane position is more optimal for any individual knee depends on the laxity found in the coronal plane tissues at this point. This was beyond the scope of this paper but is an area we intend to study in the future. Despite these limitations, we feel the conclusions for this patient group are broadly applicable to the OA knee population undergoing TKA.

In conclusion, we have demonstrated that the neutral HKAA of knees with +13.50 to −20° of deformity at the time of TKA is similar to the healthy population. Therefore, whilst alignment does have an influence on OA development, initial alignment does not appear to have a strong association with end stage knee OA requiring TKA. Varus and valgus knees do not have a neutral HKAA at the opposite end of the 0+/3° range. Our method of planning coronal alignment may help lessen the inevitable distortion of the peri-articular coronal plane soft tissues by TKA by providing more focused alignment goals.

REFERENCES

1. Howell S M, Hodapp E E, Vernace J V, Hull M L, Meade T D. Are Undesirable Contact Kinematics Minimised After Kinematically Aligned Total Knee Arthroplasty? An Intersurgeon Analysis of Consecutive Patients. *Knee Surg Sports Traumatol Arthrosc* 2013; 21:2281-2287.
2. Abdel M P, Oussedik S, Parratte S, Lustig S, Haddad F S. Coronal alignment in Total Knee Replacement. Historical review, contemporary analysis, and future direction. *Bone Joint J* 2014; 96-B(7):857-862.
3. Cooke T D V, Sled E A, Scudamore R A. Frontal plane knee alignment: a call for standardized measurement. *J Rheumatol* 2007; 34:1796-1801.
4. Bellemans J, Colyn W, Vandenneucker H, Victor J. Is neutral mechanical alignment normal for all patients? The concept of constitutional varus. *Clin Orthop Relat Res* 2012 January; 470(1):45-53.
5. Heesterbeek P J C, Verdonschot N, Wymenga A B. In Vivo Knee Laxity in Flexion and Extension: A Radiographic Study in 30 Older Healthy Subjects. *The Knee* 2008; 15:45-49.
6. Hunter D J, Niu J, Felson D T, Harvey W F, Gross K D, McCree P et al. Knee alignment does not predict incident osteoarthritis. The Framingham Osteoarthritis Study. *Arthritis and Rheumatism* 2007 April; 56(4):1212-1218.
7. Brouwer G M, van Tol A W, Bergink A P, Belo R M, Bernsen M D, Reijman M et al. Association between Valgus and Varus Alignment and the Development and Progression of Radiographic Osteoarthritis of the Knee. *Arthritis and Rheumatism* 2007 April; 56(4):1204-1211.
8. Sharma L, Chmiel J S, Almagor O, Felson D, Guermazi A, Roemer F. The role of varus and valgus alignment in the initial development of knee cartilage damage by MRI: the MOST study. *Ann Rheum Dis* 2013; 72:235-240.
9. Belo J N, Berger M Y, Reijman M, Koes B W, Bierma-Zeinstra S M A. Prognostic factors of progression of osteoarthritis of the knee: A systematic review of observational studies. *Arthritis and Rheumatism* 2007 February; 57(1):13-26.
10. Chao E Y S, Neluheni E V D, Hsu R W W, Paley D. Biomechanics of malalignment. *Orthopedic Clinics of North America* 1994 July; 25(3):379-386.
11. Hsu R W W, Himeno S, Coventry M B, Chao E Y S. Normal axial alignment of the lower extremity and load-bearing distribution at the knee. Clinical Orthopaedics and *Related Research* 1990 June; 255:215-227.
12. Moreland J R, Bassett L W, Hanker G J. Radiographic analysis of the axial alignment of the lower extremity. *J Bone Joint Surg Am* 1987 June; 69(5):745-749.
13. Cooke D, Scudamore A, Li J, Wyss U, Bryant T, Costigan P. Axial lower limb alignment: comparison of knee geometry in normal volunteers and osteoarthritic patients. *Osteoarthritis and Cartilage* 1997; 5:39-47.
14. Cerejo R, Dunlop D D, Cahue S, Channin D, Song J, Sharma L. The influence of alignment on risk of knee osteoarthritis progression according to baseline stage of disease. *Arthritis and Rheumatism* 2002 October; 46(10): 2632-2636.
15. Bellemans J, Vandenneucker H, Vanlauwe J, Victor J. The influence of coronal plane deformity on mediolateral ligament status: an observational study in varus knees. *Knee Surg Sports Traumatol Arthrosc* 2010; 18:152-156.
16. Specogna A V, Birmingham T B, Hunt M A, Jones I C, Jenkyn T R, Fowler P J et al. Radiographic measures of knee alignment in patients with varus gonarthrosis: effect of weightbearing status and associations with dynamic joint load. *Am J Sports Med* 2007; 1:65-70.
17. Brouwer R W. *Unicompartmental Osteoarthritis of the Knee: Diagnosis and treatment of malalignment.* Proefschrift Rotterdam; 2006. ISBN 90-75092-47-4
18. Parratte S, Pagnan M W, Trousdale R T, Berry D J. Effect of postoperative mechanical axis alignment on the fifteen-year survival of modern, cemented total knee replacements. *J Bone Joint Surg Am* 2010; 92-A:2143-2149.
19. Matziolis G, Krocker D, Weiss U, Tohtz S, Perka C. A Prospective, randomised study of computer assisted and conventional total knee arthroplasty. three dimensional evaluation of implant alignment and rotation. *J Bone Joint Surg Am* 2007; 89-A:236-243.
20. Bonner T J, Eardley W G, Patterson P, Gregg P J. The effect of post-operative mechanical alignment on the survival of primary total knee replacements after a follow-up of 15 years. *J Bone Joint Surg Br* 2011; 93-B:1217-1222.
21. Collier M B, Engh C A Jr, McAuley J P, Engh G A. Factors associated with the loss of thickness of polyethylene tibial bearings after knee arthroplasty. *J Bone Joint Surg Am* 2007; 89-A:1306-1314.
22. Luyckx T, Vanhoorebeeck F, Bellemans J. Should we aim at undercorrection when doing a total knee arthroplasty? *Knee Surg Sports Trauma Arthrosc* 2015 June; 23(6):1706-1712.
23. Sharma L, Song J, Dunlop D, Felson D, Lewis C E, Segal N et al. Varus and valgus alignment and incident and progressive knee osteoarthritis. *Ann Rheum Dis* 2010; 69:1940-1945.
24. Miyazaki T, Wada M, Kawahara H, Sato M, Baba H, Shimada S. Dynamic load at baseline can predict radiographic disease progression in medial compartment knee osteoarthritis. *Ann Rheum Dis* 2002; 61:617-622.
Hohman D W, Nodzo S R, Phillips M, Fitz W. The implications of mechanical alignment on soft tissue balancing in total knee arthroplasty. *Knee Surg Sports Trauma Arthrosc* 2014 Sep. 13 [Epub ahead of print].

Example 4

The primary purpose of this study was to define the medial-lateral laxity of the soft tissues of the varus OA knee in 90° of flexion prior to any surgical releases at the time of TKA.

Materials and Methods

Sixty-five Computer Assisted Surgery (CAS) TKA patients contributed 72 knees, five males and two females had bilateral TKA's. Inclusion criteria were patients with varus degenerative osteoarthritis of any degree scheduled for primary TKA who had not undergone previous ligament reconstruction surgery, knee osteotomy or suffered other trauma likely to distort the peri-articular soft tissues. Exclusion criteria were patients who declined to consent to participation or where intra-operatively placement of navigation pins was considered high risk due to poor bone stock or soft tissue. Ethical approval was attained from the relevant institutional review board and written informed consent was obtained pre-operatively for all patients.

A medial para-patellar approach to the knee was undertaken. Femoral and tibial navigation pins were inserted. All landmarks were identified and registered in the navigation system for calculation of the mechanical axes of the femur, tibia, lower limb and generation of an individualised 3D model of the patient's anatomy using computer navigation software (BrainLab, Munich, Germany). The status of the anterior cruciate ligament (ACL) and posterior cruciate ligament (PCL) was recorded. Osteophytes were left in-situ to assess the knee as close to its pathological OA state as possible. The anterior horn of the medial meniscus was left intact. Release of the deep band of the medial collateral ligament was left intact or limited to 5 mm by sharp dissection in order to maintain the state of medial soft tissues as close to the pre-operative state as possible whilst allowing clear navigation registration similar to the methods of Bellemans et al [5].

The patella was reduced and the degree of Fixed Flexion Deformity (FFD) or hyperextension was recorded in maximum extension. The mechanical axis of the limb was corrected, in maximal extension and 20° of flexion, by manipulating the knee while observing CAS displays. Direct observation of the joint was undertaken during this process to prevent subluxation and ensure congruency. These methods produced a limb position acting to define a neutral alignment for the knee consistent with prior literature [12, 13]. The knee was placed through a medial lateral arc with manual force from this corrected position. Laxity measurements were defined by medial and lateral displacement from the corrected axis point in degrees. These measurements were undertaken in maximal extension 93 and 20 degrees of flexion.

In 90° of flexion, neutral rotation and co-linearity of the femoral, tibial and limb axes was attained via CAS displays with observation of the joint again used to ensure congruency. Laxity was measured as medial and lateral displacement in degrees from this neutral point via the weight of the limb and manual force consistent with prior techniques [9, 10].

Modem navigation systems have been validated for these measurements [5]. In all cases, a single, high volume arthroplasty surgeon (MM) at a single centre performed the procedure and measurements. A CAS TKA was undertaken and the same measurements were repeated at the end of the procedure.

All data was prepared and analysed using Prism 5 for Mac OS X Version 5 (GraphPad Software Inc. La Jolla, CA). Direct statistical comparisons were made via Student's t-test. Any multiple comparison testing was completed using Tukey's Multiple Comparison Test.

Results

Sixty-five patients contributed 72 TKA's, five male and two female subjects had bilateral TKA's. The demographics of the study population are shown in Table 12.

Table 13 displays the results for medial and lateral laxity at each measurement position. Our results demonstrated a significant, though diminishing, difference between medial and lateral laxity at maximum extension $p<0.001$ (Mean−4.9°; 95% CI: −5.4° to −3.9°), 20° flexion $p<0.001$ (Mean−4.6°; 95% CI: −4.9° 115 to −2.9°) and 90° flexion $p<0.001$ (Mean−1.5°; 95% CI: −1.3° to −0.5°). Maximum extension versus 90° flexion laxity was significantly different on both the medial $p<0.001$ (Mean−2.2°; 95% CI: −3.2° to −1.3°) and lateral sides $p<0.001$ (Mean 1.5°; 95% CI: 0.6° to 2.5°).

The total medial-lateral coronal arcs were not significantly different at maximum extension and 90° of flexion. The total medial-lateral coronal arc at 20° of flexion was significantly greater compared with the arcs demonstrated at maximum extension ($p<0.001$; Mean−2.2°; 95% CI: −2.9° to −1.4°) and 90° flexion ($p<0.001$; Mean 1.5°, 95% CI: 0.7° to 2.2°).

The mean lateral minus medial laxity difference in 90° of flexion was 1.50+/−1.1° (0°-8°). Sixty-six (91.6%) knees had a difference of ≤2.5°; 3 (4.1%) knees a difference of 3; 2 (2.7%) knees 3.5° and 1 (1.4%) knee an 8° difference.

DISCUSSION

The improved outcomes associated with attaining a balanced knee post TKA have been documented [1,2]. If we can better understand the soft tissue envelope at the commencement of TKA then we can plan surgery to preserve or correct the soft tissue envelope. Current literature has examined in-vivo knee coronal plane laxity in different positions of flexion with differing investigative techniques and different patient groups. (Table 9 above) [5-10, 14-20]. This makes direct comparison of studies difficult. To our knowledge, the OA knee has not been examined in-vivo in 900 of flexion.

Our study is consistent with previously described measurement and surgical techniques and patient groups including flexion and varus deformity parameters [5, 7, 9, 10, 12, 13, 17, 18, 22]. We undertook laxity measurements with a reduced patella, which improves the accuracy of these measurements [21]. Arthrotomy of the knee does not significantly alter the medial-lateral laxity of the knee [16]. Firstly, to confirm our protocols produced broadly valid measurements we compared our results to prior in-vivo studies.

Figure 21:
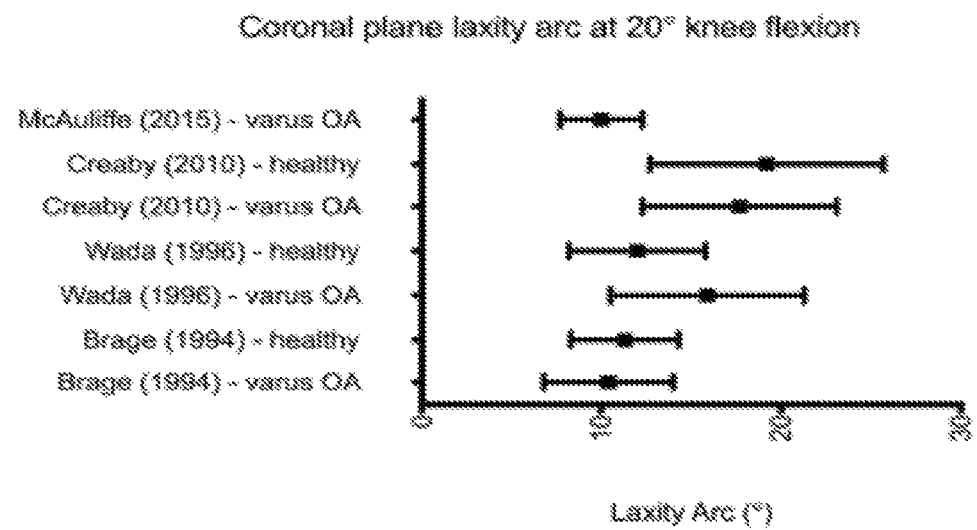
FIG. 21. Literature review of total coronal plane laxity arcs at 200 of knee flexion compared to current study data. Coronal plane laxity (mean and standard deviation) of moderate to severe osteoarthritis versus healthy (non-arthritic) knees demonstrates no difference for groups tested under similar conditions.

Many studies define coronal plane knee laxity by a total arc of movement at 20° of flexion. FIG. 21 compares these studies [14, 15, 18]. Our study is the largest varus OA group. It represents the first data for this parameter specifically documented at the time of TKA and demonstrates results consistent with these studies. Therefore, we believe the findings of our study are a valid contribution to the in-vivo literature in varus deformity of up to 15°, which was the maximum deformity in this series of subjects.

The purpose of our study was to define the medial and lateral laxity of the OA knee at the time of TKA in 90° of flexion and examine how osteoarthritis has altered it compared to the healthy knee. The studies of Brage, Wada and Creaby all demonstrate a non-significant difference between healthy and OA knees tested under the same conditions at 20° of flexion [14, 15, 18]. The alteration if any of the coronal plane tissue in the OA knee versus the healthy knee in 90° of flexion is unknown. The healthy knee displays different laxity parameters at 70-90° of flexion compared to extension and similar findings are present in a recent cadaver study [7, 8, 9, 11].

Coronal plane laxity at 90° of flexion is important to the outcome of a TKA. Studies have examined the end result of surgery but not the initial soft tissue envelope at the time of TKA [2, 23, 24, 25]. Whilst coronal plane tissue laxity in the OA knee at 90° of flexion remains unknown, it is uncertain whether TKA should reproduce or correct this laxity.

Our study has shown medial and lateral laxity measured from the neutral axis in 90° flexion to be 3.8°+/−1.4° and 4.7°+/−2° respectively. Only two studies have specifically examined medial and lateral laxity in the healthy knee in-vivo at 90° of flexion [9, 10]. Of these studies, Jenny has employed similar investigative techniques to our series in studying 20 normal knees at the time of anterior cruciate ligament reconstruction (ACLR) with computer navigation [9]. Whilst the knees of Jenny were ACL deficient, Wada et al reported no significant differences in total coronal laxity arcs between those with intact, partially ruptured or missing cruciate ligaments [14]. The difference between our lateral laxity and that of Jenny is non-significant. On the medial side, a significant difference is demonstrated ($p<0.0001$) with a mean difference of −1.7° (95% CI: −3.1° to −0.3°). This difference in medial laxity in our study compared with Jenny's is likely below or at the margin of clinical significance. Our laxity values are increased compared to their study, thus we found no evidence to suggest contractures of the coronal tissue in 900 flexion in the OA knee at the time of TKA. We also found a small (−0.9°) though statistically significant ($p<0.001$) difference between medial and lateral laxity in 90° of flexion. This finding is expected, other studies examining medial-lateral laxity in the healthy knee in 70°-900 of flexion have all found greater lateral than medial laxity. The statistical significance of these differences varied between studies [7-10]. Therefore it would appear that in 90° flexion when comparing the normal and OA knee there is relatively little real disturbance in the coronal plane soft tissue envelope and that laxity rather than contracture is the predominant effect of osteoarthritis in 900 of flexion. This is in keeping with the findings of studies at 20° of flexion comparing healthy and OA knee coronal movement arcs [14, 15, 18].

Literature regarding coronal plane laxity arcs at 900 of knee flexion is limited. Siston et al have published a figure of 3.1°+/−1.8° for an average coronal laxity arc in 900 of flexion in a series of 24 male varus and valgus knees without severe deformity at the time of TKA [20]. Ghosh et al demonstrated increasing laxity with increasing angles of knee flexion in their cadaveric study of eight knees and a laxity arc of 150 at 900 of flexion [16]. Comparison of these studies is difficult given different testing regimes and normal cadaveric knees compared to end stage OA knees [16,20]. We have demonstrated a laxity arc at 900 of knee flexion of 8.5°+/−3.0° (Range: 3°-16°). Our series did not show any significant change in the total coronal plane laxity arc between maximum extension and 90°. However, in extension there was a greater lateral contribution to the arc compared to flexion. The lateral tissues showed a mean decrease in laxity of 1.5° and the medial tissues a mean increase of 2.2° between maximum extension and 900 of flexion.

These findings have practical value in TKA given the importance of the soft tissue envelope and articular surface geometry in driving passive knee kinematics [25, 26]. In flexion, a total coronal arc of approximately 8.5° is an appropriate goal. Releases that affect the flexion gap should be minimised or avoided during the approach for TKA given the lack of evidence of contractures of the coronal soft tissues in this series. Both gap balancing and measured resection TKA techniques have demonstrated good outcomes and each has acknowledged advantages and disadvantages [27]. Our findings have implications for both these techniques.

In a gap-balanced technique, careful consideration should be given to the inherent flexion laxity. We have shown a small mean medial-lateral difference of 1.5°+/−1.1° and 91.6% of knees in our study had a medial-lateral difference of ≤2.5°. In addition, we have demonstrated lateral laxity consistent with healthy knees and medial laxity increased compared to healthy knees. Therefore, to achieve absolute balance and the rectangular gaps sought by the gap-balanced technique, further release of the already abnormal medial tissue or alterations of femoral implant rotation would be required to achieve this goal. Absolute medial lateral balance is not typical of the healthy knee in 900 of flexion [7-10]. It may be better to accept the inherent laxity of the knee given the close symmetry present in most patients. However, this would require further study given the optimal laxity post TKA in the peri-articular soft tissue envelope remains undetermined. We found a degree of inter-subject variability in coronal plane laxity with a maximum medial-lateral difference in 900 of flexion in our study of 8°. Some patients may not be suitable for a gap balancing technique.

For a measured resection technique, if bony cuts have accurately reproduced the patient's anatomy then balance in flexion should be substantially present. If large releases are required or significant imbalance is present then the accuracy of the bony resections should be assessed given the soft tissue tensions we have demonstrated in our subjects in 90° of flexion.

We would acknowledge possible limitations of our study. The patient group was predominantly Caucasian and their selection for TKA may not be indicative of other surgical series. However, the similarity of laxity and deformity parameters between our study and the literature examining the OA knee would suggest our patient group is consistent with other studies [9, 12, 14, 15, 18, 20]. Manual stress testing was performed to assess coronal plane laxity. Whilst an experienced surgeon performed this, some degree of variability in the forces exerted during testing would be expected. Mitigating this is the fact that ligaments are viscoelastic structures and measurements were recorded at maximal displacement. Therefore, measurements were recorded on the plateau of the tension/length curve minimising the effects of any variability in force [19]. Our testing methods are consistent with other in-vivo studies [5,9] It is not possible in an in-vivo setting to utilise the same invasive techniques with multiple controlled parameters and measurements that are utilised in cadaver studies given the ethical implications of prolonging surgery particularly in relation to infection risk. Consistent with prior studies, measurements were undertaken with minimal soft tissue disturbance designed to preserve the soft tissue envelope [5,9]. It is also possible to take a pragmatic view of our study given that our laxities were measured at a point in the surgical exposure less than that required to complete the operation. Therefore, the measured laxities would approximate those present at a point near the commencement of surgery and thus our results are useful for planning surgery from this initial point even if they do not represent the pure measure of medial and lateral laxity in the in-vivo setting of the end stage OA knee. This study did not specifically isolate the influence of extrinsic factors such as osteophytes both posteriorly and around coronal plane tissues. We do not expect these factors would have significantly influenced coronal plane laxity at 90°.

Conclusions

We have defined the coronal plane laxity of a large group of patients with end stage varus OA at the time of TKA in 900 of flexion. Our data would suggest that the alteration between the laxity of the OA knee and its native starting point in 90° of flexion is likely to be relatively small in knees with a varus deformity of up to 15°. This has important implications for both gap balancing and measured resection TKA techniques. Careful attention to initial laxity parameters in flexion may help drive more individualised coronal plane soft tissue laxity and avoid unnecessary releases or distortion of the coronal soft tissue envelope. It was beyond the scope of this paper but we have data on the post TKA soft tissue envelope and are currently following these subjects to examine the effect of TKA on the soft tissue envelope and the influence soft tissue laxity on the outcomes of TKA.

TABLE 12

Patient demographic details.

|  | Mean +/− SD | Range |
| --- | --- | --- |
| Age (years) | 64.1 +/− 7.2 | 49-81 |
| Sex | 35 Male, 30 Female |  |
| Body Mass Index (BMI) | 32.3 +/− 5.4 | 20.2-52.2 |

TABLE 12-continued

Patient demographic details.

| | Mean +/− SD | Range |
|---|---|---|
| FFD (degrees) | 5.1 +/− 5.4 | 20--8.5 |
| Varus (degrees) | −7.9 +/− 3.1 | −15--0.5 |

TABLE 13

Coronal plane laxity and total arcs of movement at maximum extension, 20°, 90° of flexion measured in degrees.

| Flexion | Medial laxity (°) | Lateral laxity (°) | Laxity arc (°) |
|---|---|---|---|
| Max extension | 1.6 +/− 1.1 (0-4) | 6.2 +/− 2.7 (0-12) | 7.8 +/− 2.4 (0-14) |
| 20° | 3.0 +/− 1.7 (0-7.5) | 7.0 +/− 2.9 (2-15) | 10.0 +/− 2.4 (6-16) |
| 90° | 3.8 +/− 1.4 (1-7.5) | 4.7 +/− 2.0 (1-12) | 8.5 +/− 3.0 (3-16) |

Values are expressed as mean +/− SD with range in brackets.

REFERENCES

1. Gustke K A, Golladay G J, Roche M D, Elson L C, Anderson C R. A New Method for 272 Defining Balance: Promising Short-Term Clinical Outcomes of Sensor Guided TKA. J Arthroplasty 2014; 29:955.
2. Seah R B, Yeo S J Y, Chin P K, Yew A K S, Chong H C, Lo N N. Evaluation of Medial-Lateral Stability and Functional Outcome Following Total Knee Arthroplasty: Results of a Single Hospital Joint Registry. J Arthroplasty 2014; 29: 2276.
3. Whiteside L A, Saeki K, Mihalko W M. Functional Medial Ligament Balancing in Total Knee Arthroplasty. Clin Orthop Relat Res 2000; 380:45.
4. Whiteside L A. Selective Ligament Release in Total Knee Arthroplasty of the Knee in Valgus. Clin Orthop Relat Res 1999; 367:130.
5. Bellemans J, Vandenneucker H, Vanlauwe J, Victor J. The Influence of Coronal Plane Deformity on Mediolateral Ligament Status: An Observational Study in Varus Knees. Knee Surg Sports Traumatol Arthrosc 2010; 18:152.
6. Okamoto S, Okazaki K, Mitsuyasu H, Matsuda S, Iwamoto Y. Lateral Soft Tissue Laxity Increases but Medial Laxity does not Contract with Varus Deformity in Total Knee Arthroplasty. Clin Orthop Rel Res 2013; 471:1334.
7. Heesterbeek P J C, Verdonschot N, Wymenga A B. In Vivo Knee Laxity in Flexion and Extension: A Radiographic Study in 30 Older Healthy Subjects. The Knee 2008; 15:45.
8. Okazaki K, Miura H, Matsuda S, Takeuchi N, Mawatari T, Hashizume Metal. Asymmetry of Mediolateral Laxity of the Normal Knee. J Orthop Sci 2006; 11:264.
9. Jenny J-Y. Coronal Plane Knee Laxity Measurement: Is Computer-Assisted Navigation Useful? Orthop & Traumatol: Surg and Res 2010; 96(5):583.
10. Tokuhara Y, Kadoya Y, Nakagawa S, Kobayashi A, Takaoka K. The Flexion Gap in Normal Knees: An MRI Study. J Bone Joint Surg Br 2004; 86-B:1133.
11. Roth J D, Howell S M, Hull M L. Native Knee Laxities at 00, 450 and 900 of Flexion and their Relationship to the Goal of the Gap-Balancing Alignment Method of Total Knee Arthroplasty. J Bone Joint Surg Am 2015; 97:1678.
12. Cooke D, Scudamore A, Li J, Wyss U, Bryant T, Costigan P. Axial Lower Limb Alignment: Comparison of Knee Geometry in Normal Volunteers and Osteoarthritic Patients. Osteoarthritis and Cartilage 1997; 5:39.
13. Bellemans J, Colyn W, Vandenneucker H, Victor J. The 302 Chitranjan Ranawat Award: Is Neutral Mechanical Alignment Normal for All Patients? The Concept of Constitutional Varus. Clin Orthop Rel Res 2012; 470:45.
14. Wada M, Imura S, Baba H, Shimada S. Knee Laxity in Patients with Osteoarthritis and Rheumatoid Arthritis. Br J of Rheum 1996; 35(6):560.
15. Brage M E, Draganich L F, Pottenger L A, Curran J J. Knee Laxity in Symptomatic Osteoarthritis. Clin Orthop Rel Res 1994; 304:184.
16. Ghosh K M, Blain A P, Longstaff L, Rushton S, Amis A A, Deehan D J. Can we Define Envelope of Laxity During Navigated Knee Arthroplasty? Knee Surg Sports Traumatol Arthrosc 2014; 22:1736.
17. Pottenger L A, Phillips F M, Draganich L F. The Effect of Marginal Osteophytes on Reduction of Varus-Valgus Instability in Osteoarthritic Knees. Arthritis and Rheumatism. 1990 June; 33(6):853.
18. Creaby M W, Wrigley T V, Lim B W, Bowles K, Metcalf B R, Hinman R S et al. Varus-Valgus Laxity and Passive Stiffness in Medial Knee Osteoarthritis. Arthritis Care Res 2010; 62(9):1237.
19. Markolf K L, Mensch J S, Amstutz H C. Stiffness and Laxity of the Knee—the Contributions of the Supporting Structures. A Quantitative in Vitro Study. J Bone Joint Surg Am 1976; 58-A(5):583.
20. Siston R A, Goodman S B, Delp S L, Giori N J. Coronal Plane Stability Before and After Total Knee Arthroplasty. Clin Orthop Rel Res 2007; 463:43.
21. Matsumoto T, Muratsu H, Tsumura N, Mizuno K, Kurosaka M, Kuroda R. Soft Tissue Balance Measurement in Posterior-Stabilized Total Knee Arthroplasty With a Navigation System. J Arthroplasty 2009; 24:358.
22. Hohman D W, Nodzo S R, Phillips M, Fitz Wolfgang. The 326 Implications of Mechanical Alignment on Soft Tissue Balancing in Total Knee Arthroplasty. Knee Surg Sports Traumatol Arthrosc 2014 Sep. 13 [Epub ahead of print].
23. Aunan E, Kibsgard T, Clarke-Jenssen J, Rohrl S M. A New Method to Measure Ligament Balancing in Total Knee Arthroplasty: Laxity Measurements in 100 Knees. Arch Orthop Trauma Surg 2012; 132:1173.
24. Joseph J, Simpson P M S, Whitehouse S L, English H W, Donnelly W J. The Use of Navigation to Achieve Soft Tissue Balance in Total Knee Arthroplasty—A Randomized Clinical Study. The Knee 2013; 20:401.
25. Aunan E, Kibsgard T, Diep L M, Rohrl S M. Intraoperative Ligament Laxity Influences Functional Outcome 1 Year after Total Knee Arthroplasty. Knee Surg Sports Traumatol Arthrosc 2015; 23:1684.
26. Wilson D R, Feikes J D, O'Connor J J. Ligaments and Articular Contact Guide Passive Knee Flexion. J Biomech 1998; 31:1127
27. Blankevoort L, Huiskes R, de Lange A. The Envelope of Passive Knee Joint Motion. J Biomech 1988; 21:705
28. Dennis D A, Komistek, R D, 342 Kim R H, Sharma A. Gap Balancing versus Measured Resection Technique for Total Knee Arthroplasty. Clin Orthop Relat Res 2010; 468:102.

The invention claimed is:

1. A method of designing a patient-specific surgical device for performing knee surgery on the patient including the steps of:

(i) obtaining patient-specific anatomical data of a patient's limb in flexion and/or extension;
(ii) pre-processing and/or converting the patient-specific anatomical data to form a patient-specific three dimensional model of the limb;
(iii) determining a first alignment axis from a plurality of first anatomical indicators on the patient-specific three dimensional model of the limb in extension;
(iv) determining a second alignment axis from a plurality of second anatomical indicators on the patient-specific three dimensional model of the limb in flexion;
(v) determining a flexion axis from a plurality of third anatomical indicators on the patient-specific three-dimensional model of the limb in flexion;
(vi) determining a joint line from a plurality of fourth anatomical indicators, wherein the fourth anatomical indicators comprise a landmark on patient's tibia and at least one of the first anatomical indicators, the second anatomical indicators, and the third anatomical indicators comprise a landmark on a patient's femur;
(vii) designing the patient-specific surgical device based at least partly on the determined first and/or second alignment axes so that the patient-specific surgical device is adapted to at least partly align a femur and/or a tibia of said limb with the first and/or second alignment axes; and
(viii) creating the patient-specific surgical device based on the design of the patient-specific surgical device.

2. The method of claim 1, wherein the plurality of first anatomical indicators are selected from the group consisting of a central portion of a femoral head, a central portion of a proximal femoral shaft, an intramedullary canal insertion point, a deepest portion of a trochlear groove, a central portion of an intercondylar notch, a central portion of a line extending between medial and lateral tibial spines, a central portion of a talus, a central portion of a distal tibial shaft and an anterior cruciate ligament tibial attachment point.

3. The method of claim 1, wherein the first alignment axis is or comprises a tibial mechanical axis, a femoral mechanical axis and/or a lower limb mechanical axis or an axis substantially parallel thereto.

4. The method of claim 3, further including the step of rotating the tibia of the extended limb in a coronal plane relative to the femur, such that the tibial mechanical axis, the femoral mechanical axis and/or the lower limb mechanical axis are substantially parallel to the first alignment axis.

5. The method of claim 1, wherein the plurality of second anatomical indicators is or comprises: (i) a femoral anteroposterior axis and/or a tibial anteroposterior axis and the second alignment axis is substantially parallel thereto; and/or (ii) a transepicondylar axis (TEA) and/or a posterior condylar axis and the second alignment axis is substantially perpendicular thereto.

6. The method of claim 1, wherein determining a flexion axis from a plurality of third anatomical indicators on the patient-specific three-dimensional model of the limb, comprises rotating the tibia relative to the femur about the flexion axis so as to substantially match the degree of flexion that exists between the femur and tibia in patient-specific anatomical data of the limb in flexion.

7. The method of claim 6, wherein the plurality of third anatomical indicators are or comprise a lateral condyle arc centre and a medial condyle arc centre of the femur, such that the flexion axis extends therebetween.

8. The method of claim 6, wherein the plurality of second anatomical indicators is or comprises the flexion axis and the second alignment axis is substantially perpendicular thereto.

9. The method of claim 1, wherein the plurality of fourth anatomical indicators are selected from the group consisting of a proximal portion of a medial tibial plateau, a proximal portion of a lateral tibial plateau, a central portion of a lateral meniscus and a central portion of a medial meniscus.

10. The method of claim 1, further comprising the step of determining a distal resection plane of the femur when the knee is in extension from at least partly the joint line of the knee, the first alignment axis and/or a first dimension of a femoral prosthesis to be fitted on said femur.

11. The method of claim 10, wherein the distal femoral resection plane is substantially parallel to the joint line of the knee and/or is substantially perpendicular to the first alignment axis.

12. The method of claim 10, wherein the distance between the joint line and the distal resection plane are substantially equal to the first dimension of the femoral prosthesis.

13. The method of claim 10, wherein the distance between the joint line and the distal resection plane is about 0.5 mm to about 1.5 mm greater than the first dimension of the femoral prosthesis.

14. The method of claim 10, further comprising the step of determining a proximal resection plane of the tibia when the knee is in extension from at least partly the distal femoral resection plane, the first dimension of the femoral prosthesis to be fitted on said femur, a first dimension of a tibial prosthesis to be fitted on said tibia and the joint line.

15. The method of claim 14, wherein the proximal tibial resection plane is: (i) substantially parallel to the joint line of the knee in extension; (ii) substantially perpendicular to the first alignment axis; and/or (iii) substantially parallel to the distal resection plane of the knee in extension, when viewed in a coronal and/or sagittal plane of the limb.

16. The method of claim 14, wherein the proximal resection plane is at an angle of (i) about 0.5 degrees to about 15 degrees relative to the joint line and/or the distal femoral resection plane; and/or (ii) about 75 degrees to about 89.5 degrees relative to the first alignment axis, when viewed in a sagittal plane of the limb.

17. The method of claim 14, wherein the distance between the distal femoral resection plane and the proximal tibial resection plane are substantially equal to the sum of the first dimension of the femoral prosthesis and the first dimension of the tibial prosthesis.

18. The method of claim 14, wherein the distance between the distal resection plane and the proximal resection plane is about 0.5 mm to about 2.5 mm greater than the sum of the first dimension of the femoral prosthesis and the first dimension of the tibial prosthesis.

19. The method of claim 14, further including the step of rotating the tibia of the flexed limb in a coronal plane relative to the femur, such that the proximal resection plane is substantially perpendicular to the second alignment axis.

20. The method of claim 14, further comprising the step of determining a posterior resection plane of the femur when the knee is in flexion from at least partly the second alignment axis, the proximal tibial resection plane, the first dimension of the tibial prosthesis to be fitted on the tibia and/or a second dimension of the femoral prosthesis to be fitted on the femur.

21. The method of claim 20, wherein the posterior resection plane is substantially perpendicular to the second alignment axis and/or is substantially parallel to the proximal tibial resection plane when viewed in a coronal and/or sagittal plane of the limb.

22. The method of claim 20, wherein the proximal resection plane is at an angle of: (i) about 0.5 degrees to about 15 degrees relative to the posterior resection plane; and/or (ii) about 75 degrees to about 89.5 degrees relative to the second alignment axis, when viewed in a sagittal plane of the limb.

23. The method of claim 20, wherein the distance between the posterior resection plane and the proximal resection plane is substantially equal to the sum of the first dimension of the tibial prosthesis and the second dimension of the femoral prosthesis.

24. The method of claim 20, wherein the distance between the posterior resection plane and the proximal resection plane is about 0.5 mm to about 2.5 mm greater than the sum of the first dimension of the tibial prosthesis and the second dimension of the femoral prosthesis.

25. The method of claim 20, wherein the distal resection plane defines a distal femoral cut thickness and positioning, the proximal resection plane defines a proximal tibial cut thickness and positioning and/or the posterior resection plane defines a posterior femoral cut thickness and positioning such that a post-resection gap from said tibia to said femur is approximately equal in extension and in flexion of the knee.

26. The method of claim 20, further comprising the step of determining a position of a plurality of guide apertures in the patient-specific surgical device for indicating or facilitating positioning of a resection member on the femur and/or tibia, wherein the resection member comprises a plurality of resection apertures for guiding a resection tool along the distal resection plane, the proximal resection plane, the posterior resection plane and/or an anterior resection plane of the femur.

27. The method of claim 26, wherein the guide apertures indicate or facilitate positioning of (i) a distal resection member on the femur; (ii) a proximal resection member on the tibia; and/or (iii) an anteroposterior resection member on the femur.

28. The method of claim 20, further comprising the step of determining a position of a plurality of resection apertures in the patient-specific surgical device for guiding a resection tool along the distal resection plane, the proximal resection plane, the posterior resection plane and/or an anterior resection plane of the femur.

29. The method of claim 1, wherein the patient-specific three-dimensional model of the limb is created using both soft tissue and bony tissue data from the patient-specific anatomical data.

30. The method of claim 1, wherein the patient-specific surgical device comprises a spacer for insertion between the femur and tibia to facilitate at least partly return of the knee to an appropriate alignment with the first alignment axis and/or the second alignment axis.

31. The method of claim 1, wherein the patient-specific surgical device facilitates at least partly return of the knee to an appropriate and/or balanced soft tissue tension when in extension and/or flexion; and wherein:
   for appropriate soft tissue tension, medial and/or lateral soft tissue laxity of the knee in flexion and/or extension is about 1° to about 7.0°; and
   for balanced soft tissue tension, the difference between medial and lateral soft tissue laxity of the knee is or less than about 5°.

* * * * *